(12) United States Patent
Schultz et al.

(10) Patent No.: US 10,166,237 B2
(45) Date of Patent: *Jan. 1, 2019

(54) COMPOUNDS AND METHODS FOR INDUCING CHONDROGENESIS

(71) Applicant: The Scripps Research Institute, La Jolla, CA (US)

(72) Inventors: Peter Schultz, La Jolla, CA (US); Laure Bouchez, Basel (CH)

(73) Assignee: The Scripps Research Institute, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/256,230

(22) Filed: Sep. 2, 2016

(65) Prior Publication Data

US 2017/0112843 A1 Apr. 27, 2017

Related U.S. Application Data

(63) Continuation of application No. 14/007,306, filed as application No. PCT/US2012/030567 on Mar. 26, 2012, now Pat. No. 9,464,065.

(Continued)

(51) Int. Cl.

| | |
|---|---|
| *A61K 31/5375* | (2006.01) |
| *A61K 38/18* | (2006.01) |
| *A61K 38/23* | (2006.01) |
| *A61K 38/39* | (2006.01) |
| *A61K 31/505* | (2006.01) |
| *A61K 31/593* | (2006.01) |
| *A61K 31/728* | (2006.01) |
| *A61K 36/54* | (2006.01) |
| *C07C 255/57* | (2006.01) |
| *C07C 255/60* | (2006.01) |
| *C07D 257/04* | (2006.01) |
| *C07C 233/75* | (2006.01) |
| *C07C 233/80* | (2006.01) |
| *C07C 233/81* | (2006.01) |
| *C07D 277/46* | (2006.01) |

(Continued)

(52) U.S. Cl.
CPC ........ *A61K 31/5375* (2013.01); *A61K 31/167* (2013.01); *A61K 31/192* (2013.01); *A61K 31/194* (2013.01); *A61K 31/277* (2013.01); *A61K 31/357* (2013.01); *A61K 31/365* (2013.01); *A61K 31/404* (2013.01); *A61K 31/4035* (2013.01); *A61K 31/41* (2013.01); *A61K 31/4188* (2013.01); *A61K 31/4192* (2013.01); *A61K 31/421* (2013.01); *A61K 31/423* (2013.01); *A61K 31/426* (2013.01); *A61K 31/428* (2013.01); *A61K 31/433* (2013.01); *A61K 31/44* (2013.01); *A61K 31/4402* (2013.01); *A61K 31/4439* (2013.01); *A61K 31/47* (2013.01); *A61K 31/4965* (2013.01); *A61K 31/505* (2013.01); *A61K 31/593* (2013.01); *A61K 31/728* (2013.01); *A61K 36/54* (2013.01); *A61K 38/1816* (2013.01); *A61K 38/1825* (2013.01); *A61K 38/23* (2013.01); *A61K 38/39* (2013.01); *A61K 45/06* (2013.01); *C07C 233/75* (2013.01); *C07C 233/80* (2013.01); *C07C 233/81* (2013.01); *C07C 255/50* (2013.01); *C07C 255/57* (2013.01); *C07C 255/60* (2013.01); *C07D 209/48* (2013.01); *C07D 215/14* (2013.01); *C07D 241/24* (2013.01); *C07D 249/06* (2013.01); *C07D 257/04* (2013.01); *C07D 263/57* (2013.01); *C07D 277/46* (2013.01); *C07D 277/66* (2013.01); *C07D 295/135* (2013.01); *C12N 5/0655* (2013.01); *A61K 9/0024* (2013.01)

(58) Field of Classification Search
CPC .... A61K 31/505; A61K 31/423; A61K 31/47; A61K 31/4965; A61K 31/5375; A61K 31/167; A61K 31/192; A61K 31/194; A61K 31/277; A61K 31/357; A61K 31/365; A61K 31/4035; A61K 31/404; A61K 31/41; A61K 31/4188; A61K 31/421; A61K 31/426; A61K 31/433; A61K 31/44; A61K 31/4402; A61K 31/4439; A61K 31/593; A61K 31/728; A61K 36/54; A61K 38/1816; A61K 38/1825; A61K 38/23; A61K 38/39; A61K 31/4192; A61K 31/428; A61K 45/06; A61K 9/0024; C07C 233/75; C07C 233/80; C07C 233/81; C07C 255/50; C07C 255/57; C07C 255/60; C07D 209/48; C07D 215/14; C07D 241/24; C07D 249/06; C07D 257/04; C07D 263/57; C07D 277/46; C07D 277/66; C07D 295/135; C12N 5/0655
USPC ....................................... 514/239.5
See application file for complete search history.

(56) References Cited

U.S. PATENT DOCUMENTS 3,793,458 A 2/1974 Wermuth et al.
9,452,170 B2 * 9/2016 Schultz ................ C07C 255/60
(Continued)

OTHER PUBLICATIONS

Able, et al., "Receptor localization, native tissue binding and ex vivo occupancy for centrally penetrant P2X7 antagonists in the rat," *Br J Pharmacol*, vol. 162(2), pp. 405-414 (Jan. 2011).

(Continued)

*Primary Examiner* — My-Chau T. Tran
(74) *Attorney, Agent, or Firm* — Kilpatrick Townsend & Stockton LLP

(57) ABSTRACT

The present invention provides compounds and compositions for the amelioration of arthritis and joint injuries by inducing mesenchymal stem cells into chondrocytes.

21 Claims, 18 Drawing Sheets

Related U.S. Application Data

(60) Provisional application No. 61/467,289, filed on Mar. 24, 2011.

(51) Int. Cl.

| | |
|---|---|
| C07D 209/48 | (2006.01) |
| A61K 31/4192 | (2006.01) |
| A61K 31/423 | (2006.01) |
| A61K 31/428 | (2006.01) |
| A61K 31/47 | (2006.01) |
| A61K 31/4965 | (2006.01) |
| A61K 45/06 | (2006.01) |
| C07C 255/50 | (2006.01) |
| C07D 215/14 | (2006.01) |
| C07D 241/24 | (2006.01) |
| C07D 249/06 | (2006.01) |
| C07D 263/57 | (2006.01) |
| C07D 277/66 | (2006.01) |
| C07D 295/135 | (2006.01) |
| C12N 5/077 | (2010.01) |
| A61K 31/167 | (2006.01) |
| A61K 31/192 | (2006.01) |
| A61K 31/194 | (2006.01) |
| A61K 31/277 | (2006.01) |
| A61K 31/357 | (2006.01) |
| A61K 31/365 | (2006.01) |
| A61K 31/4035 | (2006.01) |
| A61K 31/404 | (2006.01) |
| A61K 31/41 | (2006.01) |
| A61K 31/4188 | (2006.01) |
| A61K 31/421 | (2006.01) |
| A61K 31/426 | (2006.01) |
| A61K 31/433 | (2006.01) |
| A61K 31/44 | (2006.01) |
| A61K 31/4402 | (2006.01) |
| A61K 31/4439 | (2006.01) |
| A61K 9/00 | (2006.01) |

(56) References Cited

U.S. PATENT DOCUMENTS 9,464,065 B2 * 10/2016 Schultz .............. A61K 38/1816
2007/0142329 A1    6/2007 Dombroski et al.
2016/0045514 A1 *  2/2016 Schultz ................ C07C 255/60
                                                        424/757

OTHER PUBLICATIONS

PubChem compound CID 78458 (create date: Mar. 26, 2005) (retrieved from http://pubchem.ncbi.nlm.nih.gov/summary/summary.cgi?cid=78458 on Jun. 13, 2012).

International Search Report and Written Opinion for International Application No. PCT/US12/30567, 12 pages, dated Sep. 21, 2012.

* cited by examiner

Histological Representations of Cartilage Damage

PBS          10μM PRO1

Joint Score (8 weeks)

Anti-Biotin identification of FLNA

Expression of FLNA in hMSC

Inhibition of PEPB2β / FLNA interaction

IP: PEBP2β, Western: FLNA (90 kDa fragment)

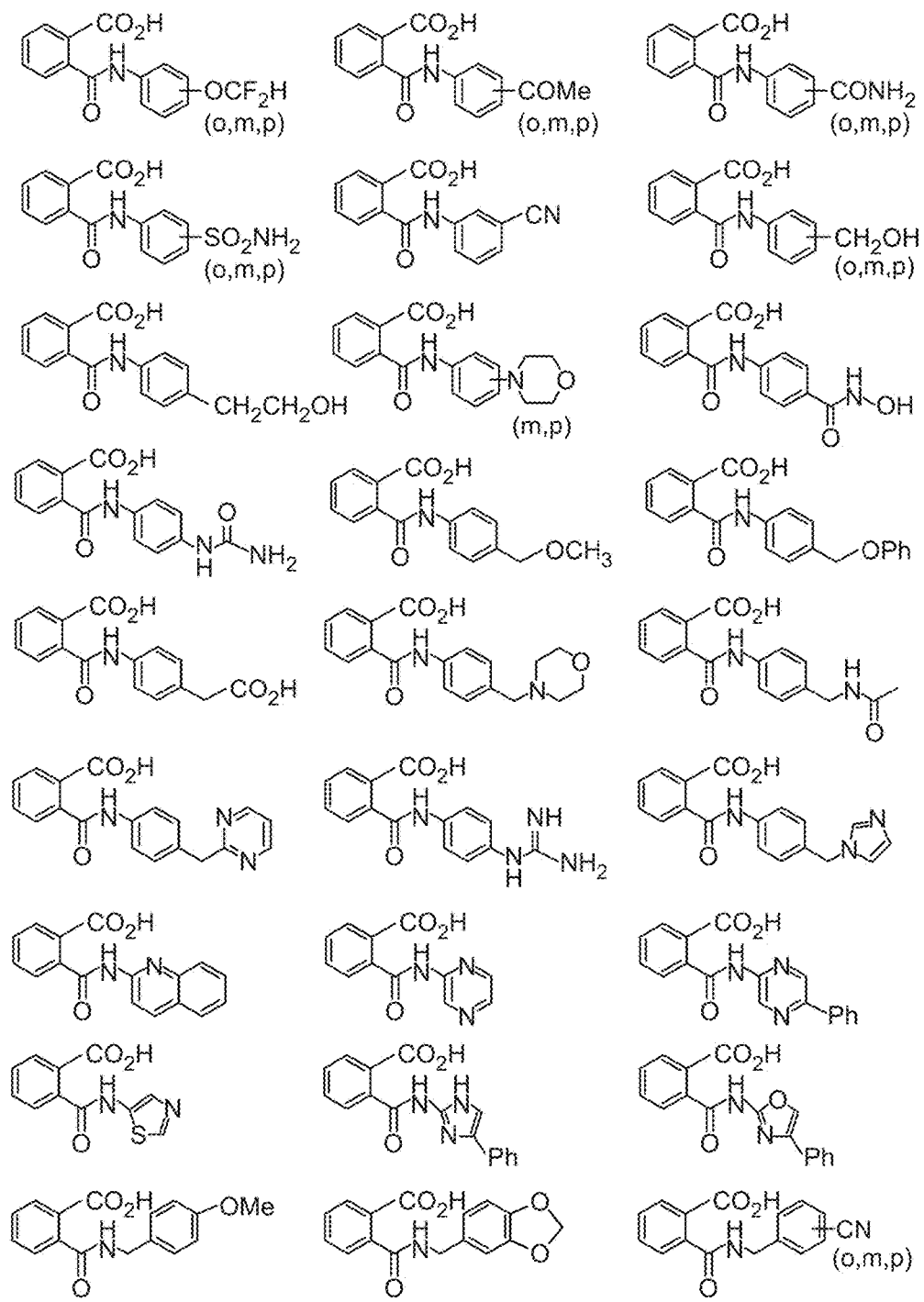
FIG. 8 (Cont. 1)

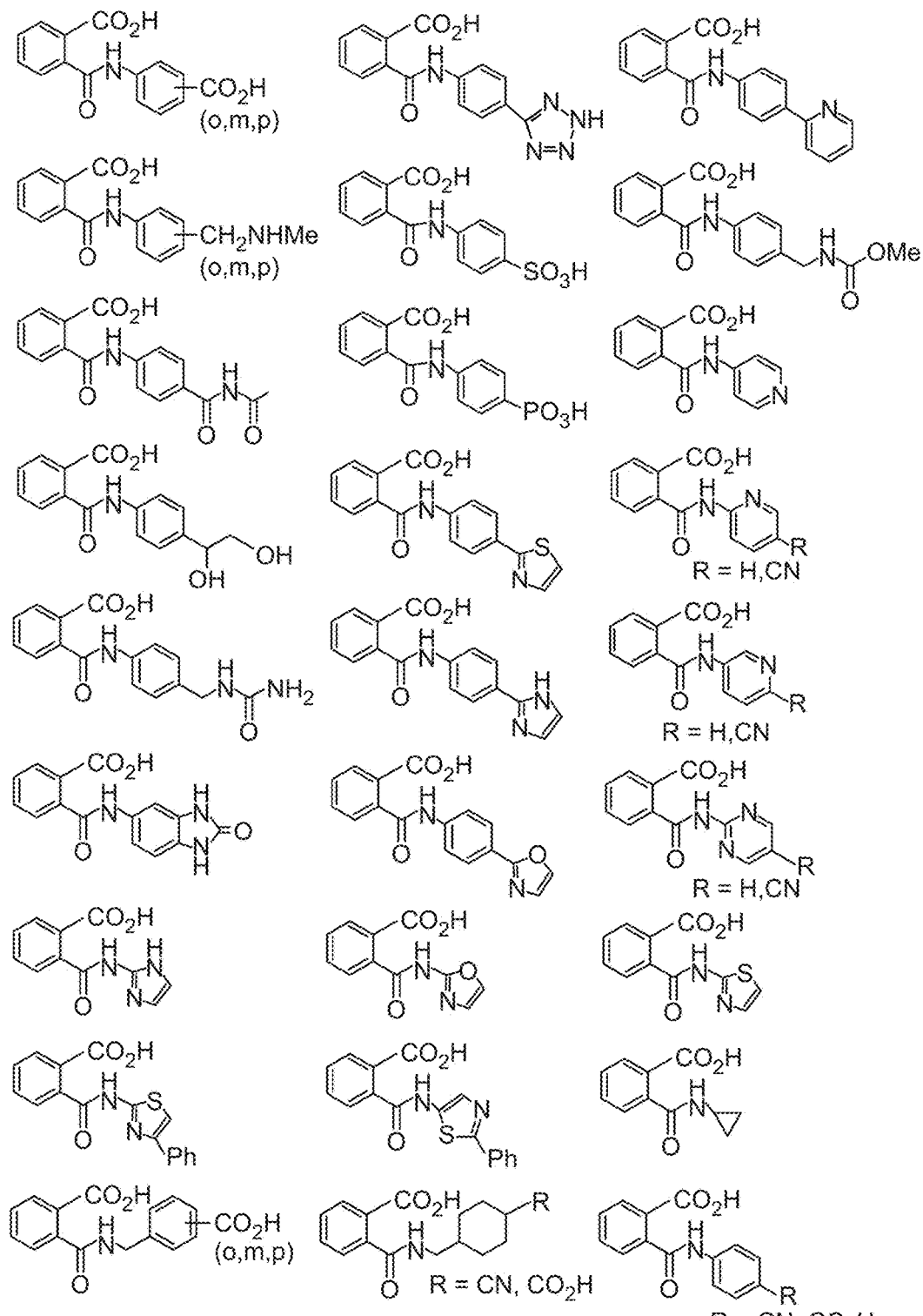
FIG. 8 (Cont. 2)

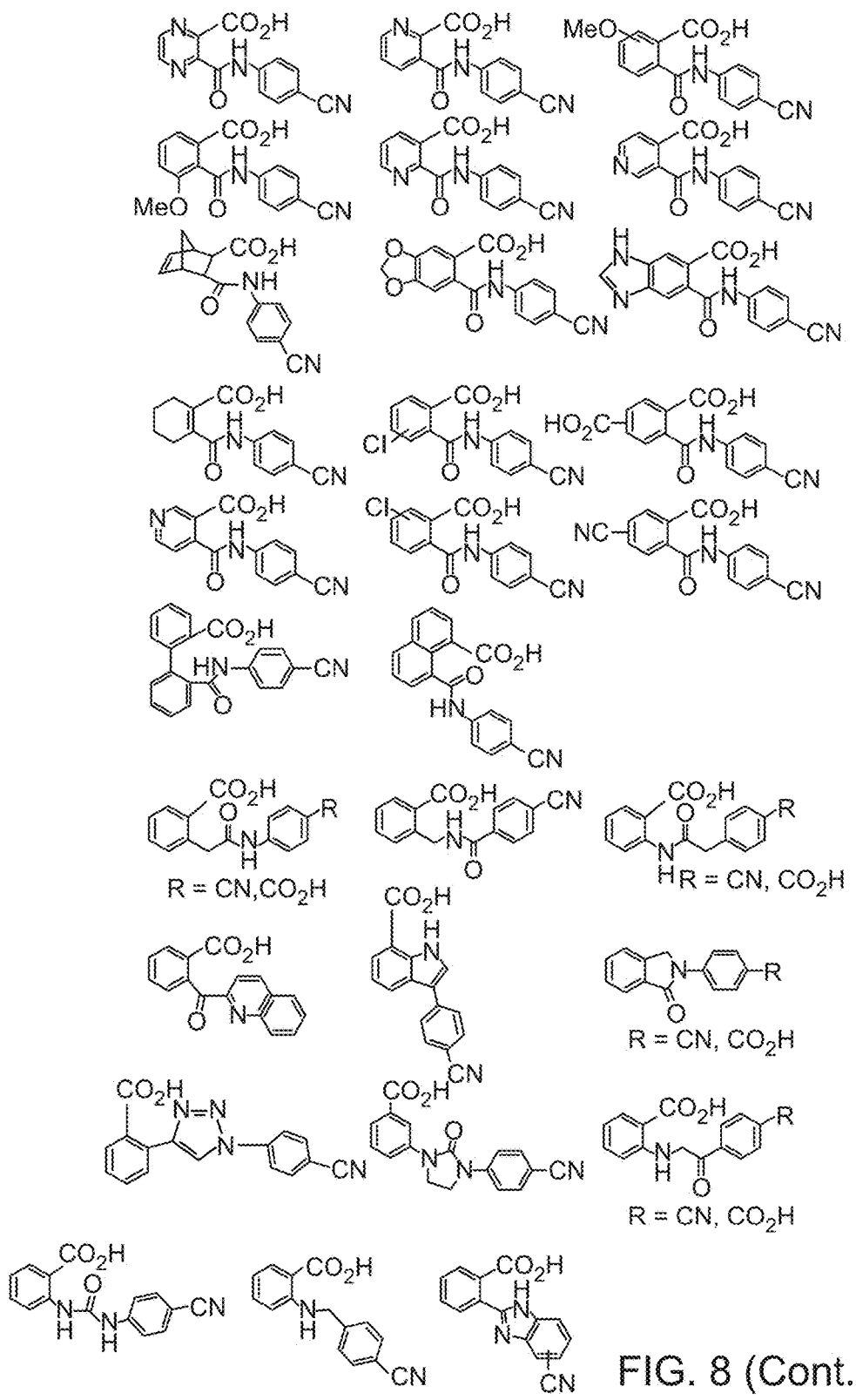
FIG. 8 (Cont. 3)

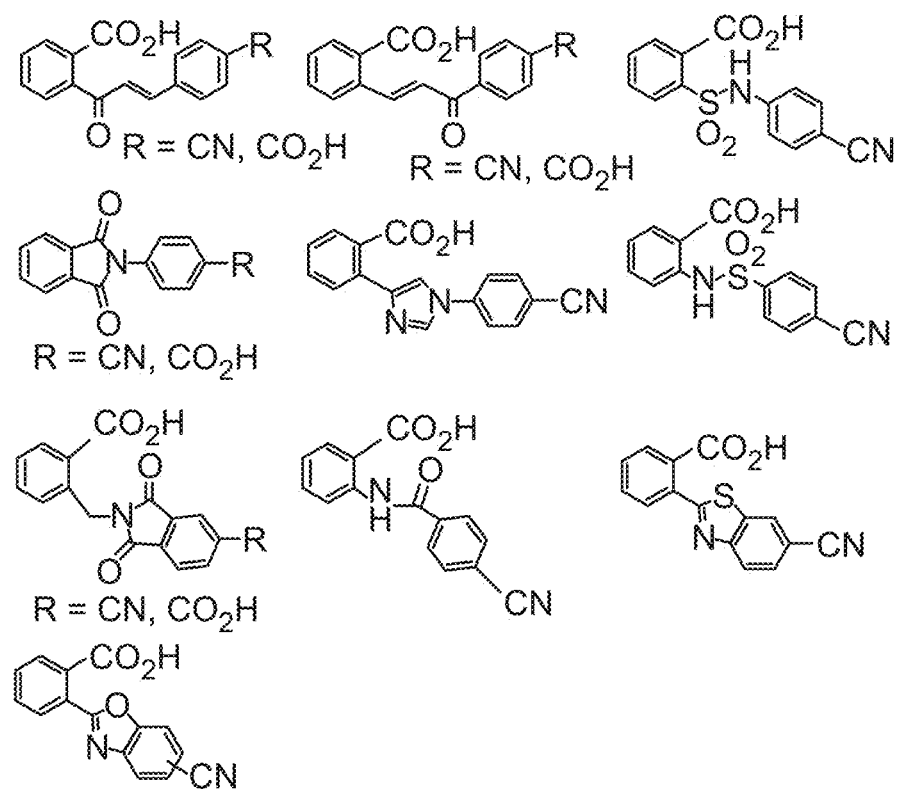
FIG. 8 (Cont. 4)

COMPOUNDS AND METHODS FOR INDUCING CHONDROGENESIS

CROSS-REFERENCES TO RELATED APPLICATIONS

This application is a continuation of U.S. application Ser. No. 14/007,306, filed Jan. 8, 2014, which is the U.S. National Stage Entry under § 371 of International Application No. PCT/US2012/030567, filed Mar. 26, 2012, which claims priority to U.S. Provisional Application No. 61/467,289, filed Mar. 24, 2011, which is incorporated in its entirety herein for all purposes.

BACKGROUND OF THE INVENTION

Osteoarthritis (OA) represents the most common musculoskeletal disorder. Approximately 40 million Americans are currently affected and this number is predicted to increase to 60 million within the next twenty years as a result of the aging population and an increase in life expectancy, making it the fourth leading cause of disability. OA is characterized by a slow degenerative breakdown of the joint including both the articular cartilage (containing the cells and matrix which produce lubrication and cushioning for the joint) and the subchondral bone underlying the articular cartilage. Current OA therapies include pain relief with oral NSAIDs or selective cyclooxygenase 2 (COX-2) inhibitors, intra-articular (IA) injection with agents such as corticosteroids and hyaluronan, and surgical approaches.

Mesenchymal stem cells (MSCs) are present in adult articular cartilage and upon isolation can be programmed in vitro to undergo differentiation to chondrocytes and other mesenchymal cell lineages. In part it is regulated by growth factors (TGFβs, BMPs), serum conditions and cell-cell contact.

BRIEF SUMMARY OF THE INVENTION

In one embodiment, the present invention provides a method of ameliorating arthritis or joint injury in a mammal, the method including administering to a joint of the mammal a composition having a therapeutically effective amount of a compound of formula I:

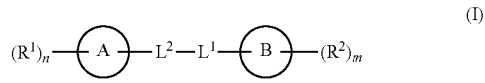

(I)

In formula I, each of ring A and ring B are independently cycloalkyl, aryl or heteroaryl.

In formula I, each $R^1$ and $R^2$ is independently H, $C_{1-6}$ alkyl, $C_{2-6}$ alkenyl, $C_{2-6}$ alkynyl, $C_{1-6}$ alkoxy, $C_{1-6}$ heteroalkyl, halogen, $C_{1-6}$ haloalkyl, $C_{1-6}$ haloalkoxy, $C_{1-6}$ alkyl-CN, $C_{1-6}$ alkylhydroxy, $-OR^{2a}$, $-NR^{2b}R^{2d}$, $C_{1-6}$ alkyl-$NR^{2b}R^{2d}$, $-C(O)R^{1a}$, $-C(O)R^{2d}$, $-C(O)OR^{2a}$, $C_{1-6}$ alkyl-C(O)$OR^{2b}$, $-OC(O)R^{2b}$, $-OC(O)OR^{2b}$, $-C(O)NR^{2a}R^{2b}$, $-C(O)N(OH)R^{2b}$, $-NR^{2b}C(O)R^{2c}$, $C_{1-6}$ alkyl-$NR^{2b}C(O)R^{2c}$, $-NR^{2b}C(O)OR^{2c}$, $C_{1-6}$ alkyl-$NR^{2b}C(O)OR^{2c}$, $-OC(O)NR^{2b}R^{2c}$, $-NR^{2b}C(O)NR^{2b}R^{2c}$, $-NR^{2b}C(NR^{2b})NR^{2b}R^{2c}$, $-C(O)NR^{2b}C(O)R^{2b}$, $C_{1-6}$ alkyl-$C(O)NR^{2b}R^{2c}$, $-SR^{2a}$, $-SO_2R^{2b}$, $-SO_2OR^{2b}$, $-SO_2NR^{2b}R^{2d}$, $-NR^{2b}SO_2R^{2b}$, $-P(O)(OR^{2b})_2$, $-B(OR^{2b})$, $-CN$, $-NO_2$, $-N_3$, heterocycloalkyl, aryl, heteroaryl, $C_{1-6}$ alkyl-heterocycloalkyl, $C_{1-6}$ alkyl-aryl, $C_{1-6}$ alkyl-O-aryl, $C_{1-6}$ alkyl-heteroaryl, or heteroaryl-aryl, and wherein the heterocycloalkyl, aryl and heteroaryl groups are optionally substituted with 1 to 2 $R^{2a}$ groups.

In formula I, $R^{1a}$ is $-OR^{1b}$ or $-NR^{1b}R^{1c}$; $R^{1b}$ and $R^{1c}$ are each independently H, $C_{1-6}$ alkyl, $C_{2-6}$ alkenyl, $C_{2-6}$ alkynyl, cycloalkyl, heterocycloalkyl, aryl, heteroaryl, $C_{1-6}$ alkyl-aryl, or $C_{1-6}$ alkyl-heteroaryl, wherein the cycloalkyl, heterocycloalkyl, aryl and heteroaryl groups are optionally substituted with from 1 to 4 $R^{1d}$ groups; and each $R^{1d}$ is independently H, $C_{1-6}$ alkyl, $C_{1-6}$ alkoxy, or $-NO_2$.

In formula I, each $R^{2a}$ is independently H, $C_{2-6}$ alkenyl, $C_{2-6}$ alkynyl, cycloalkyl, heterocycloalkyl, aryl, heteroaryl, $C_{1-6}$ alkyl-cycloalkyl, $C_{1-6}$ alkyl-heterocycloalkyl, $C_{1-6}$ alkyl-aryl or $C_{1-6}$ alkyl-heteroaryl, optionally substituted with 1 to 2 $R^{2b}$ groups; each $R^{2b}$ and $R^{2c}$ is independently H, or $C_{1-6}$ alkyl; and each $R^{2d}$ is independently H, $C_{1-6}$ alkyl, cycloalkyl, heterocycloalkyl, aryl, heteroaryl, $C_{1-6}$ alkyl-cycloalkyl, $C_{1-6}$ alkyl-heterocycloalkyl, $C_{1-6}$ alkyl-aryl or $C_{1-6}$ alkyl-heteroaryl, each optionally substituted with 1 to 2 $R^{2b}$ groups.

In formula I, each of $L^1$ and $L^2$ are independently $L^1$ and $L^2$ are independently a bond, $C_{1-6}$ alkylene, $C_{2-6}$ alkenylene, $C_{1-6}$ alkylene-O—, —O—$C_{1-6}$ alkylene, $C_{1-6}$ alkylene-$NR^{3a}$—, —$NR^{3a}$—$C_{1-6}$ alkylene, —C(O)—, $C_{1-6}$ alkylene-C(O)—, —C(O)—$C_{1-6}$ alkylene-NH—, —NH—$C_{1-6}$ alkylene-C(O)—, —C(O)NH—, —NHC(O)—, $C_{1-6}$ alkylene-NHC(O)—, —$SO_2NH$—, —$NHSO_2$—, —NHC(O)NH—, cycloalkylene, —N=N—, or —$C(R^{3a})$=$N(R^{3c})$—, wherein the alkylene group is optionally substituted with from 1-4 $R^{3b}$ groups. $R^{3a}$ of formula I is H or $C_{1-6}$ alkyl. Each $R^{3b}$ of formula I is independently H, $C_{1-6}$ alkyl, halogen, —$OR^{3a}$ or —$NR^{3a}R^{3a}$, $R^{3c}$ of formula I is absent or —OH.

Alternatively, $L^2$ is combined with $R^1$, $L^1$ is combined with $L^2$, $L^1$ is combined with $R^2$, two $R^1$ groups on adjacent ring atoms, or two $R^2$ groups on adjacent ring atoms are combined to form a 5-6 membered heterocycloalkyl with from 1 to 3 heteroatoms selected from N, O and S, or a 5-6 membered heteroaryl with from 1 to 3 heteroatoms selected from N, O and S, and optionally substituted with from 1 to 3 groups of H, $C_{1-6}$ alkyl or oxo.

In formula I, subscripts m and n are each an integer from 1 to 3.

Moreover, the compounds of formula I are those wherein:
(a) $L^1$ is a bond, $L^2$ is —C(O)NH—, ring B is phenyl, and at least one $R^2$ is —CN or phenyl, or
(b) at least one $R^1$ is —C(O)OH, ring A is phenyl, $L^2$ is —C(O)NH—, and $L^1$ is a bond or $C_{1-6}$ alkylene, or
(c) each of ring A and ring B is phenyl, at least one $R^1$ is —C(O)OH or combined with $L^2$, and at least one $R^2$ is H, —CN and —C(O)OH.

The compounds of formula I are such that when $R^1$ is —$CO_2H$, subscript n is 1, ring A is phenyl, $L^2$ is —C(O)NH—, $L^1$ is a bond, ring B is phenyl, subscript m is 1, and $R^2$ is phenyl, then the phenyl of $R^2$ is substituted with $C_{1-6}$ alkyl.

The compounds of formula I include the salts and isomers thereof. In this manner, the arthritis or joint injury in the mammal is ameliorated.

In some embodiments, the present invention provides a method of inducing differentiation of mesenchymal stem cells into chondrocytes, the method including contacting mesenchymal stem cells with a sufficient amount of a compound of Formula I, thereby inducing differentiation of the stem cells into chondrocytes.

In some embodiments, the present invention provides a compound having the structure:

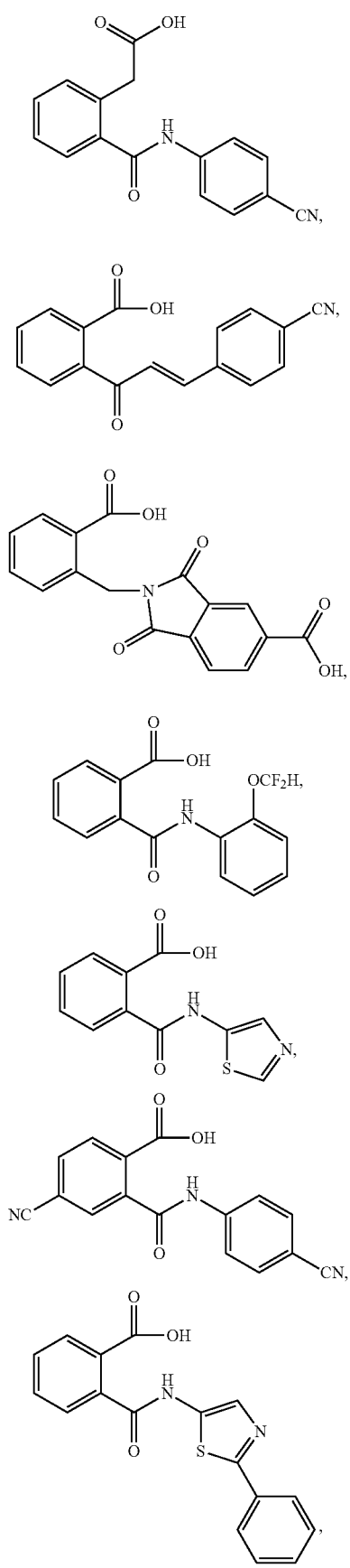
-continued
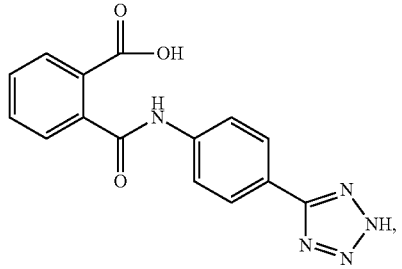
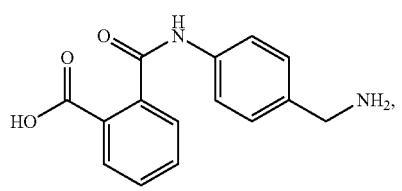
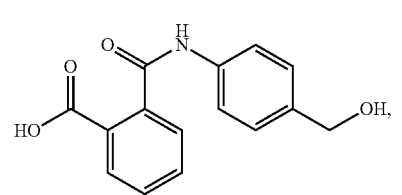
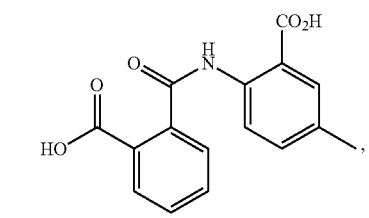
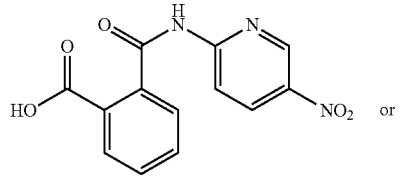 or
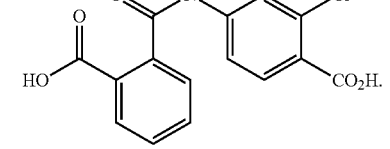
In some embodiments, the present invention provides a pharmaceutical composition including a pharmaceutically acceptable excipient and a compound having the structure:
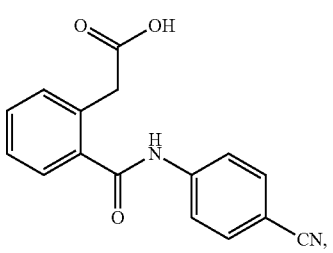

-continued

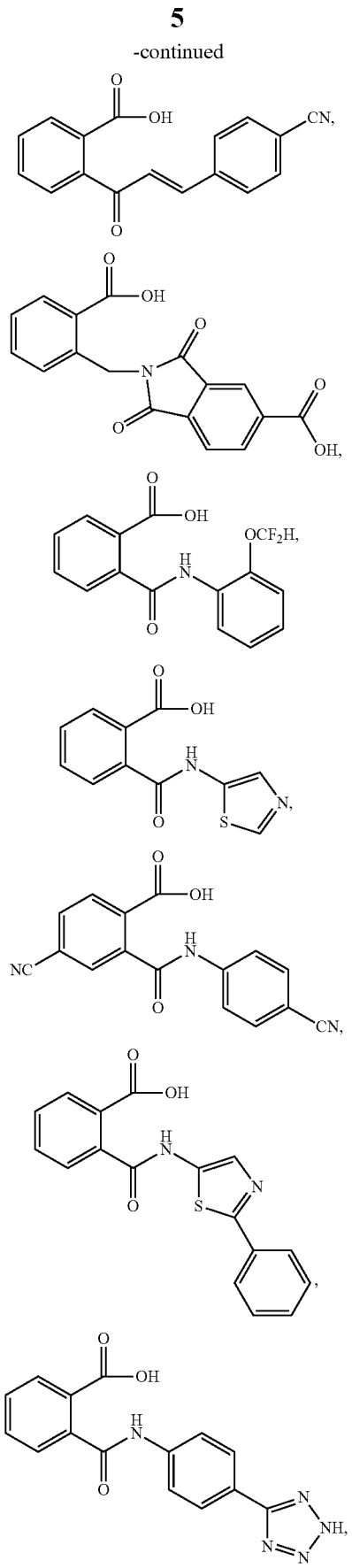

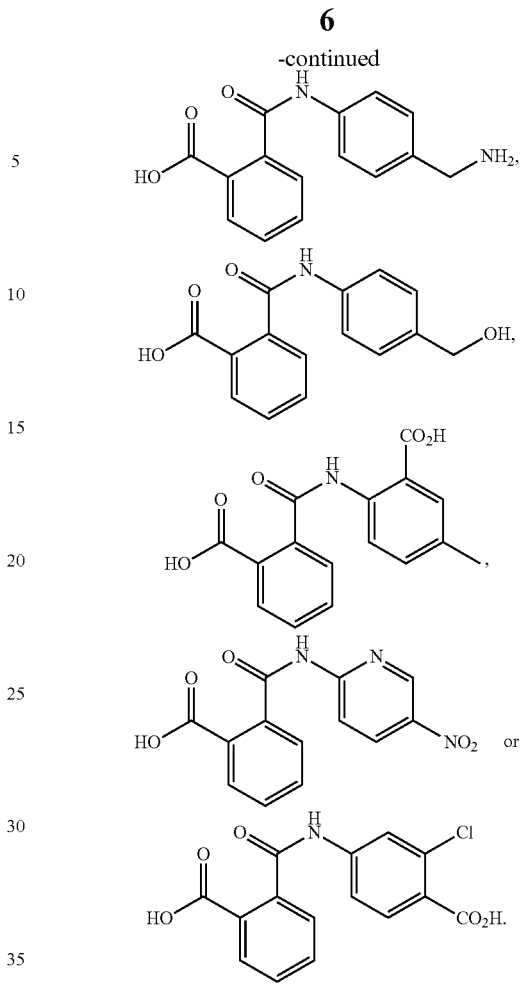

In some embodiments, the present invention provides a pharmaceutical composition formulated for intra-articular delivery, the composition including a pharmaceutically effective amount of a compound of Formula I and a pharmaceutically acceptable excipient.

DETAILED DESCRIPTION OF THE INVENTION

I. General

Figure 1:
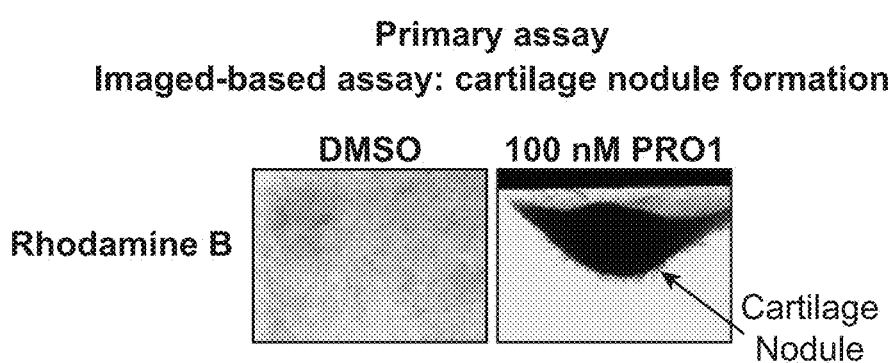
FIG. 1 shows the formation of chondrogenic nodules by human mesenchymal stem cells (hMSCs) upon treatment with inducer PRO1 (AKT), as visualized by rhodamine B-staining of cultured cells.

The present invention is based, in part, on the discovery that the compounds of the present invention stimulate chondrocyte differentiation in mesenchymal stem cells. Accordingly, the present invention provides for methods of induction of mesenchymal stem cell differentiation into chondrocytes. Further, the present invention provides for administration of compounds and compositions of the present invention to prevent or ameliorate arthritis or joint injury by administrating the compound or composition into a joint, the vertebrae, vertebral disc or systemically.

II. Definitions

"Alkyl" refers to a straight or branched, saturated, aliphatic radical having the number of carbon atoms indicated. For example, $C_1$-$C_6$ alkyl includes, but is not limited to, methyl, ethyl, propyl, isopropyl, butyl, isobutyl, sec-butyl, tert-butyl, pentyl, isopentyl, hexyl, etc. Other alkyl groups include, but are not limited to heptyl, octyl, nonyl, decyl, etc. Alkyl can include any number of carbons, such as 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 and 5-6. The alkyl group is typically monovalent, but can be divalent, such as when the alkyl group links two moieties together.

The term "lower" referred to above and hereinafter in connection with organic radicals or compounds respectively defines a compound or radical which can be branched or unbranched with up to and including 7, preferably up to and including 4 and (as unbranched) one or two carbon atoms.

"Alkylene" refers to an alkyl group, as defined above, linking at least two other groups, i.e., a divalent hydrocarbon radical. The two moieties linked to the alkylene can be linked to the same atom or different atoms of the alkylene. For instance, a straight chain alkylene can be the bivalent radical of —$(CH_2)_n$—, where n is 1, 2, 3, 4, 5 or 6. Alkylene groups include, but are not limited to, methylene, ethylene, propylene, isopropylene, butylene, isobutylene, sec-butylene, pentylene and hexylene.

"Alkoxy" refers to an alkyl group having an oxygen atom that connects the alkyl group to the point of attachment: alkyl-O—. As for alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted.

"Alkylhydroxy" refers to an alkyl group, as defined above, where at least one of the hydrogen atoms is replaced with a hydroxy group. As for the alkyl group, hydroxyalkyl groups can have any suitable number of carbon atoms, such as $C_{1-6}$. Exemplary hydroxyalkyl groups include, but are not limited to, hydroxy-methyl, hydroxy-ethyl (where the hydroxy is in the 1- or 2-position), hydroxy-propyl (where the hydroxy is in the 1-, 2- or 3-position), hydroxy-butyl (where the hydroxy is in the 1-, 2-, 3- or 4-position), hydroxy-pentyl (where the hydroxy is in the 1-, 2-, 3-, 4- or 5-position), hydroxy-hexyl (where the hydroxy is in the 1-, 2-, 3-, 4-, 5- or 6-position), 1,2-dihydroxyethyl, and the like.

"Halogen" refers to fluorine, chlorine, bromine and iodine.

"Haloalkyl" refers to alkyl as defined above where some or all of the hydrogen atoms are substituted with halogen atoms. Halogen (halo) preferably represents chloro or fluoro, but may also be bromo or iodo. For example, haloalkyl includes trifluoromethyl, fluoromethyl, 1,2,3,4,5-pentafluoro-phenyl, etc. The term "perfluoro" defines a compound or radical which has at least two available hydrogens substituted with fluorine. For example, perfluorophenyl refers to 1,2,3,4,5-pentafluorophenyl, perfluoromethane refers to 1,1,1-trifluoromethyl, and perfluoromethoxy refers to 1,1,1-trifluoromethoxy.

"Halo-alkoxy" refers to an alkoxy group having at least one halogen. Halo-alkoxy is as defined for alkoxy where some or all of the hydrogen atoms are substituted with halogen atoms. The alkoxy groups can be substituted with 1, 2, 3, or more halogens. When all the hydrogens are replaced with a halogen, for example by fluorine, the compounds are per-substituted, for example, perfluorinated. Halo-alkoxy includes, but is not limited to, trifluoromethoxy, 2,2,2,-trifluoroethoxy, perfluoroethoxy, etc.

"Alkyl amine" refers to an alkyl groups as defined within, having one or more amino groups. The amino groups can be primary, secondary or tertiary. The alkyl amine can be further substituted with a hydroxy group. Alkyl amines useful in the present invention include, but are not limited to, ethyl amine, propyl amine, isopropyl amine, ethylene diamine and ethanolamine. The amino group can link the alkyl amine to the point of attachment with the rest of the compound, be at the omega position of the alkyl group, or link together at least two carbon atoms of the alkyl group. One of skill in the art will appreciate that other alkyl amines are useful in the present invention.

"Heteroalkyl" refers to an alkyl group of any suitable length and having from 1 to 3 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heteroalkyl can include ethers, thioethers and alkyl-amines. The heteroatom portion of the heteroalkyl can replace a hydrogen of the alkyl group to form a hydroxy, thio or amino group. Alternatively, the heteroatom portion can be the connecting atom, or be inserted between two carbon atoms.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R"' and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R"' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

"Alkenyl" refers to either a straight chain or branched hydrocarbon of 2 to 6 carbon atoms, having at least one double bond. Examples of alkenyl groups include, but are not limited to, vinyl, propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can also have from 2 to 3, 2 to 4, 2 to 5, 3 to 4, 3 to 5, 3 to 6, 4 to 5, 4 to 6 and 5 to 6 carbons. The alkenyl groups is typically monovalent, but can be divalent, such as when the alkenyl group links two moieties together.

"Alkenylene" refers to an alkenyl group, as defined above, linking at least two other groups, i.e., a divalent hydrocarbon radical. The two moieties linked to the alkenylene can be linked to the same atom or different atoms of the alkenylene. Alkenylene groups include, but are not limited to, ethenylene, propenylene, isopropenylene, butenylene, isobutenylene, sec-butenylene, pentenylene and hexenylene.

"Alkynyl" refers to either a straight chain or branched hydrocarbon of 2 to 6 carbon atoms, having at least one triple bond. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can also have from 2 to 3, 2 to 4, 2 to 5, 3 to 4, 3 to 5, 3 to 6, 4 to 5, 4 to 6 and 5 to 6 carbons. The alkynyl groups is typically monovalent, but can be divalent, such as when the alkynyl group links two moieties together.

"Alkynylene" refers to an alkynyl group, as defined above, linking at least two other groups, i.e., a divalent hydrocarbon radical. The two moieties linked to the alkynylene can be linked to the same atom or different atoms of the alkynylene. Alkynylene groups include, but are not limited to, ethynylene, propynylene, isopropynylene, butynylene, sec-butynylene, pentynylene and hexynylene.

"Cycloalkyl" refers to a saturated or partially unsaturated, monocyclic, fused bicyclic or bridged polycyclic ring assembly containing from 3 to 12 ring atoms, or the number of atoms indicated Monocyclic rings include, for example, cyclopropyl, cyclobutyl, cyclopentyl, cyclohexyl, and cyclooctyl. Bicyclic and polycyclic rings include, for example, norbornane, decahydronaphthalene and adamantane. For example, C$_{3-8}$cycloalkyl includes cyclopropyl, cyclobutyl, cyclopentyl, cyclohexyl, cyclooctyl, and norbornane. Partially unsaturated cycloalkyl rings include, but are not limited to, cyclohexene and norbornene.

"Cycloalkylene" refers to a cycloalkyl group, as defined above, linking at least two other groups, i.e., a divalent hydrocarbon radical. The two moieties linked to the cycloalkylene can be linked to the same atom or different atoms of the cycloalkylene. Cycloalkylene groups include, but are not limited to, cyclopropylene, cyclobutylene, cyclopentylene, cyclohexylene, and cyclooctylene.

"Heterocycloalkyl" refers to a ring system having from 3 ring members to about 20 ring members and from 1 to about 5 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. Heterocycloalkyl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. For example, heterocycloalkyl includes, but is not limited to, tetrahydrofuranyl, tetrahydrothiophenyl, morpholino, pyrrolidinyl, pyrrolinyl, imidazolidinyl, imidazolinyl, pyrazolidinyl, pyrazolinyl, piperazinyl, piperidinyl, indolinyl, quinuclidinyl and 1,4-dioxa-8-aza-spiro[4.5]dec-8-yl.

"Heterocyclalkylene" refers to a heterocyclalkyl group, as defined above, linking at least two other groups. The two moieties linked to the heterocyclalkylene can be linked to the same atom or different atoms of the heterocyclalkylene.

"Aryl" refers to a monocyclic or fused bicyclic, tricyclic or greater, aromatic ring assembly containing 6 to 16 ring carbon atoms. For example, aryl may be phenyl, benzyl, biphenyl, or naphthyl, preferably phenyl. "Arylene" means a divalent radical derived from an aryl group. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

"Arylene" refers to an aryl group, as defined above, linking at least two other groups. The two moieties linked to the arylene are linked to different atoms of the arylene. Arylene groups include, but are not limited to, phenylene.

"Arylene-oxy" refers to an arylene group, as defined above, where one of the moieties linked to the arylene is linked through an oxygen atom. Arylene-oxy groups include, but are not limited to, phenylene-oxy.

"Heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred, 4-thiazolyl. Triazolyl is preferably 1-, 2- or 5-(1,2, 4-triazolyl). Tetrazolyl is preferably 5-tetrazolyl.

Preferably, heteroaryl is pyridyl, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono- or di-substituted.

Similarly, substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R''', —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro($C_1$-$C_4$)alkoxy, and perfluoro($C_1$-$C_4$)alkyl, in a number ranging from zero to the total number of open valences on the aromatic ring system; and where R', R" and R''' are independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

"Alkyl-aryl" refers to a radical having an alkyl component and an aryl component, where the alkyl component links the aryl component to the point of attachment. The alkyl component is as defined above, except that the alkyl component is at least divalent in order to link to the aryl component and to the point of attachment. In some instances, the alkyl component can be absent. The aryl component is as defined above. Examples of alkyl-aryl groups include, but are not limited to, benzyl.

"Alkyl-heteroaryl" refers to a radical having an alkyl component and a heteroaryl component, where the alkyl component links the heteroaryl component to the point of attachment. The alkyl component is as defined above, except that the alkyl component is at least divalent in order to link to the heteroaryl component and to the point of attachment. In some instances, the alkyl component can be absent. The heteroaryl component is as defined within. Examples of alkyl-heteroaryl include methylene-pyridyl, among others.

"Alkyl-cycloalkyl" refers to a radical having an alkyl component and a cycloalkyl component, where the alkyl component links the cycloalkyl component to the point of attachment. The alkyl component is as defined above, except that the alkyl component is at least divalent in order to link to the cycloalkyl component and to the point of attachment. In some instances, the alkyl component can be absent. The cycloalkyl component is as defined within. Examples of alkyl-cycloalkyl include methylene-cyclohexane, among others.

"Alkyl-heterocycloalkyl" refers to a radical having an alkyl component and a heterocycloalkyl component, where the alkyl component links the heterocycloalkyl component to the point of attachment. The alkyl component is as defined above, except that the alkyl component is at least divalent in order to link to the heterocycloalkyl component and to the point of attachment. In some instances, the alkyl component can be absent. The heterocycloalkyl component is as defined above. Examples of alkyl-heterocycloalkyl include methylene-piperidinyl, among others.

"Heteroaryl-aryl" refers to a radical having a heteroaryl component and an aryl component, where the heteroaryl component links the aryl component to the point of attachment on the compound of the present invention. The heteroaryl component is as defined above, except that the heteroaryl component is at least divalent to link to the aryl component and to the point of attachment on the compound of the present invention. The aryl component is as defined above.

"Linker" refers to a chemical moiety that links the compound of the present invention to a biological material that targets a specific type of cell, such as a cancer cell, other type of diseased cell, or a normal cell type. Linkers useful in the present invention can be up to 30 carbon atoms in length. The types of bonds used to link the linker to the compound and biological molecule of the present invention include, but are not limited to, amides, amines, esters, carbamates, ureas, thioethers, thiocarbamates, thiocarbonate and thioureas. One of skill in the art will appreciate that other types of bonds are useful in the present invention.

"Pharmaceutically acceptable excipient" refers to a substance that aids the administration of an active agent to and absorption by a subject. Pharmaceutical excipients useful in the present invention include, but are not limited to, binders, fillers, disintegrants, lubricants, coatings, sweeteners, flavors and colors. One of skill in the art will recognize that other pharmaceutical excipients are useful in the present invention.

"Contacting" refers to the process of bringing into contact at least two distinct species such that they can react. It should be appreciated, however, the resulting reaction product can be produced directly from a reaction between the added reagents or from an intermediate from one or more of the added reagents which can be produced in the reaction mixture.

"Therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Subject" refers to animals such as mammals, including, but not limited to, primates (e.g., humans), domestic and farm animals, and zoo, sports or pet animals, such as cattle (e.g. cows), horses, dogs, sheep, pigs, rabbits, goats, cats, mice, etc. In certain embodiments, the subject is a human.

"Administering" refers to administration to a specific joint.

"Treat", "treating", "treatment" plus "ameliorate" and "ameliorating" refer to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

"At increased risk for" refers to a patient having an above average risk for a particular disease or condition, wherein the increased risk is a result of existing health conditions, genetic or family history, existing or prior injuries, repetitive motion actions or conditions.

"Chondrocytes" refers to cartilage cells. Chondrocytes produce and maintain the cartilaginous matrix which is composed of collagen and proteoglycans. Chondrocytes are derived from the differentiation of mesenchymal stem cells (MSCs). MSCs are multipotent stem cells that can differentiate into several different types of cells including, but not limited to, osteoblasts, chondrocytes and adipocytes. Differentiation is the process a specialized cell type is formed from a less specialized cell type, for example, a chondrocyte from a MSC.

"Hyaluronic acid" refers to derivatives of hyaluronic acid that include esters of hyaluronic acid, salts of hyaluronic acid and also includes the term hyaluronan. The designation also includes both low and high molecular weight forms of hyaluronans and crosslinked hyaluronans or hylans. Examples of such hyaluronans are Synvisc™ (Genzyme Corp. Cambridge, Mass.), ORTHOVISC™ (Anika Therapeutics, Woburn, Mass.), and HYALGAN™ (Sanofi-Synthelabo Inc., Malvern, Pa.).

III. Compounds

In some embodiments, the present invention provides compounds of formula I:

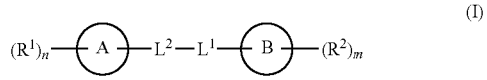

(I)

In formula I, each of ring A and ring B are independently cycloalkyl, aryl or heteroaryl.

In formula I, each $R^1$ and $R^2$ is independently H, $C_{1-6}$ alkyl, $C_{2-6}$ alkenyl, $C_{2-6}$ alkynyl, $C_{1-6}$ alkoxy, $C_{1-6}$ heteroalkyl, halogen, $C_{1-6}$ haloalkyl, $C_{1-6}$ haloalkoxy, $C_{1-6}$ alkyl-CN, $C_{1-6}$ alkylhydroxy, —$OR^{2a}$, —$NR^{2b}R^{2d}$, $C_{1-6}$ alkyl-$NR^{2b}R^{2d}$, —$C(O)R^{1a}$, —$C(O)R^{2d}$, —$C(O)OR^{2a}$, $C_{1-6}$ alkyl-$C(O)OR^{2b}$, —$OC(O)R^{2b}$, —$OC(O)OR^{2b}$, —$C(O)NR^{2a}R^{2b}$, —$C(O)N(OH)R^{2b}$, —$NR^{2b}C(O)R^{2c}$, $C_{1-6}$ alkyl-$NR^{2b}C(O)R^{2c}$, —$NR^{2b}C(O)OR^{2c}$, $C_{1-6}$ alkyl-$NR^{2b}C(O)OR^{2c}$, —$OC(O)NR^{2b}R^{2c}$, —$NR^{2b}C(O)NR^{2b}R^{2c}$, —$NR^{2b}C(NR^{2b})NR^{2b}R^{2c}$, —$C(O)NR^{2b}C(O)R^{2b}$, $C_{1-6}$ alkyl-$NR^{2b}C(O)NR^{2b}R^{2c}$, —$SR^{2a}$, —$SO_2R^{2b}$, —$SO_2OR^{2b}$, —$SO_2NR^{2b}R^{2d}$, —$NR^{2b}SO_2R^{2b}$, —$P(O)(OR^{2b})_2$, —$B(OR^{2b})$, —CN, —$NO_2$, —$N_3$, heterocycloalkyl, aryl, heteroaryl, $C_{1-6}$ alkyl-heterocycloalkyl, $C_{1-6}$ alkyl-aryl, $C_{1-6}$ alkyl-O-aryl, $C_{1-6}$ alkyl-heteroaryl, or heteroaryl-aryl, and wherein the heterocycloalkyl, aryl and heteroaryl groups are optionally substituted with 1 to 2 $R^{2a}$ groups.

In formula I, $R^{1a}$ is —$OR^{1b}$ or —$NR^{1b}R^{1c}$; $R^{1b}$ and $R^{1c}$ are each independently H, $C_{1-6}$ alkyl, $C_{2-6}$ alkenyl, $C_{2-6}$ alkynyl, cycloalkyl, heterocycloalkyl, aryl, heteroaryl, $C_{1-6}$ alkyl-aryl, or $C_{1-6}$ alkyl-heteroaryl, wherein the cycloalkyl, heterocycloalkyl, aryl and heteroaryl groups are optionally substituted with from 1 to 4 $R^{1d}$ groups; and each $R^{1d}$ is independently H, $C_{1-6}$ alkyl, $C_{1-6}$ alkoxy, or —$NO_2$.

In formula I, each $R^{2a}$ is independently H, $C_{2-6}$ alkenyl, $C_{2-6}$ alkynyl, cycloalkyl, heterocycloalkyl, aryl, heteroaryl, $C_{1-6}$ alkyl-cycloalkyl, $C_{1-6}$ alkyl-heterocycloalkyl, $C_{1-6}$ alkyl-aryl or $C_{1-6}$ alkyl-heteroaryl, optionally substituted with 1 to 2 $R^{2b}$ groups; each $R^{2b}$ and $R^{2c}$ is independently H, or $C_{1-6}$ alkyl; and each $R^{2d}$ is independently H, $C_{1-6}$ alkyl, cycloalkyl, heterocycloalkyl, aryl, heteroaryl, $C_{1-6}$ alkyl-cycloalkyl, $C_{1-6}$ alkyl-heterocycloalkyl, $C_{1-6}$ alkyl-aryl or $C_{1-6}$ alkyl-heteroaryl, each optionally substituted with 1 to 2 $R^{2b}$ groups.

In formula I, each of $L^1$ and $L^2$ are independently $L^1$ and $L^2$ are independently a bond, $C_{1-6}$ alkylene, $C_{2-6}$ alkenylene, $C_{1-6}$ alkylene-O—, —O—$C_{1-6}$ alkylene, $C_{1-6}$ alkylene-$NR^{3a}$—, —$NR^{3a}$—$C_{1-6}$ alkylene, —C(O)—, $C_{1-6}$ alkylene-C(O)—, —C(O)—$C_{1-6}$ alkylene-NH—, —NH—$C_{1-6}$ alkylene-C(O)—, —C(O)NH—, —NHC(O)—, $C_{1-6}$ alkylene-NHC(O)—, —$SO_2NH$—, —$NHSO_2$—, —NHC(O)NH—, cycloalkylene, —N=N—, or —$C(R^{3a})$=$N(R^{3c})$—, wherein the alkylene group is optionally substituted with from 1-4 $R^{3b}$ groups. $R^{3a}$ of formula I is H or $C_{1-6}$ alkyl. Each $R^{3b}$ of formula I is independently H, $C_{1-6}$ alkyl, halogen, —$OR^{3a}$ or —$NR^{3a}R^{3a}$. $R^{3c}$ of formula I is absent or —OH.

Alternatively, $L^2$ is combined with $R^1$, $L^1$ is combined with $L^2$, $L^1$ is combined with $R^2$, two $R^1$ groups on adjacent ring atoms, or two $R^2$ groups on adjacent ring atoms are combined to form a 5-6 membered heterocycloalkyl with from 1 to 3 heteroatoms selected from N, O and S, or a 5-6 membered heteroaryl with from 1 to 3 heteroatoms selected from N, O and S, and optionally substituted with from 1 to 3 groups of H, $C_{1-6}$ alkyl or oxo.

In formula I, subscripts m and n are each an integer from 1 to 3.

Moreover, the compounds of formula I are those wherein:
(a) $L^1$ is a bond, $L^2$ is —C(O)NH—, ring B is phenyl, and at least one $R^2$ is —CN or phenyl, or
(b) at least one $R^1$ is —C(O)OH, ring A is phenyl, $L^2$ is —C(O)NH—, and $L^1$ is a bond or $C_{1-6}$ alkylene, or
(c) each of ring A and ring B is phenyl, at least one $R^1$ is —C(O)OH or combined with $L^2$, and at least one $R^2$ is H, —CN and —C(O)OH.

The compounds of formula I are such that when $R^1$ is —$CO_2H$, subscript n is 1, ring A is phenyl, $L^2$ is —C(O)NH—, $L^1$ is a bond, ring B is phenyl, subscript m is 1, and $R^2$ is phenyl, then the phenyl of $R^2$ is substituted with $C_{1-6}$ alkyl.

The compounds of formula I include the salts and isomers thereof.

In some embodiments, the compounds of formula I are those wherein:

(a) $L^1$ is a bond, $L^2$ is —C(O)NH—, ring B is phenyl, $R^2$ is —CN or phenyl, and subscript m is 1, or (b) $R^1$ is —C(O)OH, subscript n is 1, ring A is phenyl, $L^2$ is —C(O)NH—, and $L^1$ is a bond or —$CH_2$—, or (c) each of ring A and ring B is phenyl, $R^1$ is —C(O)OH or combined with $L^2$, subscript n is 1, and at least one $R^2$ is selected from the group consisting of H, —CN and —$CO_2H$.

In some embodiments, the compounds of the present invention have the structure:

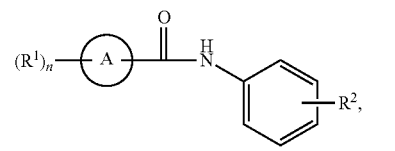
(Ia)

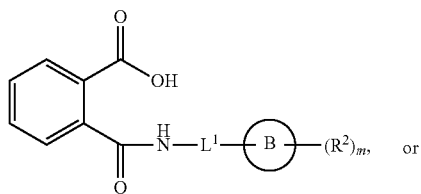
(Ib)

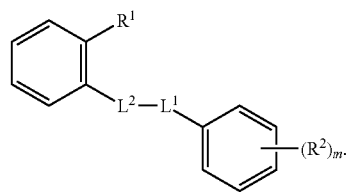
(Ic)

The compounds of the present invention can also have any of the following structures:

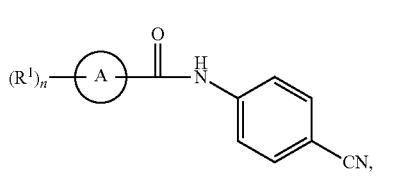
(Ia1)

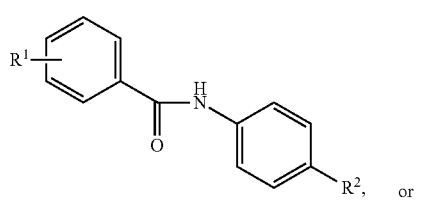
(Ia2)

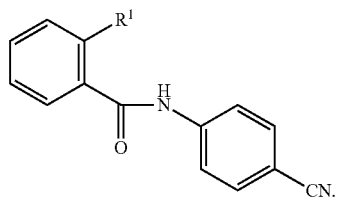
(Ia3)

In some embodiments, the compounds of formulas I, Ia, Ia1, Ia2, Ia3 and Ic are those wherein each $R^1$ is independently $C_{2-6}$ alkenyl, $C_{2-6}$ alkynyl, $C_{1-6}$ alkoxy, $C_{1-6}$ heteroalkyl, halogen, $C_{1-6}$ haloalkyl, $C_{1-6}$ haloalkoxy, $C_{1-6}$ alkyl-CN, $C_{1-6}$ alkylhydroxy, —$OR^{2a}$, —$NR^{2b}R^{2d}$, $C_{1-6}$ alkyl-$NR^{2b}R^{2d}$, —$C(O)R^{1a}$, —$C(O)R^{2d}$, —$C(O)OR^{2a}$, $C_{1-6}$ alkyl-$C(O)OR^{2b}$, —$OC(O)R^{2b}$, —$OC(O)OR^{2b}$, —$C(O)NR^{2a}R^{2b}$, —$C(O)N(OH)R^{2b}$, —$NR^{2b}C(O)R^{2c}$, $C_{1-6}$ alkyl-$NR^{2b}C(O)R^{2c}$, —$NR^{2b}C(O)OR^{2c}$, $C_{1-6}$ alkyl-$NR^{2b}C(O)OR^{2c}$, —$OC(O)NR^{2b}R^{2c}$, —$NR^{2b}C(O)NR^{2b}R^{2c}$, —$NR^{2b}C(NR^{2b})NR^{2b}R^{2c}$, —$C(O)NR^{2b}C(O)R^{2b}$, $C_{1-6}$ alkyl-$NR^{2b}C(O)NR^{2b}R^{2c}$, —$SR^{2a}$, —$SO_2R^{2b}$, —$SO_2OR^{2b}$, —$SO_2NR^{2b}R^{2d}$, —$NR^{2b}SO_2R^{2b}$, —$P(O)(OR^{2b})_2$, —$B(OR^{2b})$, —CN, —$NO_2$, —$N_3$, heterocycloalkyl, aryl, heteroaryl, $C_{1-6}$ alkyl-heterocycloalkyl, $C_{1-6}$ alkyl-aryl, $C_{1-6}$ alkyl-O-aryl, $C_{1-6}$ alkyl-heteroaryl, or heteroaryl-aryl, and wherein the heterocycloalkyl, aryl and heteroaryl groups are optionally substituted with 1 to 2 $R^{2a}$ groups. In some embodiments, the compounds of formulas I, Ia, Ia1, Ia2, Ia3 and Ic are those wherein each $R^1$ is independently —C(O)$R^{2d}$, —C(O)$OR^{2b}$, $C_{1-6}$ alkyl-C(O)$OR^{2b}$, —$NR^{2b}C(O)OR^{2c}$, —$NR^{2b}C(O)NR^{2b}R^{2c}$, —$SO_2OR^{2b}$, —$SO_2NR^{2b}R^{2d}$, —$NR^{2b}SO_2R^{2b}$, or —CN. In some embodiments, the compounds of formulas I, Ia, Ia1, Ia2, Ia3 and Ic are those wherein each $R^1$ is independently —$CH_2C(O)OH$, —C(O)Me, —NHC(O)$NH_2$, —NHC(O)OMe, —$NHSO_2Me$, —$SO_2NH_2$, —$SO_2NHMe$, —$SO_3H$, —C(O)OH, or —CN. Moreover, each of $R^{2a}$, $R^{2b}$, $R^{2c}$ and $R^{2d}$ are independently H or $C_{1-6}$ alkyl. In the compounds of formulas I, Ia, Ia1, Ia2, Ia3 and Ic, the compounds are those wherein when ring A is phenyl and at least one $R^1$ is —C(O)OH, then subscript n is 2 or 3.

In some embodiments, the compounds of formulas I, Ia, Ia2, Ib and Ic are those wherein each $R^2$ is independently H, $C_{1-6}$ haloalkoxy, $C_{1-6}$ alkyl-$NR^{2b}R^{2d}$, —C(O)$OR^{2b}$, —C(O)N(OH)$R^{2b}$, $C_{1-6}$ alkyl-$NR^{2b}C(O)OR^{2c}$, $C_{1-6}$ alkyl-$NR^{2b}C(O)NR^{2b}R^{2c}$, —$SO_2OR^{2b}$, —$PO_3H$, —CN, aryl, heteroaryl, or $C_{1-6}$ alkyl-O-aryl. In some embodiments, the compounds of formulas I, Ia, Ia2, Ib and Ic are those wherein each $R^2$ is independently H, —$CH_2NHCONH_2$, —$CH_2NHCOOMe$, —$CH_2NHMe$, —$CH_2OPh$, 2-CN, 4-CN, —C(O)OH, —CONHOH, —$OCF_2H$, —$PO_3H$, —$SO_3H$, phenyl, pyridyl, imidazole or tetrazole. In some embodiments, the compounds of formulas I, Ia, Ia2, Ib and Ic are those wherein each $R^2$ is independently $C_{1-6}$ alkyl, halogen, $C_{1-6}$ alkylhydroxy, $C_{1-6}$ alkyl-$NR^{2b}R^{2d}$, —C(O)$R^{2d}$, —C(O)$OR^{2b}$, —C(O)$NR^{2b}R^{2c}$, —$SO_2NR^{2b}R^{2d}$, —CN, -heterocycloalkyl, or aryl, wherein the aryl groups are optionally substituted with halogen. In some embodiments, the compounds of formulas I, Ia, Ia2, Ib and Ic are those wherein each $R^2$ is H, Me, —Cl, —$CH_2OH$, —$CH_2CH_2OH$, —$CH_2NH_2$, —C(O)Me, —C(O)OH, —C(O)$NH_2$, —CN, morpoholine, 3,4-difluorophenyl or —$SO_2NH_2$. Alternatively, in the compounds of formulas I, Ia2, Ib and Ic, two $R^2$ groups on adjacent ring atoms can be combined to form a 5-membered heterocycloalkyl. Alternatively, the compounds of formulas I, Ia, Ia2, Ib and Ic are those were two $R^2$ groups on adjacent ring atoms are combined to form a 1,3-dioxole or 1-methylpyrrolidine-2,5-dione.

In some embodiments, the compounds of the present invention have the structure:

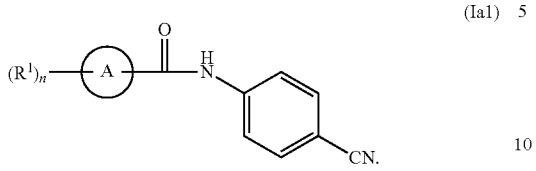

(Ia1)

In the compounds of formula Ia1, each $R^1$ is independently $C_{2-6}$ alkenyl, $C_{2-6}$ alkynyl, $C_{1-6}$ alkoxy, $C_{1-6}$ heteroalkyl, halogen, $C_{1-6}$ haloalkyl, $C_{1-6}$ haloalkoxy, $C_{1-6}$ alkyl-CN, $C_{1-6}$ alkylhydroxy, —$OR^{2a}$, —$NR^{2b}R^{2d}$, $C_{1-6}$ alkyl-$NR^{2b}R^{2d}$, —$C(O)R^{1a}$, —$C(O)R^{2d}$, —$C(O)OR^{2a}$, $C_{1-6}$ alkyl-$C(O)OR^{2b}$, —$OC(O)R^{2b}$, —$OC(O)OR^{2b}$, —$C(O)NR^{2a}R^{2b}$, —$C(O)N(OH)R^{2b}$, —$NR^{2b}C(O)R^{2c}$, $C_{1-6}$ alkyl-$NR^{2b}C(O)R^{2c}$, —$NR^{2b}C(O)OR^{2c}$, $C_{1-6}$ alkyl-$NR^{2b}C(O)OR^{2c}$, —$OC(O)NR^{2b}R^{2c}$, —$NR^{2b}C(O)NR^{2b}R^{2c}$, —$NR^{2b}C(NR^{2b})NR^{2b}R^{2c}$, —$C(O)NR^{2b}C(O)R^{2b}$, $C_{1-6}$ alkyl-$NR^{2b}C(O)NR^{2b}R^{2c}$, —$SR^{2a}$, —$SO_2R^{2b}$, —$SO_2OR^{2b}$, —$SO_2NR^{2b}R^{2d}$, —$NR^{2b}SO_2R^{2b}$, —$P(O)(OR^{2b})_2$, —$B(OR^{2b})$, —CN, —$NO_2$, —$N_3$, heterocycloalkyl, aryl, heteroaryl, $C_{1-6}$ alkyl-heterocycloalkyl, $C_{1-6}$ alkyl-aryl, $C_{1-6}$ alkyl-O-aryl, $C_{1-6}$ alkyl-heteroaryl, or heteroaryl-aryl, and wherein the heterocycloalkyl, aryl and heteroaryl groups are optionally substituted with 1 to 2 $R^{2a}$ groups. Moreover, each of $R^{2a}$, $R^{2b}$, $R^{2c}$ and $R^{2d}$ are independently H or $C_{1-6}$ alkyl.

In the compounds of formula Ia1, ring A is phenyl, biphenyl or pyridyl.

In formula Ia1, the compounds are those wherein when ring A is phenyl and at least one $R^1$ is —C(O)OH, then subscript n is 2 or 3.

In some embodiments, the compounds of formula Ia1 are those wherein each $R^1$ is independently —$C(O)R^{2d}$, —$C(O)OR^{2b}$, $C_{1-6}$ alkyl-$C(O)OR^{2b}$, —$NR^{2b}C(O)OR^{2c}$, —$NR^{2b}C(O)NR^{2b}R^{2c}$, —$SO_2OR^{2b}$, —$SO_2NR^{2b}R^{2d}$, —$NR^{2b}SO_2R^{2b}$, or —CN.

In some embodiments, the compounds of formula Ia1 are those wherein each $R^1$ is independently —$CH_2C(O)OH$, —C(O)Me, —$NHC(O)NH_2$, —NHC(O)OMe, —$NHSO_2Me$, —$SO_2NH_2$, —$SO_2NHMe$, —$SO_3H$, —C(O)OH, or —CN.

In some embodiments, the compounds of formula Ia1 are those wherein ring A is phenyl, and subscript n is 1. In other embodiments, the compounds of formula Ia1 are those wherein ring A is biphenyl or pyridyl, or subscript n is 2. In some other embodiments, the compounds of formula Ia1 are those wherein ring A is biphenyl or pyridyl. In still other embodiments, the compounds of formula Ia1 are those wherein subscript n is 2.

In some embodiments, the compounds of the present invention have the structure:

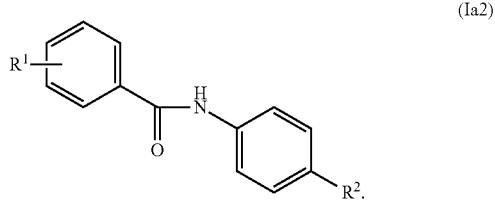

(Ia2)

In the compounds of formula Ia2, $R^1$ is $C_{1-6}$ alkyl or —$C(O)OR^{2b}$, and $R^2$ is —CN or Ph.

In some embodiments, the compounds of the present invention have the structure:

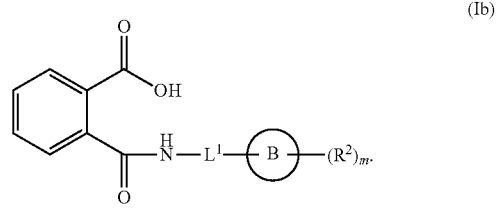

(Ib)

In the compounds of formula Ib, each $R^2$ is independently H, $C_{1-6}$ haloalkoxy, $C_{1-6}$ alkyl-$NR^{2b}R^{2d}$, —$C(O)OR^{2b}$, —$C(O)N(OH)R^{2b}$, $C_{1-6}$ alkyl-$NR^{2b}C(O)OR^{2c}$, $C_{1-6}$ alkyl-$NR^{2b}C(O)NR^{2b}R^{2c}$, —$SO_2OR^{2b}$, —$PO_3H$, —CN, aryl, heteroaryl, or $C_{1-6}$ alkyl-O-aryl. Ring B of formula Ib is cyclohexyl, phenyl, imidazole, oxazole, thiazole, pyrimidine, or pyrazine. $L^1$ of formula Ib is a bond or —$CH_2$—.

The compounds of formula Ib are those wherein when $R^2$ is $C_{1-6}$ alkyl-$NR^{2b}R^{2d}$, then one of $R^{2b}$ and $R^{2d}$ is $C_{1-6}$ alkyl; when $R^2$ is —C(O)OH, then $L^1$ is —$CH_2$— or ring B is cyclohexyl, or both; when $R^2$ is —CN, then $L^1$ is —$CH_2$— or ring B is cyclohexyl, or both; and when ring B is 2-thiazole, $R^2$ is unsubstituted phenyl.

In some embodiments, the compounds of formula Ib are those wherein each $R^2$ is independently H, —$CH_2NHCONH_2$, —$CH_2NHCOOMe$, —$CH_2NHMe$, —$CH_2OPh$, 2-CN, 4-CN, —C(O)OH, —CONHOH, —$OCF2H$, —$PO_3H$, —$SO_3H$, phenyl, pyridyl, imidazole or tetrazole.

In some embodiments, the compounds of formula Ib are those wherein each $R^2$ is independently $C_{1-6}$ alkyl, halogen, $C_{1-6}$ alkylhydroxy, $C_{1-6}$ alkyl-$NR^{2b}R^{2d}$, —$C(O)R^{2d}$, —$C(O)OR^{2b}$, —$C(O)NR^{2b}R^{2c}$, —$SO_2NR^{2b}R^{2d}$, —CN, heterocycloalkyl, or aryl, wherein the aryl groups are optionally substituted with halogen. Alternatively, two $R^2$ groups on adjacent ring atoms of formula Ib can be combined to form a 5-membered heterocycloalkyl. Ring B of formula Ib is phenyl, thiazole or pyridyl. $L^1$ of formula Ib is a bond or —$CH_2$—. Moreover, the compounds of formula Ib are those wherein when $R^2$ is $C_{1-6}$ alkyl-$NR^{2b}R^{2d}$, then both of $R^{2b}$ and $R^{2d}$ are H; when $R^2$ is —C(O)OH, then $L^1$ is a bond and ring B is phenyl; when $R^2$ is —CN, then $L^1$ is a bond and ring B is phenyl; and when ring B is 2-thiazole, then $R^2$ is substituted phenyl.

In some embodiments, the compounds of formula Ib are those wherein each $R^2$ is H, Me, —Cl, —$CH_2OH$, —$CH_2CH_2OH$, —$CH_2NH_2$, —C(O)Me, —C(O)OH, —$C(O)NH_2$, —CN, morpholine, 3,4-difluorophenyl or —$SO_2NH_2$. Alternatively, two $R^2$ groups on adjacent ring atoms are combined to form a 1,3-dioxole or 1-methylpyrrolidine-2,5-dione.

In some embodiments, the compounds of the present invention have the structure:

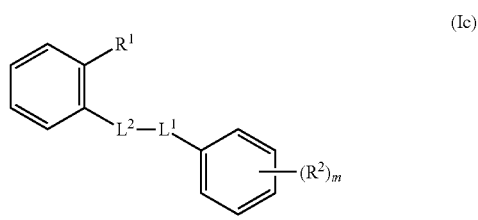

(Ic)

In the compounds of formula Ic, $R^1$ is —C(O)OH. Each $R^2$ of formula Ic is independently —CN or —C(O)OH. Each of $L^1$ and $L^2$ in formula IC are independently a bond, $C_{1-6}$ alkylene, $C_{2-6}$ alkenylene, —C(O)—, $C_{1-6}$ alkylene-C(O)—, —C(O)—$C_{1-6}$ alkylene-NH—, —NH—$C_{1-6}$ alkylene-C(O)—, —NHC(O)—, —SO$_2$NH—, —NHSO$_2$—, or —NHC(O)NH—, wherein at least one of $L^1$ and $L^2$ is —C(O)—, $C_{1-6}$ alkylene-C(O)—, —C(O)—$C_{1-6}$ alkylene-NH—, —NH—$C_{1-6}$ alkylene-C(O)—, —NHC(O)—, —SO$_2$NH—, —NHSO$_2$—, or —NHC(O)NH—. Alternatively, $L^2$ is combined with $R^1$, or $L^1$ is combined with $R^2$, to form a 5-6 membered heterocycloalkyl with from 1 to 3 heteroatoms selected from N, O and S, or a 5-6 membered heteroaryl with from 1 to 3 heteroatoms selected from N, O and S.

In some embodiments, the compounds of the present invention have the structure:

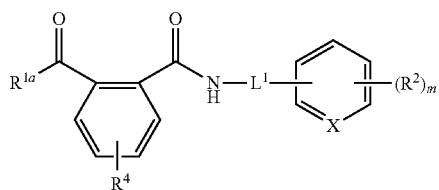

(Id)

In the compounds of formula Id, $R^{1a}$ is —OR$^{1b}$ or —NR$^{1b}$R$^{1c}$. $R^{1b}$ and $R^{1c}$ of formula Id are each independently H, $C_{1-6}$ alkyl, $C_{2-6}$ alkenyl, $C_{2-6}$ alkynyl, cycloalkyl, heterocycloalkyl, aryl, heteroaryl, $C_{1-6}$ alkyl-aryl, and $C_{1-6}$ alkyl-heteroaryl, wherein the cycloalkyl, heterocycloalkyl, aryl or heteroaryl groups are optionally substituted with from 1 to 4 $R^{1d}$ groups. Each $R^{1d}$ of formula ID is independently H, $C_{1-6}$ alkyl, $C_{1-6}$ alkoxy, or —NO$_2$.

In the compounds of formula Id, each $R^2$ is independently $C_{1-6}$ alkyl, $C_{1-6}$ alkoxy, halogen, $C_{1-6}$ haloalkyl, $C_{1-6}$ haloalkoxy, $C_{1-6}$ alkylamine, $C_{1-6}$ alkyl-CN, $C_{1-6}$ alkyl-OH, heterocycloalkyl, aryl, heteroaryl, $C_{1-6}$ alkyl-aryl, $C_{1-6}$ alkyl-heteroaryl, heteroaryl-aryl, —OR$^{2a}$, —NR$^{2b}$R$^{2d}$, —C(O)R$^{2d}$, —C(O)OR$^{2b}$, —OC(O)R$^{2b}$, —C(O)NR$^{2b}$R$^{2c}$, —NR$^{2b}$C(O)R$^{2c}$, —NR$^{2b}$C(O)OR$^{2c}$, —OC(O)NR$^{2b}$R$^{2c}$, —SO$_2$R$^{2a}$, —SO$_2$NR$^{2b}$R$^{2d}$, —CN, —NO$_2$, or —N$_3$, wherein the heterocycloalkyl, aryl and heteroaryl groups are optionally substituted with 1 to 2 $R^{2b}$ groups. Alternatively, two $R^2$ groups on adjacent ring atoms are combined to form a 5 to 6 membered heterocyclic ring having from 1 to 3 heteroatoms each independently N, O and S, and optionally substituted with from 1 to 3 groups of H, $C_{1-6}$ alkyl or oxo.

In the compounds of formula Id, each $R^{2a}$ is independently H, $C_{2-6}$ alkenyl, $C_{2-6}$ alkynyl, cycloalkyl, heterocycloalkyl, aryl, heteroaryl, $C_{1-6}$ alkyl-cycloalkyl, $C_{1-6}$ alkyl-heterocycloalkyl, $C_{1-6}$ alkyl-aryl or $C_{1-6}$ alkyl-heteroaryl, optionally substituted with 1 to 2 $R^{2b}$ groups. Each $R^{2b}$ and $R^{2c}$ of formula Id is independently H or $C_{1-6}$ alkyl. Each $R^{2d}$ of formula Id is independently H, $C_{1-6}$ alkyl, cycloalkyl, heterocycloalkyl, aryl, heteroaryl, $C_{1-6}$ alkyl-cycloalkyl, $C_{1-6}$ alkyl-heterocycloalkyl, $C_{1-6}$ alkyl-aryl or $C_{1-6}$ alkyl-heteroaryl, each optionally substituted with 1 to 2 $R^{2b}$ groups.

In the compounds of formula Id, $R^4$ is independently $C_{1-6}$ alkyl, halogen, $C_{1-6}$ haloalkyl, $C_{1-6}$ alkoxy, $C_{1-6}$ haloalkoxy, OH, —CO$_2$H, or —NO$_2$.

In the compounds of formula Id, $L^1$ is a bond, $C_{1-6}$ alkylene, —C(O)—, —$C_{1-6}$ alkylene-NH—, —$C_{1-6}$ alkylene-NHC(O)—, or heteroarylene.

In the compounds of formula Id, X is —CH— or —N—.

In some embodiments, the compounds of formula Id are those wherein each $R^2$ is independently $C_{1-6}$ alkyl, $C_{1-6}$ alkoxy, halogen, $C_{1-6}$ haloalkyl, $C_{1-6}$ alkyl-CN, $C_{1-6}$ alkyl-OH, heterocycloalkyl, aryl, heteroaryl, $C_{1-6}$ alkyl-aryl, $C_{1-6}$ alkyl-heteroaryl, heteroaryl-aryl, —OR$^{2a}$, —NR$^{2b}$R$^{2d}$, —C(O)R$^{2d}$, —OC(O)R$^{2b}$, —C(O)NR$^{2b}$R$^{2c}$, —NR$^{2b}$C(O)R$^{2c}$, —NR$^{2b}$C(O)OR$^{2c}$, —OC(O)NR$^{2b}$R$^{2c}$, —SO$_2$R$^{2a}$, —SO$_2$NR$^{2b}$R$^{2d}$, —CN, —NO$_2$, or —N$_3$, wherein the heterocycloalkyl, and aryl groups are optionally substituted with 1 to 2 $R^{2b}$ groups, such that when $R^2$ is —CN, then subscript m is 1, $R^{1a}$ is OH, $R^4$ is H, and $L^1$ is a bond.

In some embodiments, the compounds of formula Id are those wherein each $R^2$ is independently $C_{1-6}$ alkyl, halogen, $C_{1-6}$ haloalkyl, $C_{1-6}$ alkyl-CN, $C_{1-6}$ alkyl-OH, heterocycloalkyl, aryl, heteroaryl, $C_{1-6}$ alkyl-aryl, $C_{1-6}$ alkyl-heteroaryl, heteroaryl-aryl, —OR$^{2a}$, —NR$^{2b}$R$^{2d}$, —C(O)R$^{2d}$, —OC(O)R$^{2b}$, —C(O)NR$^{2b}$R$^{2c}$, —NR$^{2b}$C(O)R$^{2c}$, —NR$^{2b}$C(O)OR$^{2c}$, —OC(O)NR$^{2b}$R$^{2c}$, —SO$_2$R$^{2a}$, —SO$_2$NR$^{2b}$R$^{2d}$, —CN, —NO$_2$, and —N$_3$, wherein the heterocycloalkyl, and aryl groups are optionally substituted with 1 to 2 $R^{2b}$ groups; and $L^1$ is a bond. The compounds of formula Id are those wherein when $R^2$ is —CN, then subscript m is 1, $R^{1a}$ is OH, $R^4$ is H, and $L^1$ is a bond. In other embodiments, when two $R^2$ groups are present on adjacent ring atoms, the $R^2$ groups are not combined.

In some embodiments, the compound of the present invention has the structure:

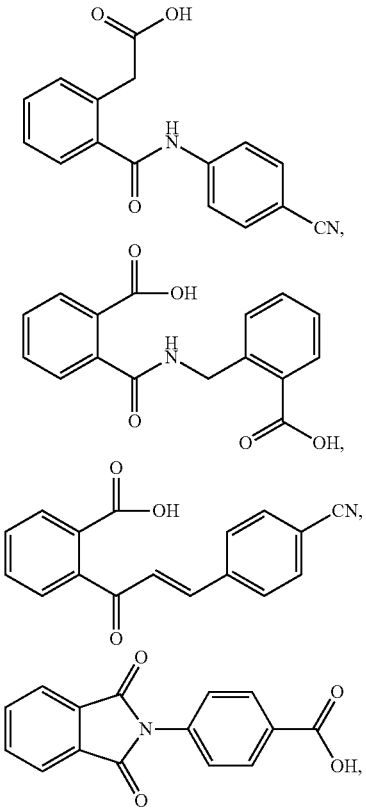

-continued
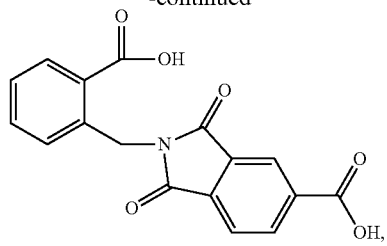
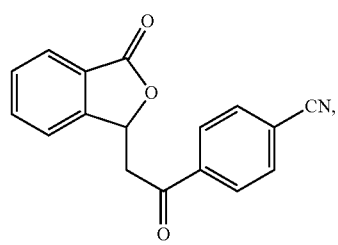
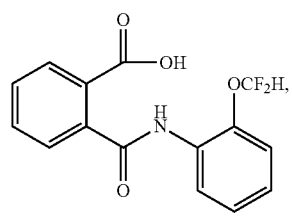
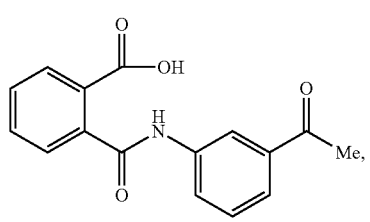
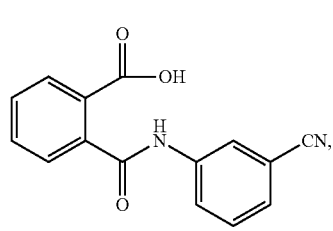
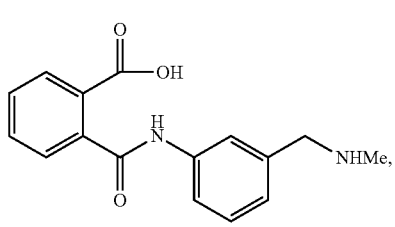
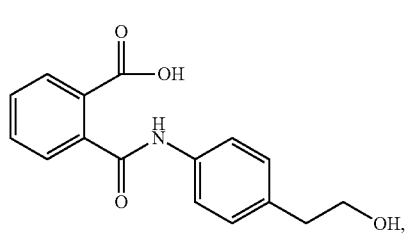
-continued
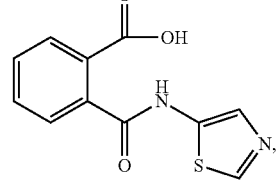
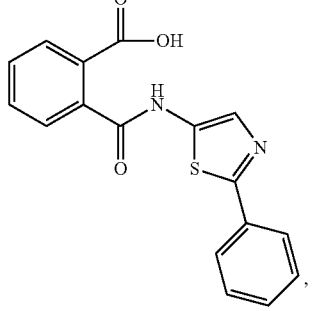
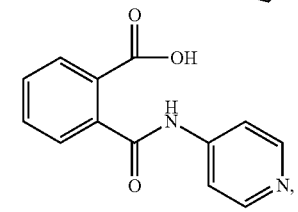
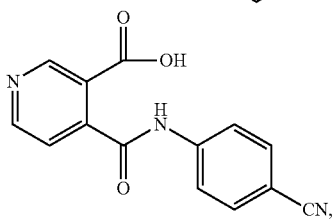
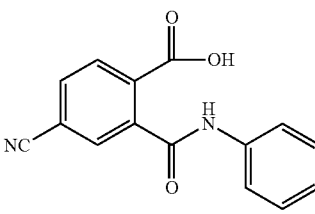
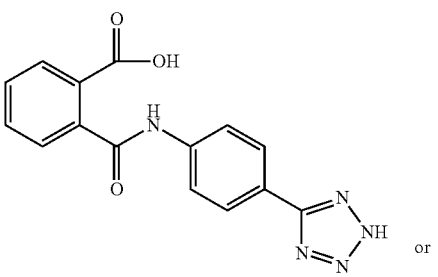
or
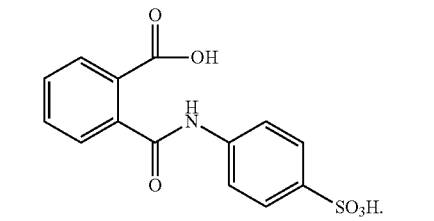

In some embodiments, the compound of the present invention has the structure:
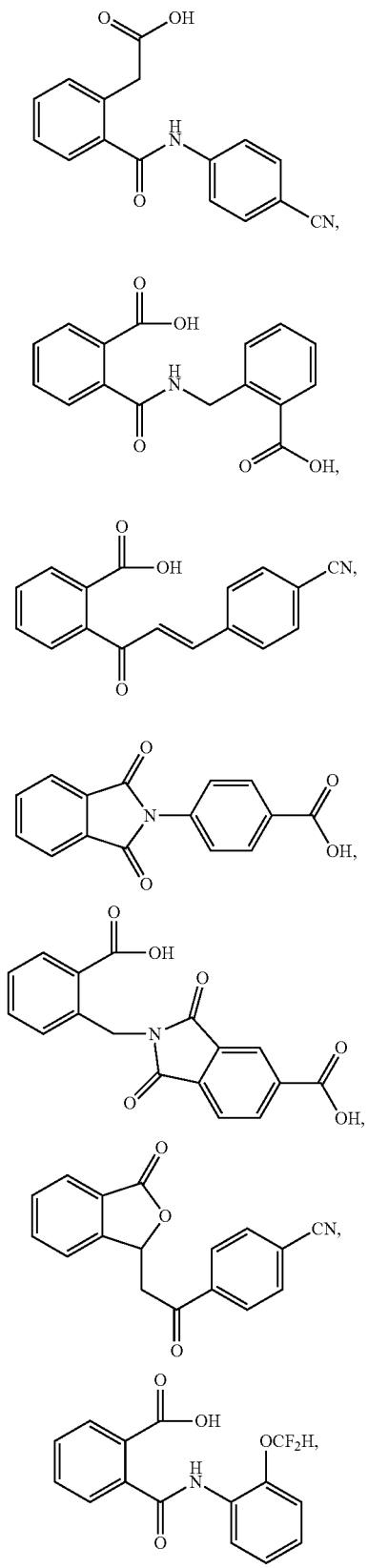
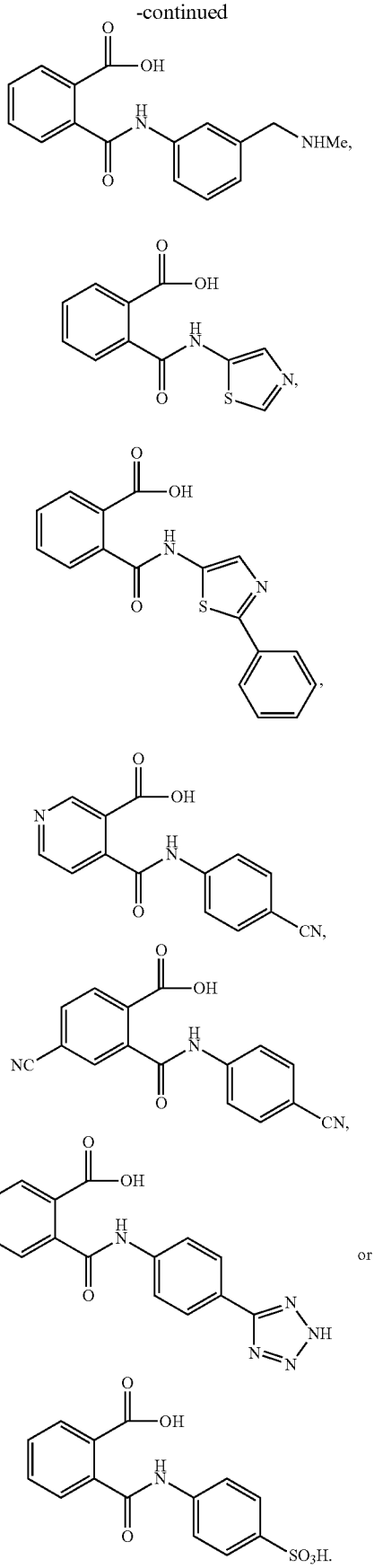

In some embodiments, the compound of the present invention has the structure:
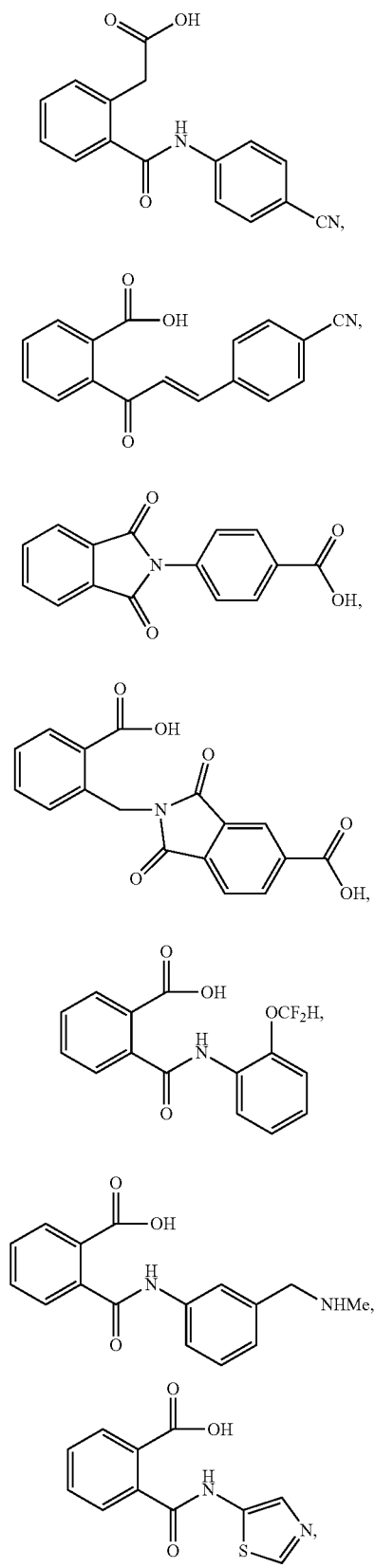
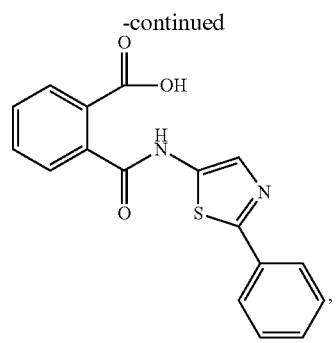
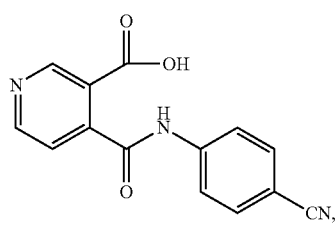
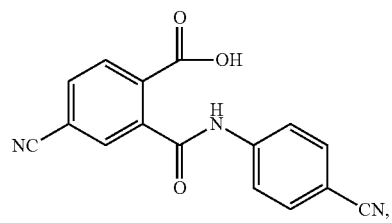
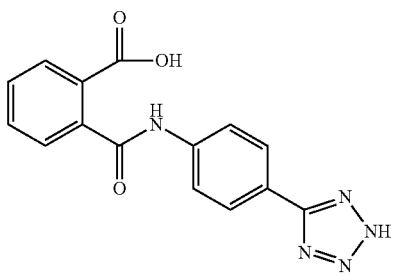
or
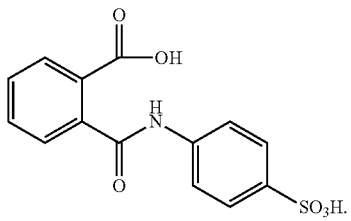
In some embodiments, the compound of the present invention has the structure:
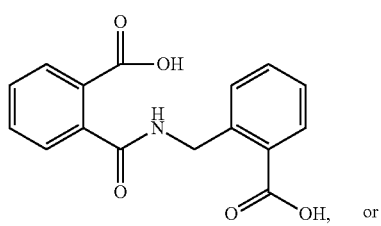
or -continued

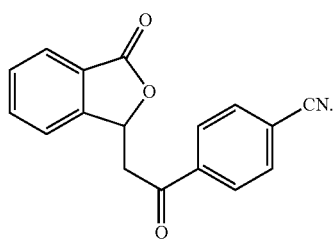

In some embodiments, the compound of the present invention has the structure:

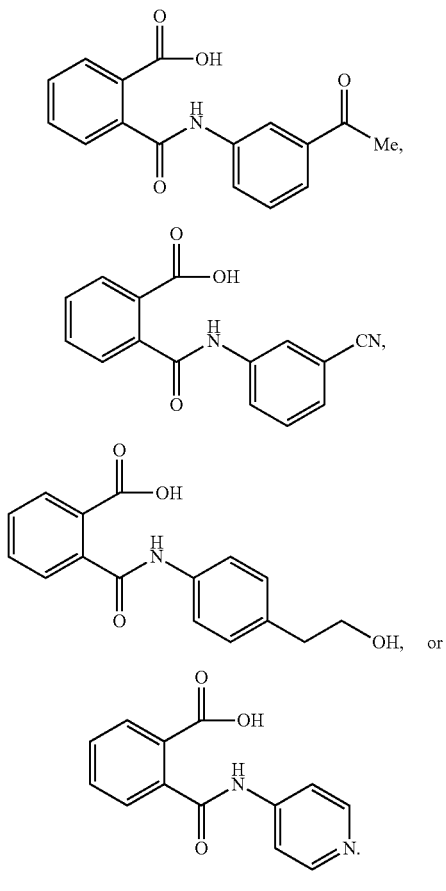

In some embodiments, the compound of the present invention has the structure:

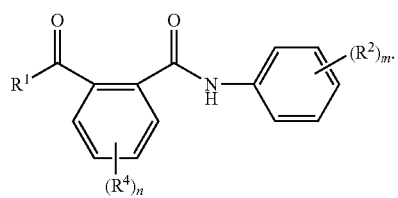

In some embodiments, the compound of the present invention has the structure:

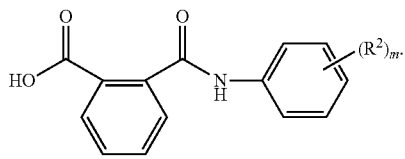

In some embodiments, each $R^2$ is $C_{1-6}$ alkyl, $C_{1-6}$ alkyl-OH, $C_{1-6}$ alkylamine, halogen, phenyl, —$NO_2$, —$CO_2H$, or —CN.

In some embodiments, the compound of the present invention is:

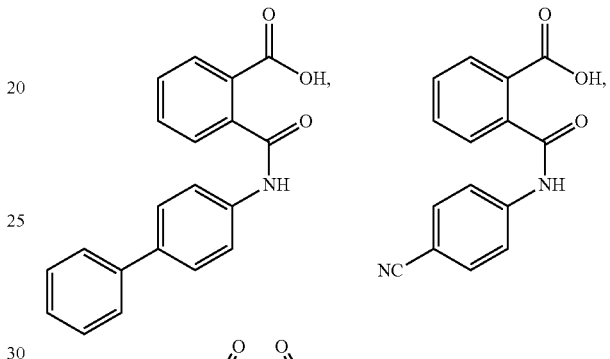

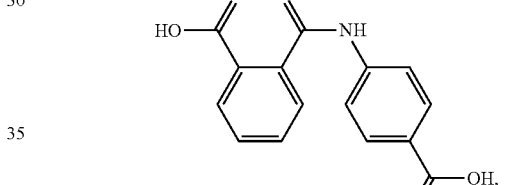

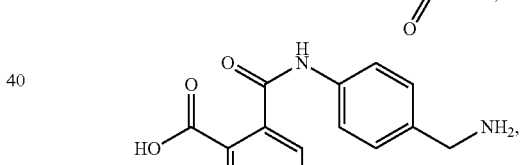

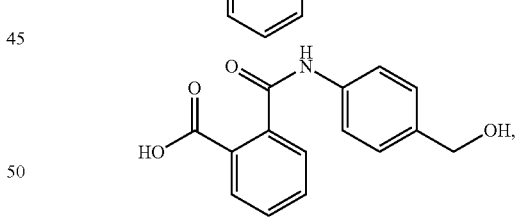

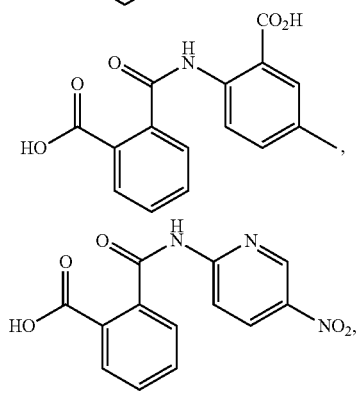

-continued
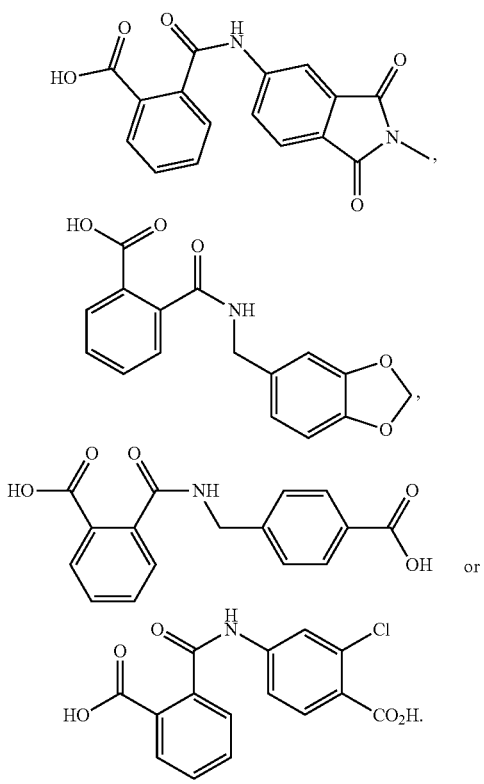
In some embodiments, the compound of the present invention is:
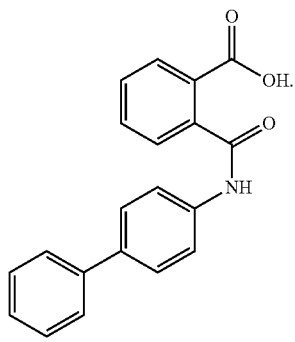 [SMILES: O=C(O)c1ccccc1C(=O)Nc1ccc(-c2ccccc2)cc1]
In some embodiments, the compound of the present invention is:
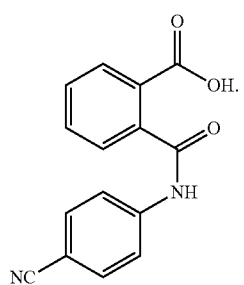
In some embodiments, the present invention provides compounds of the structure:
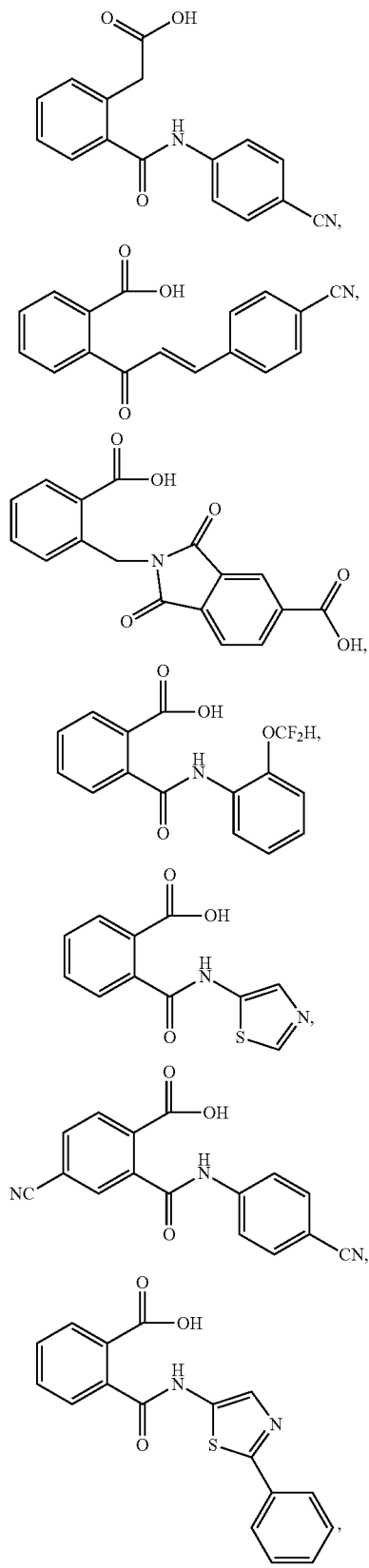

-continued
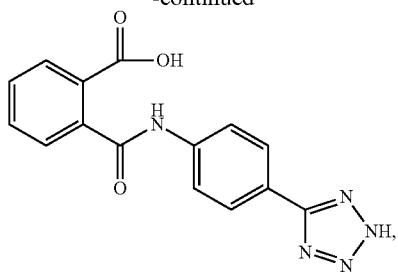
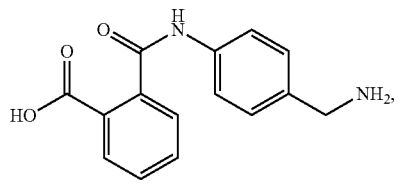
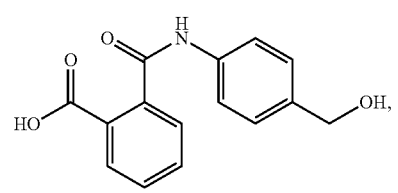
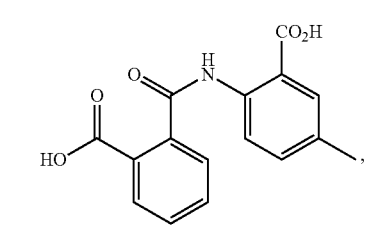
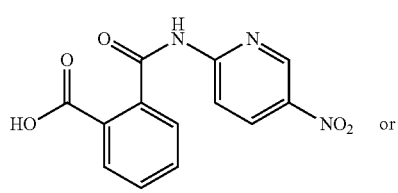
In some embodiments, the present invention provides compounds of the structure:
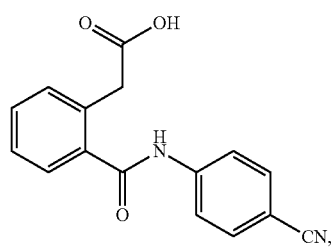
-continued
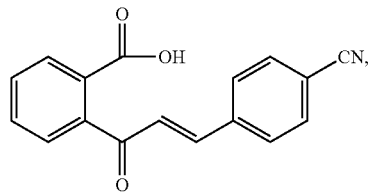
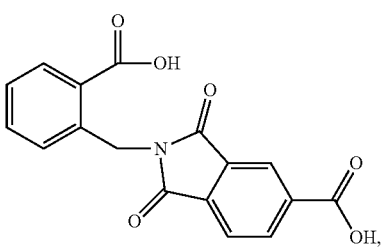
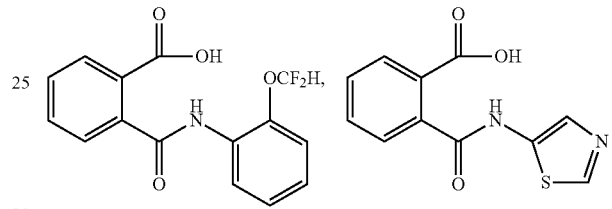
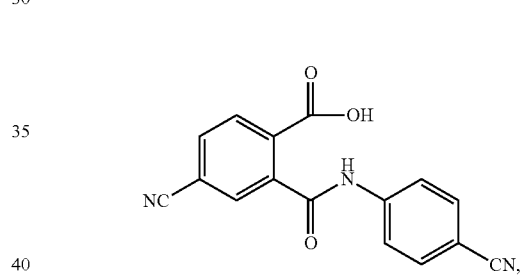
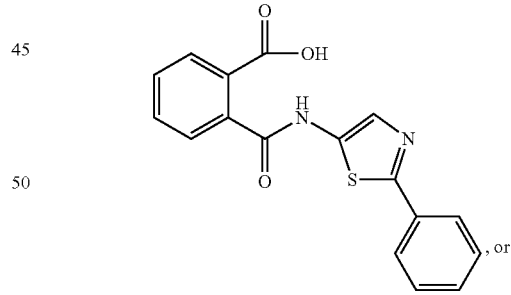
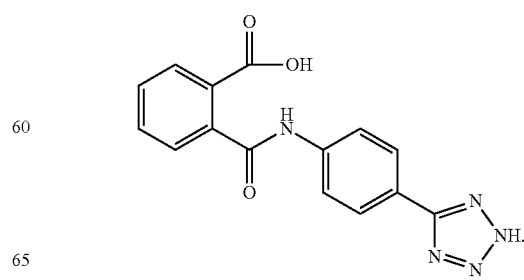

In some embodiments, the compound of the present invention is:

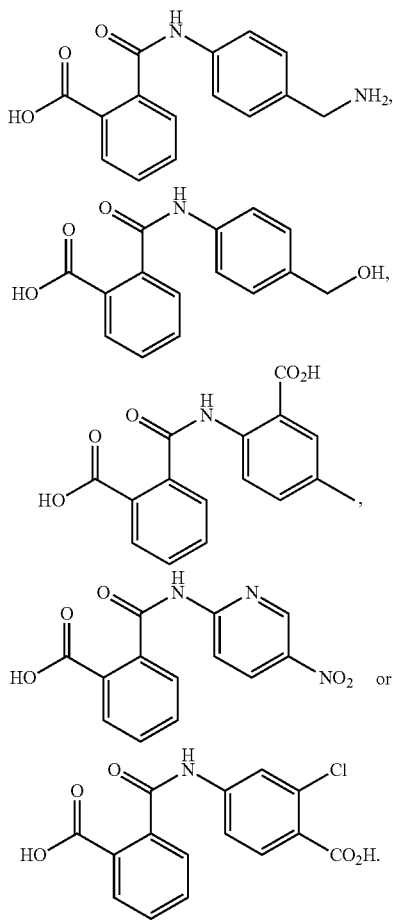

As used herein, the term "salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compounds of the present invention possess asymmetric carbon atoms (optical centers) or double bonds; the racemates, diastereomers, geometric isomers and individual isomers are all intended to be encompassed within the scope of the present invention.

The present invention also includes isotopically-labeled compounds of the present invention, wherein one or more atoms are replaced by one or more atoms having specific atomic mass or mass numbers. Examples of isotopes that can be incorporated into compounds of the invention include, but are not limited to, isotopes of hydrogen, carbon, nitrogen, oxygen, fluorine, sulfur, and chlorine (such as $^2$H, $^3$H, $^{13}$C, $^{14}$C, $^{15}$N, $^{18}$O, $^{17}$O, $^{18}$F, $^{35}$S and $^{36}$Cl). Isotopically-labeled compounds of the present invention are useful in assays of the tissue distribution of the compounds and their prodrugs and metabolites; preferred isotopes for such assays include $^3$H and $^{14}$C. In addition, in certain circumstances substitution with heavier isotopes, such as deuterium (2H or D), can provide increased metabolic stability, which offers therapeutic advantages such as increased in vivo half-life or reduced dosage requirements. Isotopically-labeled compounds of this invention can generally be prepared according to the methods described herein by substituting an isotopically-labeled reagent for a non-isotopically labeled reagent.

The compounds of the present invention can be prepared by a variety of methods known to one of skill in the art. Exemplary methods of making the compounds are described in Example 1. The methods of Example 1 involve first forming an amide by reaction of phthalic anhydride and a suitable amine, such as a substituted aniline. The available carboxylic acid can then be converted to an amide or ester using methods known to one of skill in the art, such as peptide coupling chemistry or carbodiimide chemistry, respectively.

The compounds of the present invention can also be obtained from the Maybridge library from The Scripps Research Institute.

IV. Assay for Identifying Compounds

The compounds of the present invention were identified using a variety of assays. The initial screen identified compounds that stimulated human mesenchymal stem cells (hMSCs) to develop into chondrocyte nodules. Additional assays were performed to determine toxicity and specificity of chondrocyte differentiation.

V. Method of Ameliorating Arthritis or Joint Injury

The present invention provides a method of ameliorating arthritis or joint injury in a mammal, the method including administering to a joint of the mammal a composition having a therapeutically effective amount of a compound of the present invention.

In some embodiments, the mammal does not have, but is at increased risk for, arthritis or joint injury.

It is contemplated that the compounds, compositions, and methods of the present invention may be used to ameliorate any type of arthritis or joint injury. It is further contemplated that the compounds, compositions, and methods of the present invention may be used to ameliorate various cartilagenous disorders. In some embodiments, the compounds and compositions of the present invention are administered to prevent arthritis or joint injury, for example where there is a genetic or family history of arthritis or joint injury or prior or during joint surgery or other circumstances where there is an increased risk of arthritis or joint injury. Exemplary conditions or disorders to be treated or prevented with the compounds, compositions, and methods of the invention, include, but are not limited to systemic rheumatoid arthritis, juvenile chronic arthritis, osteoarthritis, degenerative disc disease, spondyloarthropathies, and systemic sclerosis (scleroderma). In some embodiments of the invention, the compounds, compositions, and methods of the present invention may be used to treat osteoarthritis. In some embodiments, the arthritis can be osteoarthritis, trauma arthritis, degenerative disc disease, dupuytren disease, or tendon disease.

In some embodiments, the compounds, compositions, and methods of the present invention provide a method for stimulating chondrocyte proliferation and cartilage production in cartilagenous tissues that have been damaged due to traumatic injury or chondropathy. Traumatic injury can include, but is not limited to, blunt trauma to the joint, or damage to ligaments such as tearing the anterior cruciate ligament, medial collateral ligament, or a miniscal tear. Examples of tissues that exhibit articulated surfaces, and thus are particularly susceptible to treatment include, but are not limited to, spine, shoulder, elbow, wrist, joints of the fingers, hip, knee, ankle, and the joints of the feet. Examples of diseases that may benefit from treatment include osteoarthritis, rheumatoid arthritis, other autoimmune diseases, or osteochondritis dessicans. In addition, cartilage malformation is often seen in forms of dwarfism in humans suggesting that the compounds, compositions, and methods would be useful in these patients.

It is contemplated that the compounds, compositions, and methods of the present invention may be used to treat a mammal. As used herein a "mammal" refers to any mammal classified as a mammal, including humans, domestic and farm animals, and zoo, sports or pet animals, such as cattle (e.g. cows), horses, dogs, sheep, pigs, rabbits, goats, cats, etc. In some embodiments of the invention, the mammal is a human. In some embodiments, the mammal can be a human, a dog, a horse or a cat.

The compounds and compositions of the present invention can be used in combination with other components suitable for ameliorating arthritis or joint injury. In some embodiments, the composition can also include an angiopoietin-like 3 protein (ANGPTL3) or chondrogenic variant thereof, oral salmon calcitonin, SD-6010 (iNOS inhibitor), vitamin D3 (choliecalciferol), collagen hydrolyzate, FGF18, BMP7, avocado soy unsaponifiables (ASU) or hyaluronic acid. ANGPTL3 is described in more detail in WO2011/008773 (incorporated herein in its entirety).

VI. Method of Inducing Differentiation of MSCs into Chondrocytes

The compounds of the present invention are also useful for inducing differentiation of mesenchymal stem cells (MSCs) into chondrocytes. In some embodiments, the present invention provides a method of inducing differentiation of mesenchymal stem cells into chondrocytes, the method including contacting mesenchymal stem cells with a sufficient amount of a compound of the present invention, thereby inducing differentiation of the stem cells into chondrocytes.

MSCs are multipotent stem cells that can differentiate into several different types of cells including, but not limited to, osteoblasts, chondrocytes and adipocytes. Differentiation is the process by which a specialized cell type is formed from a less specialized cell type, for example, a chondrocyte from a MSC. In some embodiments, the method is performed in vitro. In some embodiments, the method is performed in vivo in a mammal and the stem cells are present in the mammal. In some embodiments, the mammal is a human, a dog, a horse or a cat.

Inducing differentiation of MSCs into chondrocytes can be accomplished using any suitable amount of a compound of the present invention. In some embodiments, the compound of the present invention can be present in an amount from about 0.1 mg to about 10000 mg, e.g., 1.0 mg to 1000 mg, e.g., 10 mg to 500 mg, according to the particular application and potency of the active component. In some embodiments, the compound of the present invention can be present in a concentration of 0.1 µM-100 µM in an intra-articular injection to the knee.

VII. Pharmaceutical Compositions

In some embodiments, the present invention provides a pharmaceutical composition having a pharmaceutically effective amount of a compound of the present invention and a pharmaceutically acceptable excipient.

In some embodiments, the present invention provides a pharmaceutical composition formulated for intra-articular delivery, the composition having a pharmaceutically effective amount of a compound of the present invention and a pharmaceutically acceptable excipient.

The compounds and compositions of the present invention can be used in combination with other components suitable for formulation for intra-articular delivery. In some embodiments, the composition can also include an angiopoietin-like 3 protein (ANGPTL3) or chondrogenic variant thereof, oral salmon calcitonin, SD-6010 (iNOS inhibitor), vitamin D3 (choliecalciferol), collagen hydrolyzate, FGF18, BMP7, avocado soy unsaponifiables (ASU) or hyaluronic acid. ANGPTL3 is described in more detail in WO/2011/008773 (incorporated herein in its entirety).

Liquid form preparations include solutions, suspensions, and emulsions, for example, water or water/propylene glycol solutions. For injection, liquid preparations can be formulated in solution in aqueous polyethylene glycol solution.

Aqueous solutions suitable for use can be prepared by dissolving the active component in water and adding suitable colorants, stabilizers, and thickening agents as desired. Aqueous suspensions suitable for use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

The compounds and compositions of the present invention can be applied by direct injection into the synovial fluid of the joint, systemic administration (oral or intravenously) or directly into the cartilage defect, either alone or complexed with a suitable carrier for extended release of protein. The compounds, compositions, and methods of the present invention can also be used to expand chondrocyte populations in culture for autogenous or allogenic chondrocyte transplantation. The transplantation can be optionally administered with concurrent treatment consisting of administration of the compounds and compositions of the present invention. In these procedures, for example, chondrocytes can be harvested arthroscopically from an uninjured minor load-bearing area of the damaged joint, and can be cultured in the presence of the compounds and compositions of the present invention to increase the number of cells prior to transplantation. The expanded cultures will then be admixed with the compounds and compositions of the present invention, and placed in the joint space or directly into the defect. The compounds and compositions of the present invention can be used in combination with periosteal or perichondrial grafts that contain cells that can form cartilage and/or help to hold the transplanted chondrocytes or their precursor cells in place. The compounds and compositions of the present invention can be used to repair cartilage damage in conjunction with lavage of the joint, stimulation of bone marrow, abrasion arthroplasty, subchondral drilling, or microfracture of the subchondral bone. Additionally, after the growth of cartilage due to the administration of the compounds and compositions of the present invention, additional surgical treatment may be necessary to suitably contour the newly formed cartilage surface. In some embodiments, the pharmaceutical composition can be formulated for intra-articular delivery.

The pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules.

The quantity of active component in a unit dose preparation can be varied or adjusted into an effective dosage. In some embodiments, the dosage range can be from 0.1 mg to 10000 mg, e.g., 1.0 mg to 1000 mg, e.g., 10 mg to 500 mg, according to the particular application and the potency of the active component. The composition can, if desired, also contain other compatible therapeutic agents.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

VIII. Examples

Example 1. Compound Preparation

NMR spectra were recorded with a Bruker AV 400 spectrometer in the solvents indicated $CDCl_3$ and DMSO-$d_6$; chemical shifts ($\delta$) are given in ppm relative to TMS, coupling constants (J) in Hertz. The solvent signals were used as references and the chemical shifts converted to the TMS scale ($CDCl_3$: $\delta C=77.0$ ppm; residual $CHCl_3$ in $CDCl_3$: $\delta H=7.24$ ppm; DMSO-$d_6$: $\delta C=39.5$ ppm; residual DMSO in DMSO-$d_6$: $\delta H=2.5$ ppm). The data are reported as follows: chemical shift, intergration, multiplicity (s for singlet, d for doublet, t for triplet and m for multiplet). The assignments are based upon 1D and 2D spectra recorded using the following pulse sequences from the Bruker standard pulse program library: DEPT; COSY (cosygs and cosydqtp); HSQC (invietgssi) optimized for $^1J(C,H)=145$ Hz; HMBC (inv4gslplrnd) for correlations via $^nJ(C,H)$; HSQC-TOCSY (invietgsml) using an MLEV17 mixing time of 120 ms. Finnigan MAT 8200 (70 eV), ESI-MS: Finnigan MAT 95, accurate mass determination. Unless stated otherwise, all commercially available compounds (Fluka, Lancaster, Aldrich) were used as received. Solvents were purchased from VWR and Fisher. Reactions were carried out in oven-dried glassware under argon atmosphere, unless otherwise noted. Flash chromatography: Merck silica gel 60 (230-400 mesh).

General Methods

The following methods can be used to prepare the compounds of the present invention. Additional methods for making selected compounds of the present invention are provided below.

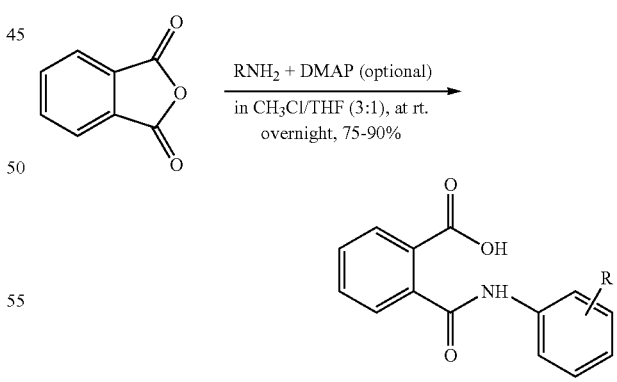

General Protocol Starting from Phthalic Anhydride.

To a solution of phthalic anhydride (1.05 equiv) in a 3:1 mixture of chloroform/THF (0.05 M concentration) was added the corresponding amine ($R/ArNH_2$, 1 equiv). The mixture was stirred overnight at room temperature. The reaction mixture was washed with brine (×2). The aqueous solution was then extracted with ethyl acetate (×3) and dried over sodium sulfate. Combined organic phases were concentrated under reduced pressure and adsorbed on silica gel to be purified by flash chromatography to afford the desired amide.

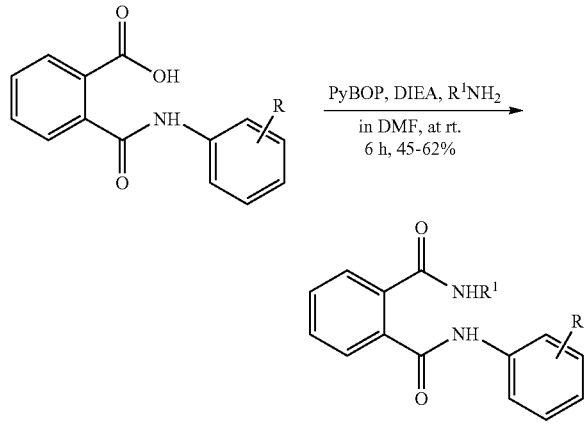

General Protocol for the Amide Bond Formation.

To a solution of acid and diisopropylethylamine (DIEA, 2.2 equiv) in DMF (0.1 M concentration) at 0° C. was added the corresponding amine ($R^1NH_2$, 1.2 equiv). The mixture was stirred for 30 min and PyBOP (1.1 equiv) was added and stirred at room temperature for 6 h. The slurry reaction mixture was washed with brine (×5 to assure complete removal of DMSO; volume of brine ~10 times volume of DMSO). The aqueous solution was then extracted with ethyl acetate (×3) and dried over sodium sulfate. Combined organic phases were concentrated under reduced pressure and adsorbed on silica gel to be purified by flash chromatography to afford the desired amide.

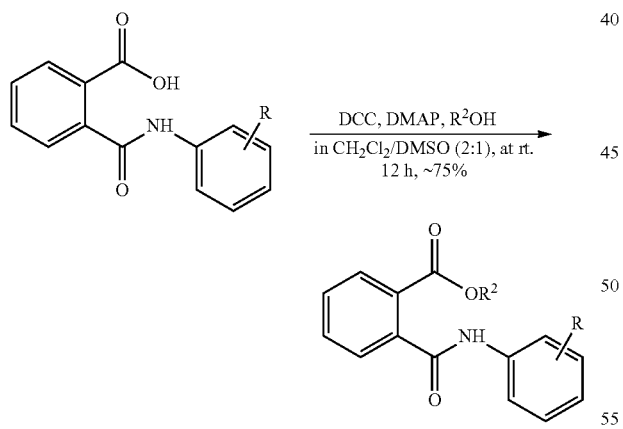

General Protocol for the Ester Bond Formation.

DCC (0.9 equiv) and DMAP (0.2 equiv) were added to a solution of the selected alcohol (1.2 equiv) in $CH_2Cl_2$/DMSO (2:1; 0.1 M) at 0° C. The mixture was stirred for 30 min before acid (1 equiv) was introduced and stirring continued for 12 h at ambient temperature. For work up, all volatile materials were evaporated, the product adsorbed on silica and purified by flash chromatography (hexanes/ethyl acetate) to give the desired product (yield ~75%).

AKT

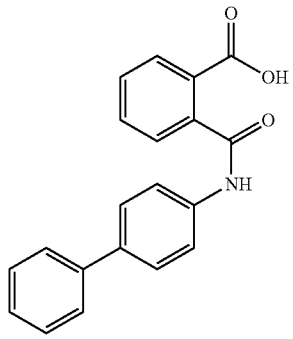 [SMILES: O=C(O)c1ccccc1C(=O)Nc1ccc(-c2ccccc2)cc1]

AKT—

AKT was recrystallized from of $CHCl_3$/MeOH (2:1). $^1$H NMR (400 MHz, $(CD_3)_2SO$) δ 7.36 (tt, J=7.4, 1.2 Hz, 1H), 7.47 (tt, J=7.5, 1.2 Hz, 2H), 7.59 (m, 2H), 7.66 (m, 5H), 7.81 (dt, J=6.7, 1.7 Hz, 2H), 7.91 (dd, J=7.3, 1.7 Hz, 1H), 10.45 (brs, 1H); $^{13}$C NMR (100 MHz, $(CD_3)_2SO$) δ 163.9, 139.0, 136.2, 133.1, 132.4, 129.1, 128.5, 120.5, 118.3, 113.8, 20.5; HRMS (ESI): 317.1130 [M+H+]; calcd for [$C_{20}H_{15}NO_3$+H+] 318.1125.

AKT-Me

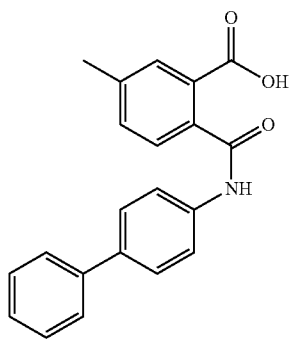 [SMILES: Cc1ccc(C(=O)Nc2ccc(-c3ccccc3)cc2)c(C(=O)O)c1]

AKT-Me.

Rf ($CHCl_3$/MeOH 3/1): 0.4. The desired AKT-Me derivative was obtained as light yellow solid. $^1$H NMR (400 MHz, $(CD_3)_2SO$) δ 2.66 (s, 3H), 7.49 (t, J=7.4 Hz, 2H), 7.61 (m, 5H), 7.83 (dm, J=8.3 Hz, 2H), 7.92 (dm, J=8.7 Hz, 2H), 8.13 (dd, J=8.7, 5.6 Hz, 1H), 10.71 (brs, 1H) HRMS (ESI): 332.1277 [M+H+]; calcd for [$C_{21}H_{18}NO_3$+H+] 332.1281.

AKT-$CH_2OH$

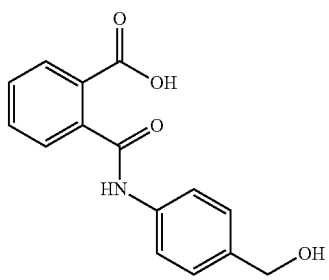 [SMILES: O=C(O)c1ccccc1C(=O)Nc1ccc(CO)cc1]

2-((4-(hydroxymethyl)phenyl)carbamoyl)benzoic acid

The desired derivative was obtained as brown solid after purification on silica. Rf($CHCl_3$/MeOH: 9/1): 0.3. $^1$H-NMR (400 MHz, (CD$_3$)$_2$SO): δ 4.32 (d, J=1.6 Hz, 2H), 6.6 (d, J=8.6 Hz, 1H), 7.26 (dd, J=8.6, 2.5 Hz, 1H), 7.39 (d, J=2.3 Hz, 1H), 7.54 (dt, J=6.1, 1.3 Hz, 1H), 7.56 (dt, J=7.6, 1.3 Hz, 1H), 7.63 (dt, J=7.5, 1.3 Hz, 1H), 7.83 (dd, J=7.6, 1.0 Hz, 1H), 8.32 (m, 1H), 9.08 (m, 1H), 9.99 (brs, 1H). HRMS (ESI): 272.0931 [M+H+]; calcd for [C$_{14}$H$_{11}$NO$_4$+H+] 272.0923.

AKT-Biotin

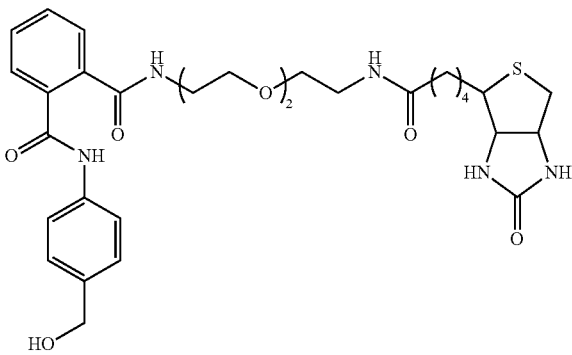

PRO-1-Linker-biotin

AKT-Biotine.

Rf(CHCl$_3$/MeOH 10/1): 0.25. The desired AKT-Biotine derivative was obtained white yellow solid. $^1$H-NMR (400 MHz, (CD$_3$)$_2$SO): δ 1.22 (m, 2H), 1.53 (m, 2H), 2.60 (dm, J=6.9 Hz, 2H), 2.74 (d, J=2.1 Hz, 2H), 2.85 (m, 2H), 3.03 (m, 1H), 3.21 (m, 1H), 3.30 (d, J=6.8 Hz, 2H), 3.51 (m, 8H), 3.98 (m, 2H), 4.12 (ddm, J=8.7, 2.1 Hz, 2H), 6.2 (brs, 2H), 6.78 (dd, J=8.7, 2.3 Hz, 2H), 7.05 (m, 1H), 7.50 (m, 4H), 7.73 (m, 1H), 7.82 (m, 1H), 8.1 (brs, 1H—NH), 8.2 (brs, 1H—NH), 9.2 (brs, 1H—NH). HRMS (ESI): 627.2754 [M+H+]; calcd for [C$_{31}$H$_{41}$N$_5$O$_7$S+H+] 627.2757.

AKT-Azide

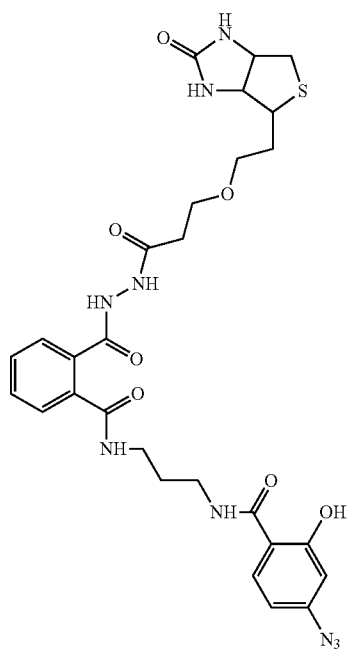 [SMILES: [N-]=[N+]=Nc1ccc(C(=O)NCCCNC(=O)c2ccccc2C(=O)NNC(=O)CCOCCC2SCC3NC(=O)NC32)c(O)c1]

AKT-Azide.

Rf (CHCl$_3$/MeOH 20/1): 0.33. The desired AKT-azide derivative was obtained as light yellow oil. $^1$H-NMR (400 MHz, (CD$_3$)$_2$SO): δ 1.76 (m, 3H), 1.84 (m, 2H), 2.14 (m, 2H), 2.20 (t, J=6.9 Hz, 2H), 2.46 (m, 1H), 2.59 (d, J=12.5 Hz, 1H), 2.82 (dd, J=12.5, 5.1 Hz, 1H), 3.03 (m, 2H), 3.12 (m, 2H), 3.41 (m, 1H), 4.13 (ddd, J=7.4, 6.1, 1.1 Hz, 1H), 4.32 (dd, J=7.5, 5.2 Hz, 1H), 6.36 (brs, 1H—NH), 6.42 (brs, 1H—NH), 7.43 (s, 1H), 7.48 (m, 2H), 7.75 (m, 3H), 7.95 (m, 1H), 7.96 (d, J=8.6 Hz, 1H), 8.17 (brs, 1H—NH), 8.18 (brs, 1H—NH), 8.29 (brs, 1H—NH), 8.3 (brs, 1H—NH). HRMS (ESI): 640.2293 [M+H+]; calcd for [C$_{28}$H$_{33}$N$_9$O$_7$S+H+] 640.2296.

AKT-CN; LK3

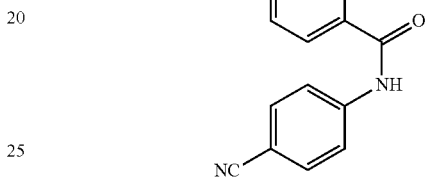

AKT-CN; LK3.

Rf (CHCl$_3$/MeOH 9/1): 0.4. The desired AKT-CN derivative was obtained as brown solid. $^1$H-NMR (400 MHz, (CD$_3$)$_2$SO): δ 7.57 (m, 2H), 7.59 (m, 1H), 7.61 (dt, J=7.6, 1.2 Hz, 1H), 7.69 (dt, J=7.5, 1.2 Hz, 1H), 7.92 (m, 1H), 8.17 (m, 1H), 10.73 (brs, 1H). HRMS (ESI): 266.0695 [M+H+]; calcd for [C$_{15}$H$_{10}$N$_2$O$_3$+H+] 266.0691.

LK-14b

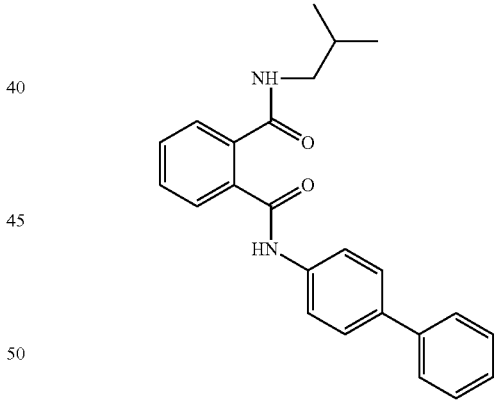

LK-14b, N-([1,1'-biphenyl]-4-yl)-N-isobutylphthalamide

Rf (CHCl$_3$/MeOH 15/1): 0.3. The desired AKT-isopropylamine derivative was obtained as brown solid. $^1$H-NMR (400 MHz, (CD$_3$)$_2$SO): δ 0.93 (d, J=6.8 Hz, 3H), 0.94 (d, J=6.8 Hz, 3H), 1.77 (m, 1H), 3.04 (dd, J=6.65, 5.59 Hz, 2H), 7.31 (dt, J=7.3, 1.59 Hz, 1H), 7.35 (dt, J=7.3, 1.48 Hz, 1H), 7.43 (dd, J=7.51, 1.09 Hz, 1H), 7.49 (t, J=7.4 Hz, 2H), 7.61 (m, 2H), 7.67 (dd, J=7.51, 1.18 Hz, 1H), 7.83 (dm, J=8.3 Hz, 2H), 7.92 (dm, J=8.7 Hz, 2H), 8.13 (dd, J=8.7, 5.6 Hz, 1H). HRMS (ESI): 373.1928 [M+H+]; calcd for [C$_{24}$H$_{24}$N$_2$O$_2$+H+] 373.1916.

LK-23

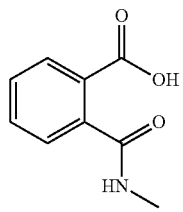

LK-23, 2-(methylcarbamoyl)benzoic acid

Rf (CHCl$_3$/MeOH 15/1): 0.3. The desired derivative was obtained as brown solid. 1H-NMR (400 MHz, (CD$_3$)$_2$SO): δ 2.97 (s, 3H), 7.63 (m, 2H), 7.98 (m, 2H), 9.58 (brs, 1H). HRMS (ESI): 189.0672 [M+H+]; calcd for [C$_9$H$_9$NO$_3$+H+] 180.0661.

LK-19b

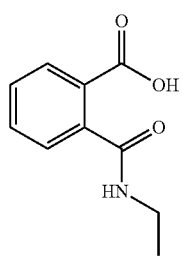

LK-19b, 2-(ethylcarbamoyl)benzoic acid

Rf(CHCl$_3$/MeOH 15/1): 0.3. The desired derivative was obtained as brown solid. $^1$H-NMR (400 MHz, (CD$_3$)$_2$SO): δ 1.07 (t, J=6.8 Hz, 3H), 3.19 (q, J=6.8 Hz, 2H), 7.39 (m, 2H), 7.52 (m, 2H), 9.58 (brs, 1H). HRMS (ESI): 194.0825 [M+H+]; calcd for [C$_{10}$H$_{11}$NO$_3$+H+] 194.0817.

LK-62

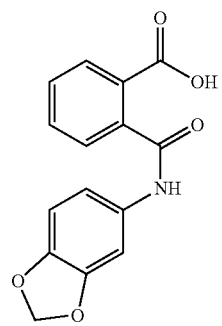 [SMILES: O=C(O)c1ccccc1C(=O)Nc1ccc2c(c1)OCO2]

LK-62, 2-(benzo[1,3]dioxol-5-ylcarbamoyl)benzoic acid

Rf (CHCl$_3$/MeOH 12/1): 0.5. The desired derivative was obtained as yellow powder. $^1$H-NMR (400 MHz, (CD$_3$)$_2$SO): δ 6.87 (m, 1H), 6.9 (m, 1H), 7.02 (d, J=1.3 Hz, 1H), 7.36 (m, 2H), 7.52 (dd, J=7.6, 1.3 Hz, 1H), 7.65 (dd, J=7.2, 1.3 Hz, 1H), 10.56 (brs, 1H). HRMS (ESI): 286.0725 [M+H+]; calcd for [C$_{15}$H$_{11}$NO$_5$+H+] 286.0715.

LK-60

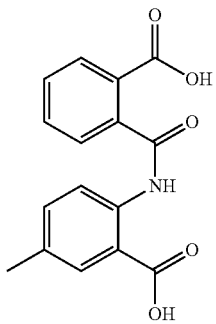 [SMILES: Cc1ccc(NC(=O)c2ccccc2C(=O)O)c(C(=O)O)c1]

LK-60, 2-(2-carboxybenzamido)-5-methylbenzoic acid

The desired derivative was obtained as white powder, recrystallized out from CHCl$_3$/MeOH (1:1). 1H-NMR (400 MHz, (CD$_3$)$_2$SO): δ 2.40 (s, 3H), 7.03 (dd, J=8.1, 1.02 Hz, 1H), 7.66 (m, 3H), 7.86 (dd, J=6.38, 1.02 Hz, 1H), 7.92 (d, J=8.1 Hz, 1H), 8.51 (s, 1H), 11.59 (brs, 1H). HRMS (ESI): 300.0881 [M+H+]; calcd for [C$_{16}$H$_{13}$NO$_5$+H+] 300.0872.

LK-63

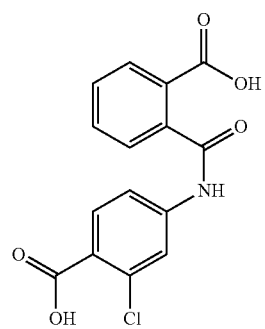 [SMILES: O=C(O)c1ccc(NC(=O)c2ccccc2C(=O)O)cc1Cl]

LK-63, 4-(2-carboxybenzamido)-2-chlorobenzoic acid

The desired derivative was obtained as white powder. $^1$H-NMR (400 MHz, (CD$_3$)$_2$SO): δ 7.46 (m, 3H), 7.75 (d, J=8.9 Hz, 1H), 7.92 (d, J=9.03 Hz, 1H), 8.30 (d, J=8.9 Hz, 1H), 8.42 (d, J=1.1 Hz, 1H), 9.15 (brs, —NH, 1H), 10.59 (brs, 1H), 11.0 (brs, 1H). HRMS (ESI): 320.0323 [M+H+]; calcd for [C$_{15}$H$_{10}$ClNO$_5$+H+] 320.0326.

LK-57

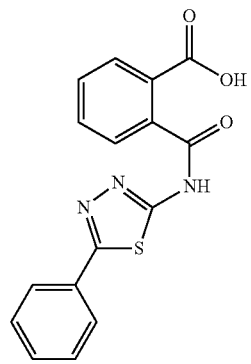 [SMILES: O=C(O)c1ccccc1C(=O)Nc1nnc(-c2ccccc2)s1]

LK-57, 2-((5-phenyl-1,3,4-thiadiazol-2-yl)carbamoyl)benzoic acid

The desired derivative was obtained as yellow powder, recrystallized out from CHCl$_3$/MeOH (1:1). $^1$H-NMR (400 MHz, (CD$_3$)$_2$SO): δ 7.52-7.54 (m, 2H), 7.57 (m, 1H), 7.96 (dm, J=1.6 Hz, 1H), 7.97 (m, 1H), 7.98 (d, J=2.8 Hz, 1H), 7.99 (m, 1H), 8.01 (dd, J=5.6, 2.8 Hz, 2H), 10.81 (brs, 1H). HRMS (ESI): 326.0594 [M+H+]; calcd for [C$_{16}$H$_{11}$N$_3$O$_3$S+H+] 326.0599.

L2

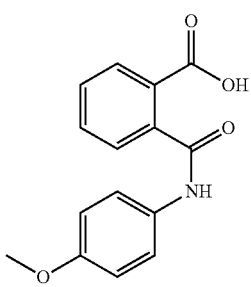 [SMILES: COc1ccc(NC(=O)c2ccccc2C(=O)O)cc1]

L2, 2-((4-methoxyphenyl)carbamoyl)benzoic acid

The desired derivative was obtained as colorless oil, Rf(CHCl$_3$/MeOH 9/1): 0.3. $^1$H-NMR (400 MHz, (CD$_3$)$_2$SO): δ 3.34 (s, 2H), 7.54 (m, 1H), 7.6 (m, 3H), 7.64 (dt, J=7.5, 1.3 Hz, 1H), 7.85 (dd, J=7.6, 1.1 Hz, 1H), 10.2 (brs, 1H). HRMS (ESI): 272.0929 [M+H+]; calcd for [C$_{15}$H$_{13}$NO$_4$+H+] 272.0923.

L4

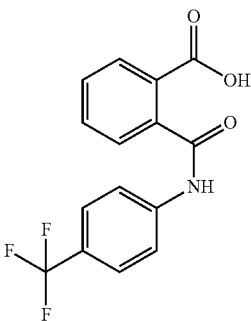 [SMILES: O=C(O)c1ccccc1C(=O)Nc1ccc(C(F)(F)F)cc1]

L4, 2-((4-(trifluoromethyl)phenyl)carbamoyl)benzoic acid

The desired derivative was obtained as yellowish oil, Rf(CHCl$_3$/MeOH 9/1): 0.3. $^1$H-NMR (400 MHz, (CD$_3$)$_2$SO): δ 7.45 (d, J=7.3 Hz, 1H), 7.51 (t, J=7.6 Hz, 1H), 7.61 (m, 2H), 7.69 (dd, J=14.8, 11.6 Hz, 1H), 7.76 (m, 2H), 7.91 (dd, J=7.7, 0.9 Hz, 1H), 10.12 (brs, 1H). HRMS (ESI): 310.0687 [M+H+]; calcd for [C$_{15}$H$_{16}$FNO$_3$+H+] 310.0691.

L11a

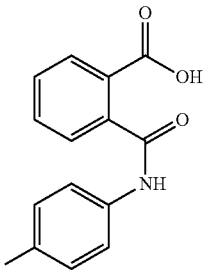

L11a, 2-((4-iodophenyl)carbamoyl)benzoic acid

The desired derivative was obtained as bright yellow solid after purification on silica. Rf(CHCl$_3$/MeOH 11/1): 0.3. $^1$H-NMR (400 MHz, (CD$_3$)$_2$SO): δ 7.53 (m, 5H), 7.66 (dt, J=11.6, 2.4 Hz, 2H), 7.80 (m, 1H), 11.2 (brs, 1H). $^{13}$C-NMR (100 MHz, (CD$_3$)$_2$SO): 86.3, 121.5, 128.4, 129.4, 129.9, 130.1, 134.3, 139.7, 167.8, 169.05. HRMS (ESI): 367.8798 [M+H+]; calcd for [C$_{14}$H$_{10}$INO$_3$+H+] 367.8794.

L15

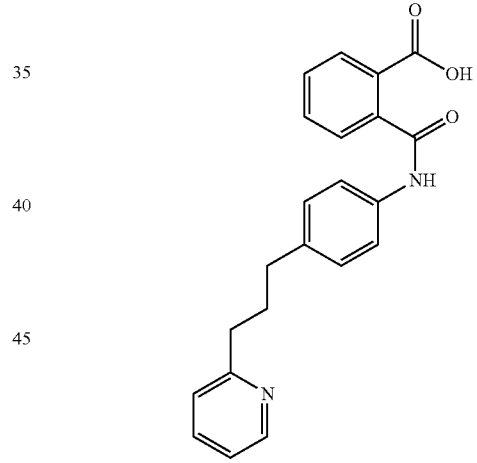

LK15, 2-((4-(3-(pyridin-2-yl)propyl)phenyl)carbamoyl)benzoic acid

The desired derivative was obtained as brown powder after purification on silica. Rf (CHCl$_3$/MeOH 15/1): 0.2. $^1$H-NMR (400 MHz, (CD$_3$)$_2$SO): δ 2.82 (t, J=7.2 Hz, 2H), 2.99 (t, J=6.5 Hz, 2H), 3.44 (tt, J=7.2, 6.5 Hz, 2H), 7.32 (m, 2H), 7.55 (dd, J=16.5, 7.3 Hz, 2H), 7.70 (m, 2H), 8.41 (dd, J=4.8, 1.6 Hz, 1H), 8.45 (dd, J=4.4, 1.6 Hz, 1H), 8.47 (brs, NH—, 1H). $^{13}$C-NMR (100 MHz, (CD$_3$)$_2$SO): 30, 32.1, 41.3, 123.8, 127.5, 128.7, 130.0, 131.3, 134.4, 136.3, 145, 148.8, 165.1, 167.2. HRMS (ESI): 361.1559 [M+H+]; calcd for [C$_{22}$H$_{20}$N$_2$O$_3$+H+] 361.1552.

L59

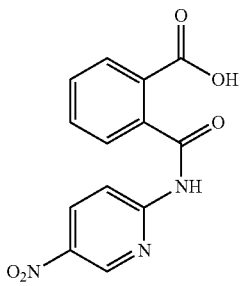 [SMILES: O=C(O)c1ccccc1C(=O)Nc1ccc([N+](=O)[O-])cn1]

LK59, 2-((5-nitropyridin-2-yl)carbamoyl)benzoic acid

The desired derivative was obtained as light yellow powder after purification on silica. Rf(CHCl₃/MeOH 9/1): 0.3. ¹H-NMR (400 MHz, (CD₃)₂SO): δ 7.04 (d, J=4.4 Hz, 1H), 7.95 (m, 2H), 7.96 (dd, J=16.1, 8.3 Hz, 1H), 8.49 (m, 2H), 8.71 (d, J=1.8 Hz, 1H), 10.92 (brs, 1H). HRMS (ESI): 288.0616 [M+H+]; calcd for [C₁₃H₉NO₅+H+] 288.0620.

L9

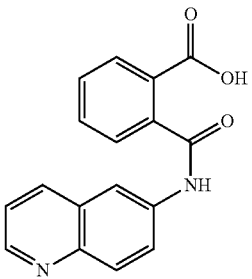 [SMILES: O=C(O)c1ccccc1C(=O)Nc1ccc2ncccc2c1]

L9, 2-(quinolin-6-ylcarbamoyl)benzoic acid

The desired derivative was obtained as light brown powder after purification on silica. Rf(CHCl₃/MeOH 8/1): 0.3. ¹H-NMR (400 MHz, (CD₃)₂SO): δ 7.55 (dd, J=8.5, 4.1 Hz, 1H), 7.62 (m, 1H), 7.72 (m, 2H), 7.80 (m, 2H), 7.94 (m, 2H), 8.65 (d, J=8.5 Hz, 1H), 8.93 (dd, J=4.1, 1.5 Hz, 1H), 10.54 (brs, 1H). HRMS (ESI): 293.0929 [M+H+]; calcd for [C₁₇H₁₂N₂O₃+H+] 293.0926.

L7

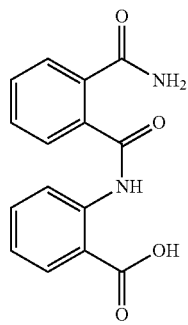 [SMILES: NC(=O)c1ccccc1C(=O)Nc1ccccc1C(=O)O]

L7, 2-(2-carbamoylbenzamido)benzoic acid

The desired derivative was obtained as light white solid after purification on silica. Rf (CHCl₃/MeOH 10/1): 0.25. ¹H-NMR (400 MHz, (CD₃)₂SO): δ 7.57 (m, 1H), 7.59 (m, 1H), 7.62 (m, 2H), 7.68 (m, 1H), 7.73 (brs, 2H), 7.85 (m, 1H), 8.33 (d, J=8.2 Hz, 1H), 8.59 (d, J=8.2 Hz, 1H), 12.22 (brs, 1H). HRMS (ESI): 285.0882 [M+H+]; calcd for [C₁₅H₁₂N₂O₄+H+] 285.0875.

LK6

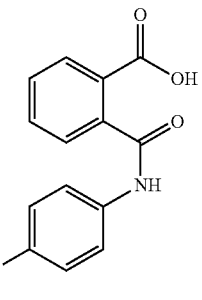

LK6, 2-((4-morpholinophenyl)carbamoyl)benzoic acid

The desired derivative was obtained as light blue solid after purification on silica. Rf (CHCl₃/MeOH 6/1): 0.4. ¹H-NMR (400 MHz, (CD₃)₂SO): δ 3.05 (dd, J=4.8, 4.7 Hz, 2H), 3.74 (dd, J=5.1, 4.5 Hz, 2H), 6.92 (dm, J=9.09 Hz, 2H), 7.51-7.57 (m, 4H), 7.64 (dt, J=7.5, 1.4 Hz, 1H), 7.85 (dd, J=7.6 Hz, 1H), 10.12 (brs, 1H). HRMS (ESI): 327.1351 [M+H+]; calcd for [C₁₈H₁₉N₃O₃+H+] 327.1345.

LK17b

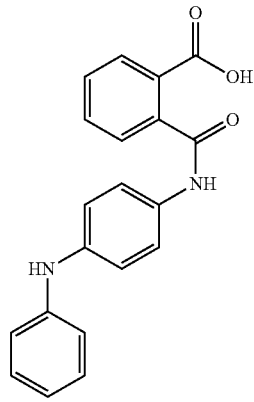 [SMILES: O=C(O)c1ccccc1C(=O)Nc1ccc(Nc2ccccc2)cc1]

LK17b, 2-((4-(phenylamino)phenyl)carbamoyl)benzoic acid

The desired derivative was obtained as white powder after purification on silica. Rf (CHCl₃/MeOH 9/1): 0.3. ¹H-NMR (400 MHz, (CD₃)₂SO): δ 6.77 (tt, J=7.3, 1.1 Hz, 2H), 7.02 (ddm, J=15.8, 8.8 Hz, 2H), 7.20 (tt, J=8.2, 1.2 Hz, 2H), 7.54 (dt, J=7.5, 1.4 Hz, 1H), 7.56 (m, 4H), 7.65 (dt, J=7.5, 1.4 Hz, 1H), 7.86 (dd, J=1.2 Hz, 1H), 8.07 (brs, NH—, 1H), 10.2 (brs, 1H). HRMS (ESI): 333.1241 [M+H+]; calcd for [C₂₀H₁₆N₃O₂+H+] 333.1239.

L11b

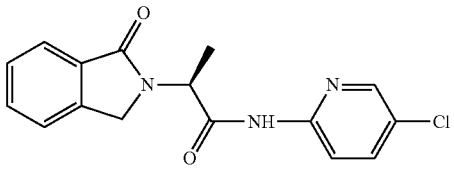 [SMILES: C[C@@H](C(=O)Nc1ccc(Cl)cn1)N1Cc2ccccc2C1=O]

L11b, (S)—N-(5-chloropyridin-2-yl)-2-(1-oxoisoindolin-2-yl)propanamide

The desired derivative was obtained as yellow powder after purification on silica. Rf (AcOEt/Hex.: 3/2): 0.2. $^1$H-NMR (400 MHz, (CD$_3$)$_2$SO): δ 2.14 (d, J=7.3 Hz, 3H), 4.63 (d, J=17 Hz, 1H), 4.75 (d, J=17 Hz, 1H), 5.10 (dd, J=7.3, 7.3 Hz, 1H), 7.50 (m, 1H), 7.62 (m, 2H), 7.7 (d, J=7.5 Hz, 1H), 7.9 (dd, J=8.9, 2.6 Hz, 1H), 8.05 (d, J=8.9 Hz, 1H), 8.4 (d, J=8.9 Hz, 1H), 10.96 (brs, NH—, 1H). HRMS (ESI): 316.0859 [M+H+]; calcd for [C$_{16}$H$_{14}$ClN$_3$O$_2$+H+] 316.0853.

LK19b

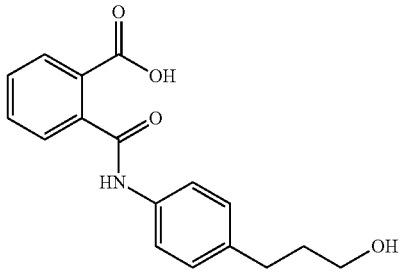 [SMILES: O=C(O)c1ccccc1C(=O)Nc1ccc(CCCO)cc1]

LK19b, 2-(ethylcarbamoyl)benzoic acid

The desired derivative was obtained as bright yellow oil after purification on silica. Rf(CHCl$_3$/MeOH: 12/1): 0.3. $^1$H-NMR (400 MHz, (CD$_3$)$_2$SO): δ 1.09 (t, J=7.2 Hz, 3H), 3.35 (brs, 1H), 3.2 (dq, J=15.4, 7.2 Hz, 2H), 7.30 (m, 2H), 7.58 (m, 2H). HRMS (ESI): 194.0821 [M+H+]; calcd for [C$_{10}$H$_{11}$NO$_3$+H+] 194.0817.

L11c

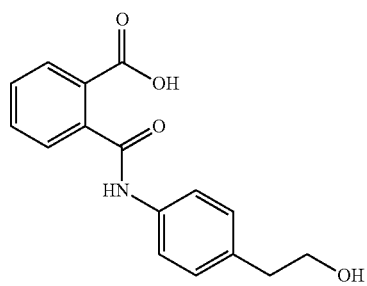 [SMILES: O=C(O)c1ccccc1C(=O)Nc1ccc(CCO)cc1]

L11c, 2-((4-(2-hydroxyethyl)phenyl)carbamoyl)benzoic acid

The desired derivative was obtained as bright yellow oil after purification on silica. Rf (CHCl$_3$/MeOH: 12/1): 0.3. $^1$H-NMR (400 MHz, (CD$_3$)$_2$SO): δ 2.79 (dd, J=7.0, 6.9 Hz, 2H), 3.65 (dd, J=7.0, 6.9 Hz, 2H), 7.27 (dt, J=9.1, 2.2 Hz, 2H), 7.53 (dd, J=7.5, 1.2 Hz, 2H), 7.56-7.6 (m, 3H), 7.64 (dt, J=7.5, 1.3 Hz, 1H), 7.86 (dd, J=7.62, 1.05 Hz, 1H), 10.18 (brs, 1H). HRMS (ESI): 286.1073 [M+H+]; calcd for [C$_{16}$H$_{15}$NO$_4$+H+] 286.1079.

2-((4-(3-hydroxypropyl)phenyl)carbamoyl)benzoic acid

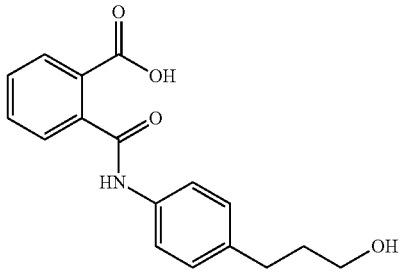 [SMILES: O=C(O)c1ccccc1C(=O)Nc1ccc(CCCO)cc1]

The desired derivative was obtained as bright yellow oil after purification on silica. Rf (CHCl$_3$/MeOH: 12/1): 0.3. $^1$H-NMR (400 MHz, (CD$_3$)$_2$SO): δ 0.98 (t, J=6.6 Hz, 2H), 1.72 (sext., J=6.6 Hz, 2H), 3.9 (d, J=6.6 Hz, 2H), 6.8 (dt, J=9.0, 2.1 Hz, 2H), 7.52 (dd, J=7.5, 1.14 Hz, 2H), 7.56-7.59 (m, 3H), 7.65 (td, J=7.5, 1.3 Hz, 1H), 7.86 (dd, J=7.6, 1.2 Hz, 1H), 10.17 (brs, 1H). HRMS (ESI): 300.1241 [M+H+]; calcd for [C$_{17}$H$_{17}$NO$_4$+H+] 300.1236.

LK55

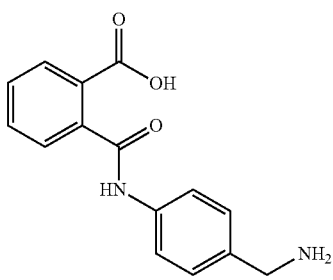 [SMILES: NCc1ccc(NC(=O)c2ccccc2C(=O)O)cc1]

2-((4-(3-(aminomethyl)phenyl)carbamoyl)benzoic acid

The desired derivative was obtained as light yellow oil after purification on silica. Rf (CHCl$_3$/MeOH: 15/1): 0.3. $^1$H-NMR (400 MHz, (CD$_3$)$_2$SO): δ 2.51 (brt, J=1.2 Hz, 2H), 6.87 (d, J=7.6 Hz, 1H), 7.19 (dd, J=8.0, 7.6 Hz, 1H), 7.50 (m, 3H), 7.56 (m, 2H), 7.77 (dd, J=7.2, 1.6 Hz, 1H), 10.2 (brs, 1H), 11.16 (brs, NH$_2$—, 2H). HRMS (ESI): 271.1080 [M+H+]; calcd for [C$_{15}$H$_{14}$N$_2$O$_3$+H+] 271.1083.

LK55b

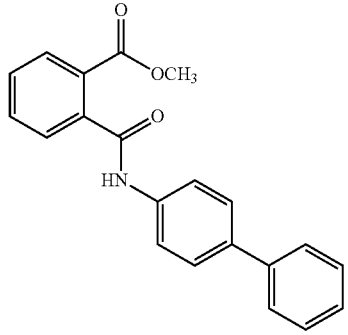 [SMILES: COC(=O)c1ccccc1C(=O)Nc1ccc(-c2ccccc2)cc1]

Methyl 2-([1,1'-biphenyl]-4-ylcarbamoyl)benzoate

The desired derivative was obtained as light yellow oil after purification on silica. Rf CHCl$_3$/MeOH: 8/1): 0.3. $^1$H-NMR (400 MHz, (CD$_3$)$_2$SO): δ 2.33 (s, 3H), 6.58 (d, J=7.5 Hz, 1H), 7.19 (t, J=7.8 Hz, 2H), 7.47-7.53 (m, 4H), 7.54 (m, 2H), 7.63 (dm, J=8.5 Hz, 2H), 7.80 (dd, J=8.5, 1.4 Hz, 2H). HRMS (ESI): 332.1781 [M+H+]; calcd for [C$_{21}$H$_{17}$NO$_3$+H+] 332.1787.

LK22b

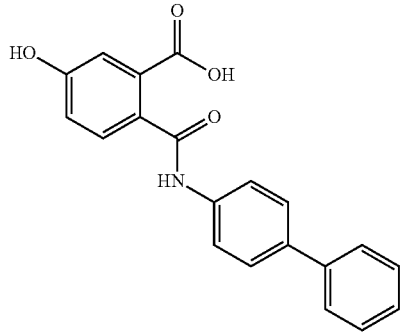 [SMILES: O=C(O)c1cc(O)ccc1C(=O)Nc1ccc(-c2ccccc2)cc1]

2-([1,1'-biphenyl]-4-ylcarbamoyl)-5-hydroxybenzoic acid

The desired derivative was obtained as a grey solid after purification on silica. Rf(CHCl$_3$/MeOH: 9/1): 0.2. $^1$H-NMR (400 MHz, (CD$_3$)$_2$SO): δ 7.29 (d, J=8.2 Hz, 1H), 7.42 (m, 2H), 7.51 (m, 3H), 7.68 (m, 1H), 7.70 (m, 2H), 7.80 (dt, J=8.7, 2.1 Hz, 2H), 7.98 (d, J=8.7 Hz, 1H). HRMS (ESI): 334.1082 [M+H+]; calcd for [C$_{20}$H$_{15}$NO$_4$+H+] 334.1079.

LK5

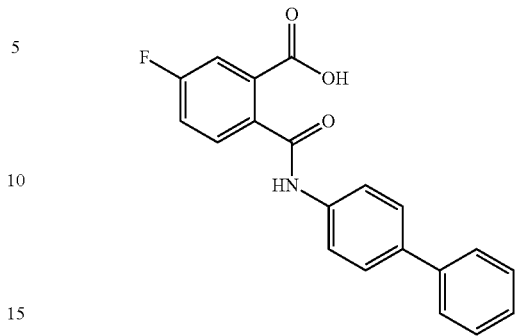

2-([1,1'-biphenyl]-4-ylcarbamoyl)-5-fluorobenzoic acid

The desired derivative was obtained as a grey solid after purification on silica. Rf(CHCl$_3$/MeOH: 9/1): 0.4. $^1$H-NMR (400 MHz, (CD$_3$)$_2$SO): δ 7.34 (tt, J=7.3, 1.2 Hz, 1H), 7.41-7.49 (m, 4H), 7.77 (dm, J=8.7 Hz, 2H), 7.99 (dd, J=8.7, 5.6 Hz, 1H), 10.49 (brs, 1H). HRMS (ESI): 336.1041 [M+H+]; calcd for [C$_{20}$H$_{14}$FNO$_3$+H+] 336.1036.

A01

$^1$H-NMR (300 MHz, (CD$_3$)$_2$SO): δ 11.08 (s, 1H), 8.04 (d, J=7.5 Hz, 1H), 7.87-7.99 (m, 6H), 7.82 (t, J=7.5 Hz, 1H). MS (ESI): 247.90 [M+H+]; calcd for [C$_{15}$H$_9$N$_3$O+H+] 248.08.

A06

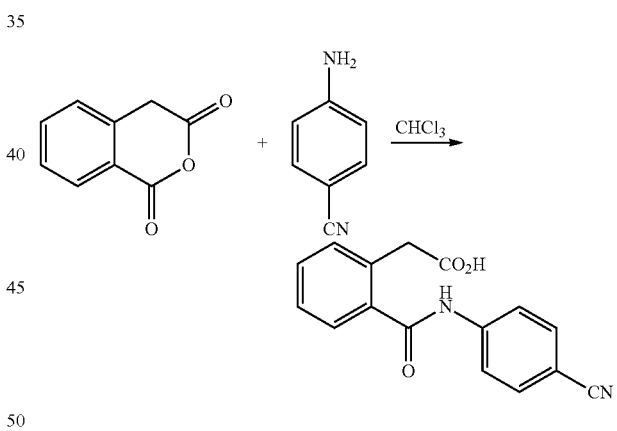

Prepared from Homophthalic anhydride+4-aminobenzonitrile under standard conditions. $^1$H-NMR (300 MHz, (CD$_3$)$_2$SO): δ 10.55 (s, 1H), 7.91 (d, J=6.6 Hz, 1H), 7.77 (m, 4H), 7.55 (t, J=7.2 Hz, 1H), 7.40 (m, 2H), 4.14 (s, 2H). MS (ESI): 280.90 [M+H+]; calcd for [C$_{16}$H$_{12}$N$_2$O$_3$+H+] 281.09.

A09

$^1$H-NMR (300 MHz, (CD$_3$)$_2$SO): δ 8.00 (m, 2H), 7.83 (t, J=7.2 Hz, 1H), 7.72 (t, J=7.5 Hz, 1H), 7.65 (d, J=7.5 Hz, 1H), 7.44 (m, 2H), 6.41 (d, J=8.7 Hz, 2H), 1.95 (s, 3H). MS (ESI): 265.10 [M+H+]; calcd for [C$_{16}$H$_{12}$N$_2$O$_2$+H+] 265.10.

A11

$^1$H-NMR (300 MHz, (CD$_3$)$_2$SO): δ 10.79 (s, 1H), 9.89 (s, 1H), 7.93 (m, 3H), 7.83 (d, J=6.6 Hz, 2H), 7.76 (d, J=5.7 Hz, 1H), 7.56 (t, J=6.0 Hz, 1H), 7.22 (t, J=5.4 Hz, 1H), 3.64 (s, 3H). MS (ESI): 317.95 [M+Na+]; calcd for [C$_{16}$H$_{13}$N$_3$O$_3$+Na+] 318.09.

A12

¹H-NMR (300 MHz, (CD₃)₂SO): δ 10.78 (s, 1H), 9.04 (s, 1H), 8.17 (d, J=8.4 Hz, 1H), 7.82-7.95 (m, 4H), 7.67 (d, J=6.9 Hz, 1H), 7.45 (t, J=7.8 Hz, 1H), 7.07 (t, J=7.2 Hz, 1H), 6.41 (brs, 2H). MS (ESI): 303.05 [M+Na+]; calcd for [C₁₅H₁₂N₄O₂+Na+] 303.09.

A13

¹H-NMR (300 MHz, (CD₃)₂SO): δ 10.91 (brs, 1H), 9.88 (brs, 1H), 7.82-7.94 (m, 5H), 7.52 (m, 2H), 7.26 (brs, 1H), 3.07 (s, 3H). HRMS (ESI): 316.0750 [M+H+]; calcd for [C₁₅H₁₃N₃O₃+H+] 316.0768.

A22

¹H-NMR (300 MHz, (CD₃)₂SO): δ 7.82-7.89 (m, 5H), 7.66 (m, 1H), 7.56 (m, 2H). MS (ESI): 303.05 [M+H+]; calcd for [C₁₄H₁₀N₂O₄S+H+] 303.04.

A23

¹H-NMR (300 MHz, (CD₃)₂SO): δ 11.03 (s, 1H), 8.00 (m, 1H), 7.90 (m, 4H), 7.75 (m, 3H), 7.18 (s, 2H). MS (ESI): 323.90 [M+Na+]; calcd for [C₁₄H₁₁N₃O₃S+Na+] 324.04.

A24

¹H-NMR (300 MHz, (CD₃)₂SO): δ 10.96 (s, 1H), 7.68-7.92 (m, 8H), 6.99 (m, 1H). MS (ESI): 338.06 [M+Na+]; calcd for [C₁₅H₁₃N₃O₃S+Na+] 337.95.

B02

¹H-NMR (300 MHz, (CD₃OD): δ 7.99 (s, 1H), 7.85-7.92 (m, 4H), 7.70 (d, J=6.3 Hz, 2H). MS (ESI): 290.00 [M−1]; calcd for [C₁₄H₁₀N₂O₄S−1] 290.06.

B03

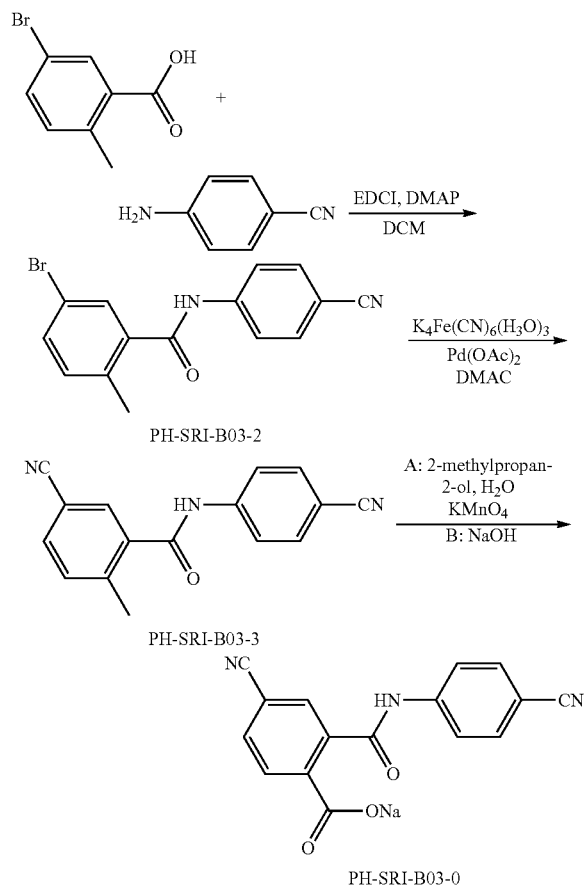

Into a 50-mL round-bottom flask, was placed a solution of 5-bromo-2-methylbenzoic acid (1.5 g, 6.98 mmol, 1.00 equiv) in dichloromethane (15 mL), 4-aminobenzonitrile (820 mg, 6.94 mmol, 1.00 equiv), EDCI (2 g, 10.43 mmol, 1.50 equiv), 4-dimethylaminopyridine (1.28 g, 10.48 mmol, 1.50 equiv). The resulting solution was stirred overnight at room temperature. The resulting mixture was concentrated under vacuum. The residue was dissolved in 100 mL of ethyl acetate. The resulting mixture was washed with 3×30 mL of hydrogen chloride (2.4 mol/L) and 2×30 mL of water. The resulting mixture was washed with 2×30 mL of sodium bicarbonate (aq.) and 2×30 mL of brine. The mixture was dried over anhydrous sodium sulfate and concentrated under vacuum. This resulted in 1.93 g (88%) of 5-bromo-N-(4-cyanophenyl)-2-methylbenzamide as a light yellow solid.

Into a 100-mL round-bottom flask purged and maintained with an inert atmosphere of nitrogen, was placed a solution of 5-bromo-N-(4-cyanophenyl)-2-methylbenzamide (1 g, 3.17 mmol, 1.00 equiv) in DMAC (5 mL), bis(dipotassium) ironhexacarbonitrile trihydrate (337 mg, 0.80 mmol, 0.25 equiv), sodium carbonate (336 mg, 3.17 mmol, 1.00 equiv), Pd(OAc)₂ (23 mg, 0.10 mmol, 0.03 equiv). The resulting solution was stirred for 4 h at 120° C. in an oil bath. The reaction mixture was cooled. The resulting solution was diluted with 60 mL of ethyl acetate. The resulting mixture was washed with 1×40 mL of brine. The resulting solution was dried over sodium sulfate and concentrated under vacuum. This resulted in 0.65 g (78%) of 5-cyano-N-(4-cyanophenyl)-2-methylbenzamide as a light brown solid.

Into a 50-mL round-bottom flask, was placed 5-cyano-N-(4-cyanophenyl)-2-methylbenzamide (300 mg, 1.15 mmol, 1.00 equiv), 2-methylpropan-2-ol (12 mL), water (12 mL). To this was added tetraoxo(potassio)manganese (908 mg, 5.75 mmol, 5.00 equiv) in several batches at 100° C. in 27 mins. The resulting solution was stirred for 6.5 h at 100° C. in an oil bath. The reaction mixture was cooled to 40 degree C. with a water bath. The pH value of the solution was adjusted to 2 with aqueous hydrogen chloride (2.4 mol/L). The resulting solution was extracted with 4×50 ml of ethyl acetate and the organic layers combined and concentrated under vacuum. Aqueous sodium hydroxide (1 mol/L) was employed to adjust the pH to 9. The crude product (200 mg) was purified by Prep-HPLC with the following conditions (1#-Pre-HPLC-001 (SHIMADZU)): Column, SunFire Prep C18, 19*150 mm 5 um; mobile phase, Water with 50 mmolNH₄HCO₃ and CH₃CN (25% CH₃CN up to 30% in 15 min, up to 100% in 2 min, down to 25% in 1 min); Detector, Waters2545 UvDector 254&220 nm. 8.5 mg product was obtained. This resulted in 8.5 mg (2%) of sodium 4-cyano-2-[(4-cyanophenyl)carbamoyl]benzoate as a white solid.

¹H-NMR (300 MHz, (CD₃OD): δ 7.99 (s, 1H), 7.88 (m, 4H), 7.70 (d, J=6.3 Hz, 2H). MS (ESI): 289.90 [M-Na-1]; calcd for [C₁₆H₉N₃NaO₃—Na-1] 289.06.

B10

¹H-NMR (300 MHz, (CD₃)₂SO): δ 13.49 (brs, 2H), 10.92 (1H), 8.47 (s, 1H), 8.20 (m, 1H), 7.85 (m, 4H), 7.71 (d, J=7.8 Hz, 1H). MS (ESI): 281.90 [M+H+]; calcd for [C₁₆H₁₀N₂O₅+H+] 282.09. MS (ESI): 311.00 [M+H+]; calcd for [C₁₆H₁₁N₃O₃+H+] 311.07.

B12

¹H-NMR (300 MHz, (CD₃)₂SO): δ 8.04 (m, 1H), 7.67-7.98 (m, 4H), 7.32-7.62 (m, 2H). MS (ESI): 333.40 [M+Na+]; calcd for [C₁₆H₁₀N₂O₅+Na+] 333.05.

B19

¹H-NMR (300 MHz, (CD₃)₂SO): δ 13.61 (brs, 1H), 10.94 (s, 1H), 9.10 (s, 1H), 8.89 (d, J=4.8 Hz, 1H), 7.83 (s, 4H), 7.63 (d, J=4.8 Hz, 1H). MS (ESI): 268.00 [M+H+]; calcd for [C₁₄H₉N₃O₃+H+] 268.07.

B20

¹H-NMR (300 MHz, (CD₃)₂SO): δ 13.48 (brs, 1H), 11.04 (s, 1H), 8.82 (m, 2H), 8.26 (dd, 7.8, 1.2 Hz, 1H), 7.97 (m, 2H), 7.85 (m, 2H), 7.73 (m, 1H). MS (ESI): 268.00 [M+H+]; calcd for [$C_{14}H_9N_3O_3$+H+] 268.07.

B32

¹H-NMR (300 MHz, (CD₃)₂SO): δ 11.83 (brs, 1H), 7.67 (m, 6H), 7.50 (m, 2H), 7.32-7.40 (m, 2H), 7.08-7.20 (m, 3H). MS (ESI): 365.05 [M+Na+]; calcd for [$C_{21}H_{14}N_2O_3$+H+] 365.09.

MS 01

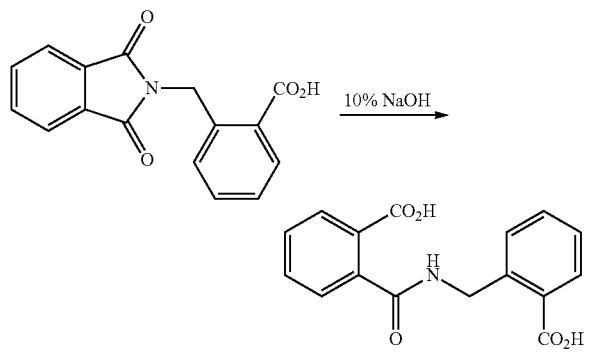

2-(N-Phthalimidomethyl)benzoic acid (as prepared by Bornstein, J. et al, Organic Syntheses, 38, No pp. given; 1958) was dissolved in 10% NaOH solution and stirred at room temperature overnight. The pH value of the solution was adjusted to 2 with aqueous hydrogen chloride (2.4 mol/L). The resulting solution was extracted with 4×50 ml of ethyl acetate and the organic layers combined and concentrated under vacuum. Aqueous sodium hydroxide (1 mol/L) was employed to adjust the pH to 9. The crude product was purified by Prep-HPLC to give the title compound. ¹H-NMR (300 MHz, (CD₃)₂SO): δ 13.00 (s, 1H), 8.79 (t, J=6.0 Hz, 1H), 7.90 (d, J=6.9 Hz, 1H), 7.54-7.82 (m, 6H), 7.38 (t, J=7.5 Hz, 1H), 4.79 (d, J=5.7 Hz, 2H). MS (ESI): 300.00 [M+H+]; calcd for [$C_{16}H_{13}NO_5$+H+] 300.09.

MS02

¹H-NMR (300 MHz, (CD₃)₂SO): δ 12.95 (s, 2H) 8.93 (t, J=6.0 Hz, 1H), 7.97 (s, 1H), 7.47-7.87 (m, 7H), 4.51 (d, J=5.7 Hz, 2H). MS (ESI): 322.00 [M+Na+]; calcd for [$C_{16}H_{13}NO_5$+Na+] 322.07.

MS04

¹H-NMR (300 MHz, (CD₃)₂SO): δ 13.01 (brs, 1H), 9.03 (t, J=5.7 Hz, 1H), 7.83 (t, J=8.1 Hz, 2H), 7.46-7.80 (m, 6H), 4.62 (d, J=6.0 Hz, 2H). MS (ESI): 281.00 [M+H+]; calcd for [$C_{16}H_{12}N_2O_3$+H+] 281.09.

MS06

¹H-NMR (300 MHz, (CD₃)₂SO): δ 12.99 (brs, 1H), 8.95 (t, J=6.0 Hz, 1H), 7.95 (m, 3H), 7.49-7.83 (m, 5H), 4.53 (d, J=6.0 Hz, 2H). MS (ESI): 280.85 [M+H+]; calcd for [$C_{16}H_{12}N_2O_3$+H+] 281.09.

MS11

¹H-NMR (300 MHz, (CD₃OD): δ 7.94-8.03 (m, 3H), 7.86 (m, 2H), 7.50 (m, 2H), 7.38 (m, 1H). MS (ESI): 281.25 [M+H+]; calcd for [$C_{16}H_{12}N_2O_3$+H+] 281.09.

MS14

¹H-NMR (300 MHz, (CD₃)₂SO): δ 11.13 (s, 1H), 8.48 (d, J=6.3 Hz, 1H) 7.94 (m, 3H), 7.58 (t, J=5.4 Hz, 1H), 7.49 (d, J=6.3 Hz, 2H), 7.15 (t, J=5.7 Hz, 1H), 3.87 (s, 2H). MS (ESI): 321.90 [M+Na+]; calcd for [$C_{16}H_{13}NO_5$+Na+] 322.07.

MS15

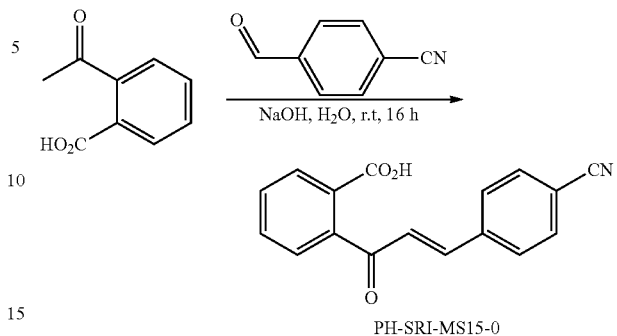

Into a 50-mL round-bottom flask, was placed 2-acetylbenzoic acid (1.64 g, 9.99 mmol, 1.00 equiv), ethanol (5 mL), 4-formylbenzonitrile (1.31 g, 9.99 mmol, 1.00 equiv). To this was added sodium hydroxide(aq.) (10 mL, 1.5N) with an ice/water bath. The resulting solution was stirred for 16 h at room temperature. The reaction was then quenched by the addition of 20 mL of water. The pH value of the solution was adjusted to 2-3 with hydrogen chloride (4 mol/L). The resulting solution was extracted with 3×20 mL of dichloromethane and the organic layers combined. The resulting mixture was washed with 1×30 mL of H2O. The mixture was dried over anhydrous sodium sulfate and concentrated under vacuum. The crude product (250 mg) was purified by Prep-HPLC with the following conditions (l#-Pre-HPLC-006(Waters)): Column, SunFire Prep C18, 19*150 mm 5 um; mobile phase, WATER WITH 0.5% TFA and CH3CN (20% CH3CN up to 60% in 10 min, up to 100% in 2 min); Detector, uv 254/220 nm. 16.2 mg product was obtained. This resulted in 16.2 mg (1%) of 2-[(2E)-3-(4-cyanophenyl)prop-2-enoyl]benzoic acid as a white solid. 1H-NMR (300 MHz, (CD₃OD): δ 8.07 (m, 1H), 7.50-7.77 (m, 8H), 7.24 (m, 2H). MS (ESI): 278.15 [M+H+]; calcd for [$C_{17}H_{11}NO_3$+H+] 278.08.

MS16

¹H-NMR (300 MHz, (CD₃)₂SO): δ 13.10 (brs, 1H), 7.96 (m, 3H), 7.83 (m, 2H), 7.64-7.76 (m, 2H), 7.52 (m, 1H), 7.28 (m, 2H). MS (ESI): 297.25 [M+H+]; calcd for [$C_{17}H_{12}O_5$+H+] 297.08.

MS 17-1

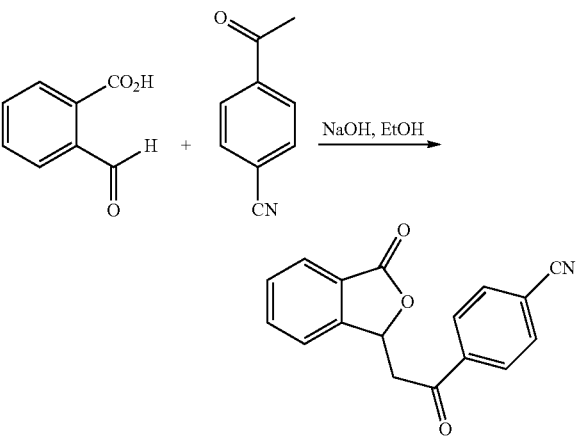

To a solution of 2-carboxybenzaldehyde (150 mg, 1 mmol) in 2M NaOH in water/ethanol (1:1, 5 mL) was added 4′-cyanoacetophenone (145 mg, 1 mmol) dropwise at 0° C. The resultant mixture was stirred for 48 h at room temperature. The reaction mixture was diluted with ethyl acetate and subsequently washed with brine. The organic extracts were dried over anhydrous sodium sulfate and concentrated under vacuum with subsequent purification by column chromatography to give the title compound. $^1$H-NMR (300 MHz, (CD$_3$)$_2$SO): δ 8.15 (d, J=6.0 Hz, 2H), 8.04 (d, J=6.3 Hz, 2H), 7.87 (d, J=5.7 Hz, 1H), 7.81 (t, J=5.4 Hz, 1H), 7.74 (d, J=5.7 Hz, 1H), 7.63 (t, J=5.7 Hz, 1H), 6.12 (m, 1H), 3.77-3.98 (m, 2H). MS (ESI): 275.85 [M-1]; calcd for [C$_{17}$H$_{11}$NO$_3$-1] 276.07.

MS18-1

$^1$H-NMR (300 MHz, (CD$_3$)$_2$SO): δ 13.35 (brs, 1H), 8.08 (m, 4H), 7.75-7.88 (m, 3H), 7.62 (m, 1H), 6.13 (m, 1H), 3.93 (m, 2H). HRMS (ESI): 297.0766 [M+H+]; calcd for [C$_{17}$H$_{12}$O$_5$+H+] 297.0757.

MS 21

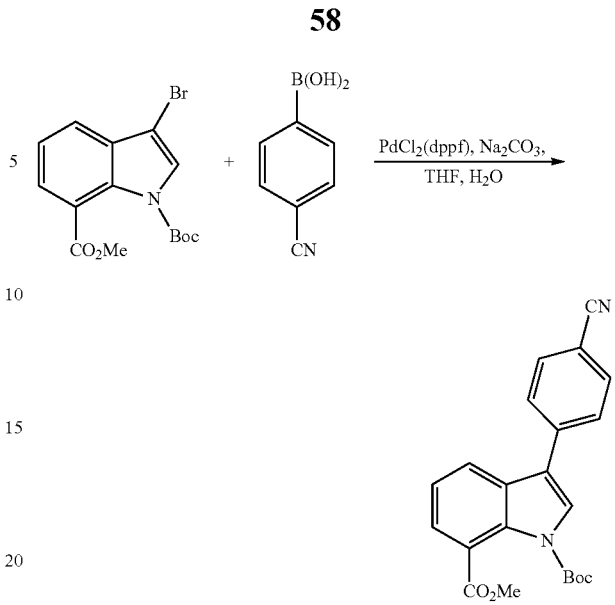

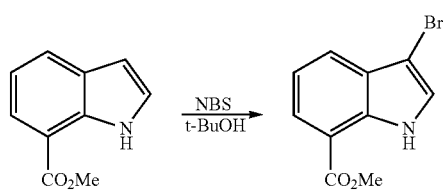

(The title compound was prepared according to the procedure of Nozawa, Eisuke et al from PCT Int. Appl., 2009005076, 8 Jan. 2009.) To a mixture of methyl 1H-indole-7-carboxylate (6.00 g, 34.25 mmol) and tert-butanol (300 mL) was added N-bromosuccinimide (3.30 g, 18.5 mmol) portionwise at room temperature. This solution was stirred for 2 h at room temperature. The reaction mixture was concentrated under reduced pressure. To the residue was added a saturated sodium bicarbonate solution followed by extraction with ethyl acetate. The organic layer was dried over sodium sulfate, filtered, and then concentrated under reduced pressure. The crude product was purified by flash column chromatography to give the title compound (4.2 g, 48%).

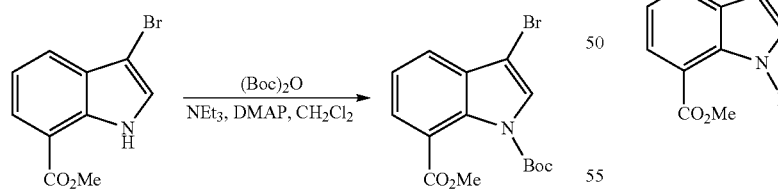

To a solution of methyl 3-bromo-1H-indole-7-carboxylate (4.0 g, 15.75 mmol) and DMAP (38.5 mg, 0.315 mmol) in CH$_2$Cl$_2$ (15 mL) was added di-tert-buty dicarbonate (3.78 g, 17.33 mmol). The reaction was stirred for 3 h at room temperature. The reaction was quenched with 1N HCl. The organic layer was extracted with ethyl acetate, dried over sodium sulfate, filtered, and then concentrated under reduced pressure. The crude product was purified by flash column chromatography to give the title compound (5.03 g, 90%).

To a solution of 1-tert-butyl 7-methyl 3-(4-cyanophenyl)-1H-indole-1,7-dicarboxylate (753.0 mg, 2 mmol) 4-cyanophenylboronic acid (441.0 mg, 3.0 mmol), sodium carbonate (318.0 mg, 3.0 mmol) in THF and H$_2$O (3:1, 80 mL) was added PdCl$_2$(dppf) (0.2 mmol, 146.3 mg). The reaction mixture was heated at reflux for 10 h. The reaction was quenched by addition of ethyl acetate and sodium bicarbonate. The organic layer was separated, washed with brine, dried over sodium sulfate, filtered, and then concentrated under reduced pressure. The crude product was purified by flash column chromatography to give the title compound (587.2 mg, 78%).

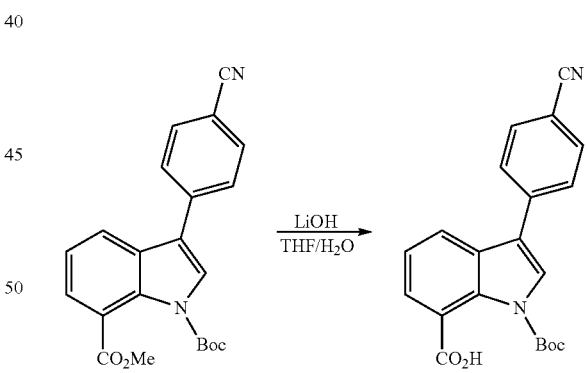

1-tert-butyl 7-methyl 3-(4-cyanophenyl)-1H-indole-1,7-dicarboxylate (376.4 mg, 1 mmol) was added to a solution of 1M LiOH.H$_2$O in THF and H$_2$O (1:1, 10 mL). The reaction mixture was stirred at room temperature for 12 h. The aqueous layer was first washed with ethyl acetate and then acidified with 4N HCl. The aqueous layer was then extracted with ethyl acetate. The organic layer was dried over sodium sulfate, filtered, and then concentrated under reduced pressure. The crude product was used in the next step without further purification.

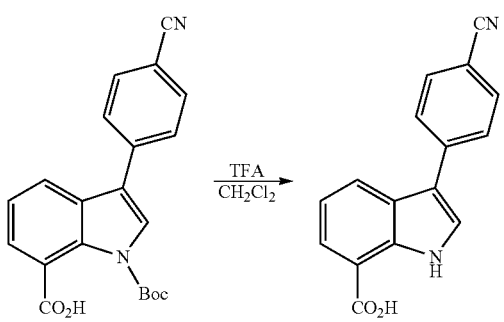

Crude 1-(tert-butoxycarbonyl)-3-(4-cyanophenyl)-1H-indole-7-carboxylic acid (300 mg) was added to a 10% solution of trifluoroacetic acid in $CH_2Cl_2$ (10 mL) at 0° C. The reaction mixture was warmed to room temperature and stirred for one hour. The solvent was removed under reduced pressure. The crude product was purified by Prep-HPLC to give the title compound. 1H-NMR (300 MHz, $(CD_3)_2SO$): δ 13.16 (brs, 1H), 11.59 (s, 1H), 8.22 (d, J=8.1 Hz, 1H), 7.86-7.97 (m, 6H), 7.29 (t, J=7.5 Hz, 1H). MS (ESI): 261.00 [M-1]; calcd for $[C_{16}H_{10}N_2O_5\text{-}1]$ 261.07.

MS26

$^1$H-NMR (300 MHz, $(CD_3)_2SO$): δ 8.14 (d, J=6.6 Hz, 2H), 7.92 (d, J=6.6 Hz, 2H), 7.83 (d, J=5.7 Hz, 1H), 7.71 (m, 2H), 7.57 (t, J=5.1 Hz, 1H), 5.09 (s, 2H). MS (ESI): 235.00 [M+H+]; calcd for $[C_{15}H_{10}N_2O+H+]$ 235.09.

MS28

$^1$H-NMR (300 MHz, $(CD_3)_2SO$): δ 7.96-8.07 (m, 4H), 7.86 (s, 2H), 7.74 (d, J=8.4 Hz, 2H).

MS29

$^1$H-NMR (300 MHz, $(CD_3)_2SO$): δ 8.10 (d, J=8.4 Hz, 2H), 7.93-8.03 (m, 4H), 7.60 (d, J=8.4 Hz, 2H). MS (ESI): 266.00 [M-1 calcd for $[C_{15}H_{19}NO_4\text{-}1]$ 266.05.

MS 39

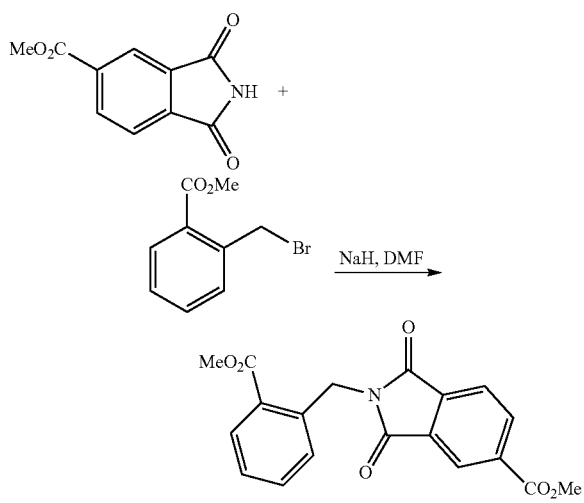

To a solution of NaH (60% dispersion in oil, 1.2 eq) in DMF (10 mL) was added methyl 1,3-dioxoisoindoline-5-carboxylate (353 mg, 1.00 mmol) (as prepared by Mazzocchi, P. H. et al Journal of Organic Chemistry, 48(18), 2981-9; 1983) dropwise at 0° C. The solution was warmed to room temperature and stirred for one hour. Methyl 2-(bromomethyl)benzoate (275 mg, 1.2 mmol) was subsequently added dropwise and the reaction mixture stirred overnight. The mixture was diluted with ethyl acetate and washed with brine. The organic extracts were dried over anhydrous sodium sulfate and concentrated under vacuum to give an oil which was used in the next step without further purification. $^1$H-NMR (300 MHz, $(CD_3)_2SO$): δ 8.37 (m, 2H), 7.92 (t, J=7.8 Hz, 2H), 7.37 (t, J=7.8 Hz, 1H), 7.27 (t, J=7.8 Hz, 1H), 7.07 (d, J=7.8 Hz, 1H), 5.22 (s, 2H). MS (ESI): 347.80 [M+Na+]; calcd for $[C_{17}H_{11}NO_6+Na+]$ 348.05.

N01

$^1$H-NMR (300 MHz, $(CD_3)_2SO$): δ 13.03 (brs, 1H), 11.00 (brs, 1H), 8.47 (d, J=6.0 Hz, 2H), 7.92 (d, J=7.2 Hz, 1H), 7.64 (m, 5H). MS (ESI): 242.90 [M+H+]; calcd for $[C_{13}H_{10}N_2O_3+H+]$ 243.08.

N04

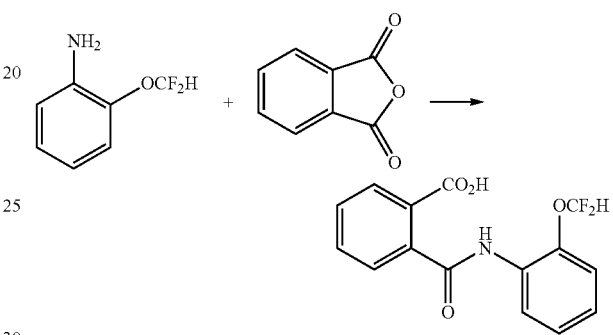

Prepared from 2-(Difluoromethoxy)aniline and phthalic anhydride under standard conditions. 1H-NMR (300 MHz, $(CD_3)_2SO$): δ 9.95 (s, 1H), 7.88 (m, 2H), 7.52-7.71 (m, 3H), 7.30 (m, 3H) 7.09 (s, 1H). MS (ESI): 307.95 [M+H+]; calcd for $[C_{15}H_{11}F_2NO_4+H+]$ 308.07.

N05

$^1$H-NMR (300 MHz, $(CD_3)_2SO$): δ 13.09 (brs, 1H), 10.54 (s, 1H), 7.91 (d, J=6.9 Hz, 1H), 7.48-7.90 (m, 5H), 7.39 (t, J=8.1 Hz, 1H), 7.23 (s, 1H), 6.91 (d, J=6.6 Hz, 1H). MS (ESI): 307.85 [M+H+]; calcd for $[C_{15}H_{11}F_2NO_4+H+]$ 308.07.

N08

$^1$H-NMR (300 MHz, $(CD_3)_2SO$): δ 13.18 (brs, 1H), 10.66 (brs, 1H), 8.42 (brs, 1H), 7.69-8.02 (m, 7H), 2.62 (s, 3H). MS (ESI): 306.05 [M+Na+]; calcd for $[C_{16}H_{13}NO_4+Na+]$ 306.07.

N09

$^1$H-NMR (300 MHz, $(CD_3)_2SO$): δ 13.11 (brs, 1H), 10.70 (s, 1H), 7.83-7.99 (m, 5H), 7.58-7.72 (m, 3H), 2.52 (m, 3H). MS (ESI): 284.05 [M+H+]; calcd for $[C_{16}H_{13}NO_4+H+]$ 284.09.

N10

$^1$H-NMR (300 MHz, $(CD_3)_2SO$): δ 13.12 (brs, 1H), 12.23 (s, 1H), 8.62 (d, J=8.1 Hz, 1H), 8.34 (s, 1H), 7.22-7.89 (m, 7H), 7.17 (t, J=6.9 Hz, 1H). MS (ESI): 285.00 [M+H+]; calcd for $[C_{15}H_{12}N_2O_4+H+]$ 285.09.

N11

$^1$H-NMR (300 MHz, $(CD_3)_2SO$): δ 13.02 (brs, 1H), 10.46 (s, 1H), 8.20 (s, 1H), 7.82-7.94 (m, 3H), 7.57-7.71 (m, 4H), 7.35-7.44 (m, 2H). MS (ESI): 307.25 [M+Na+]; calcd for $[C_{15}H_{12}N_2O_4+Na+]$ 307.07.

N13

$^1$H-NMR (300 MHz, $(CD_3)_2SO$): δ 13.40 (brs, 1H), 11.55 (s, 1H), 8.61 (d, J=6.3 Hz, 1H), 8.02 (m, 2H), 7.23-7.88 (m, 4H), 7.20 (t, J=5.4 Hz, 1H). MS (ESI): 308.20 [M+Na+]; calcd for $[C_{15}H_{11}NO_5+Na+]$ 308.05.

N14

$^1$H-NMR (300 MHz, (CD$_3$)$_2$SO): δ 13.02 (brs, 2H), 10.53 (s, 1H), 8.38 (s, 1H), 7.89 (t, J=6.0 Hz, 2H), 7.56-7.69 (m, 4H), 7.46 (t, J=5.7 Hz, 1H). MS (ESI): 286.20 [M+H+]; calcd for [C$_{15}$H$_{11}$NO$_5$+H+] 286.07

N17

$^1$H-NMR (300 MHz, (CD$_3$)$_2$SO): δ 13.00 (brs, 1H), 10.65 (s, 1H), 8.34 (s, 1H), 7.90 (d, J=5.7 Hz, 1H), 7.77 (m, 1H) 7.39-7.69 (m, 5H), 7.32 (s, 2H). MS (ESI): 320.85 [M+H+]; calcd for [C$_{14}$H$_{12}$N$_2$O$_5$S+H+] 321.05.

N19

$^1$H-NMR (300 MHz, (CD$_3$)$_2$SO): δ 13.13 (brs, 1H), 10.71 (s, 1H), 8.18 (s, 1H), 7.90-7.94 (m, 2H), 7.55-7.73 (m, 5H). MS (ESI): 267.00 [M+H+]; calcd for [C$_{15}$H$_{10}$N$_2$O$_3$+H+] 267.08.

N20

$^1$H-NMR (300 MHz, (CD$_3$)$_2$SO): δ 13.10 (brs, 1H), 9.76 (s, 1H), 7.88 (d, J=7.8 Hz, 1H), 7.57-7.71 (m, 4H), 7.45 (d, J=7.2 Hz, 1H), 7.19-7.32 (m, 2H), 5.29 (brs, 1H), 4.61 (s, 2H). MS (ESI): 293.90 [M+Na+]; calcd for [C$_{15}$H$_{13}$NO$_4$+Na+] 294.07.

N24

$^1$H-NMR (300 MHz, (CD$_3$)$_2$SO): δ 8.05 (m, 2H), 7.45-7.74 (m, 5H), 7.28 (m, 1H), 4.23 (s, 2H), 2.77 (s, 3H). MS (ESI): 284.90 [M+H+]; calcd for [C$_{16}$H$_{16}$N$_2$O$_3$+H+] 285.12.

N26

$^1$H-NMR (300 MHz, (CD$_3$)$_2$SO): δ 12.98 (brs, 1H), 10.24 (s, 1H), 7.88 (d, J=6.6 Hz, 1H), 7.53-7.87 (m, 5H), 7.17 (d, J=8.4 Hz, 2H), 3.59 (t, J=6.9 Hz, 2H), 2.70 (t, J=7.2 Hz, 2H). MS (ESI): 308.25 [M+Na+]; calcd for [C$_{16}$H$_{15}$NO$_4$+Na+] 308.09.

N28

$^1$H-NMR (300 MHz, (CD$_3$)$_2$SO): δ 12.84 (brs, 1H), 10.13 (s, 1H), 7.86 (d, J=7.2 Hz, 1H), 7.52-7.68 (m, 5H), 6.93 (d, J=9.0 Hz, 2H), 3.76 (m, 4H), 3.07 (m, 4H). MS (ESI): 326.90 [M+H+]; calcd for [C$_{18}$H$_{18}$N$_2$O$_4$+H+] 327.13.

N30

$^1$H-NMR (300 MHz, (CD$_3$)$_2$SO): δ 9.41 (brs, 1H), 7.60 (m, 1HO, 7.51 (m, 1H), 7.40 (m, 2H), 3.74 (m, 1H), 2.73 (m, 1H), 2.03 (m, 2H), 1.87 (m, 2H), 1.60 (m, 2H), 1.36 (m, 2H). MS (ESI): 295.10 [M+Na+]; calcd for [C$_{15}$H$_{16}$N$_2$O$_3$+Na+] 295.11.

N31

$^1$H-NMR (300 MHz, (CD$_3$)$_2$SO): δ 7.67 (d, J=5.7 Hz, 1H), 7.27-7.36 (m, 3H), 1.99 (m, 1H), 1.47-1.64 (m, 8H). MS (ESI): 314.30 [M+Na+]; calcd for [C$_{15}$H$_{17}$NO$_5$+Na+] 314.10.

N33

$^1$H-NMR (300 MHz, (CD$_3$)$_2$SO): δ 7.54 (m, 1H), 7.26-7.52 (m, 3H), 3.07 (d, J=7.2 Hz, 2H), 2.28 (m, 1H), 1.80 (m, 2H), 1.38-1.58 (m, 5H), 1.23 (m, 2H). MS (ESI): 306.10 [M+H+]; calcd for [C$_{16}$H$_{19}$NO$_5$+H+] 306.13.

N34

$^1$H-NMR (300 MHz, (CD$_3$)$_2$SO): δ 7.81 (m, 1H), 7.50-7.80 (m, 3H), 6.74 (s, 2H). MS (ESI): 232.10 [M+H+]; calcd for [C$_{11}$H$_9$N$_3$O$_3$+H+] 232.07.

N35

$^1$H-NMR (300 MHz, (CD$_3$)$_2$SO): δ 7.95 (d, J=7.2 Hz, 1H), 7.82 (m, 2H), 7.42-7.52 (m, 3H), 7.09 (s, 1H). MS (ESI): 232.90 [M+H+]; calcd for [C$_{11}$H$_8$N$_2$O$_4$+H+] 233.06.

N38

$^1$H-NMR (300 MHz, (CD$_3$)$_2$SO): δ 13.16 (brs, 1H), 11.81 (s, 1H), 8.41 (s, 1H), 7.93 (d, J=7.8 Hz, 1H), 7.57-7.73 (m, 5H), 7.45 (m, 2H), 7.35 (m, 1H). MS (ESI): 309.00 [M+H+]; calcd for [C$_{17}$H$_{12}$N$_2$O$_4$+H+] 309.09.

N39

$^1$H-NMR (300 MHz, (CD$_3$)$_2$SO): δ 7.87-8.05 (m, 4H), 7.64 (s, 1H), 7.43-7.58 (m, 4H), 7.34 (t, J=7.5 Hz, 1H). MS (ESI): 325.00 [M+H+]; calcd for [C$_{17}$H$_{12}$N$_2$O$_3$S+H+] 325.06.

N42

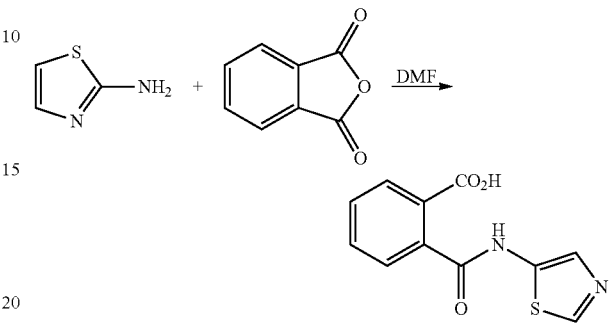

Prepared from 2-Aminothiazole+phthalic anhydride under standard conditions. $^1$H-NMR (300 MHz, (CD$_3$)$_2$SO): δ 13.07 (brs, 1H), 11.78 (s, 1H), 8.63 (s, 1H), 7.93 (m, 1H), 7.58-7.91 (m, 4H). MS (ESI): 248.85 [M+H+]; calcd for [C$_{11}$H$_8$N$_2$O$_3$S+H+] 249.03.

N45

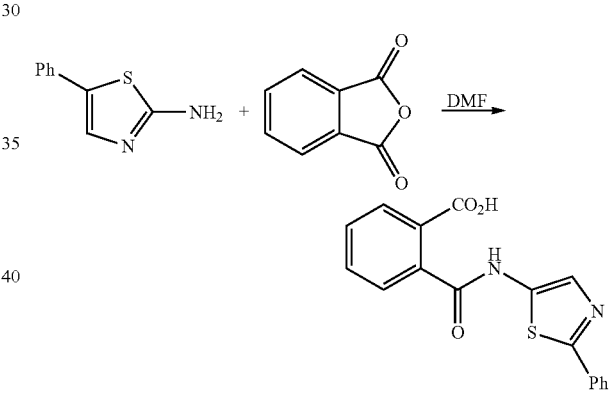

2-Amino-4-phenylthiazole+phthalic anhydride under standard conditions. $^1$H-NMR (300 MHz, (CD$_3$)$_2$SO): δ 13.16 (brs, 1H), 11.90 (s, 1H), 7.93 (m, 3H), 7.62-7.92 (m, 4H), 7.42-7.53 (m, 3H). MS (ESI): 325.00 [M+H+]; calcd for [C$_{17}$H$_{12}$N$_2$O$_3$S+H+] 325.06.

N50

$^1$H-NMR (300 MHz, (CD$_3$)$_2$SO): δ 8.61 (d, J=4.8 Hz, 2H), 7.84 (d, J=7.5 Hz, 1H), 7.50-7.62 (m, 3H), 7.17 (t, J=4.8 Hz, 1H). MS (ESI): 243.85 [M+H+]; calcd for [C$_{12}$H$_9$N$_3$O$_3$+H+] 244.07.

N52

$^1$H-NMR (300 MHz, (CD$_3$)$_2$SO): δ 13.12 (brs, 1H), 11.22 (s, 1H), 9.43 (s, 1H), 8.42 (m, 2H), 7.91 (m, 1H), 7.57-7.69 (m, 3H). MS (ESI): 243.85 [M+H+]; calcd for [C$_{12}$H$_9$N$_3$O$_3$+H+] 244.07.

PA02

$^1$H-NMR (300 MHz, (CD$_3$)$_2$SO): δ 13.07 (brs, 1H), 11.14 (s, 1H), 10.56 (s, 1H), 8.97 (brs, 1H), 7.92 (d, J=7.2 Hz, 1H), 7.57-7.77 (m, 7H). MS (ESI): 300.95 [M+H+]; calcd for [C$_{15}$H$_{12}$N$_2$O$_5$+H+] 301.08.

PA06

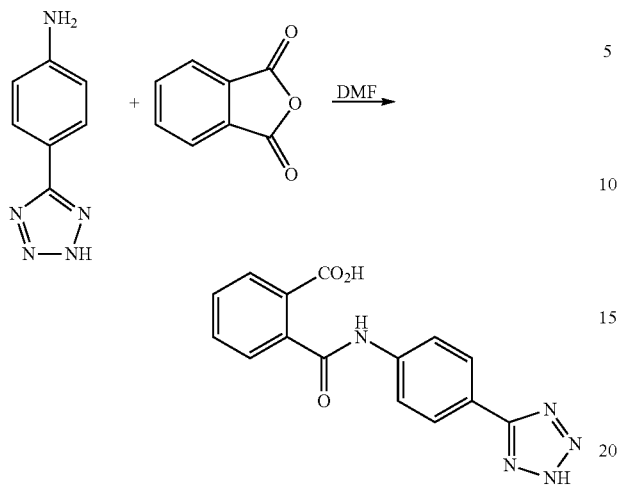

Prepared from 5-(4-Aminophenyl)tetrazole+phthalic anhydride under standard conditions. $^1$H-NMR (300 MHz, $(CD_3)_2SO$): δ 13.11 (brs, 1H), 10.68 (s, 1H), 8.05 (d, J=8.7 Hz, 2H), 7.92 (d, J=8.1 Hz, 3H), 7.59-7.70 (m, 3H). MS (ESI): 310.25 [M+H+]; calcd for $[C_{15}H_{11}N_5O_3+H+]$ 310.09.

PA07

$^1$H-NMR (300 MHz, $(CD_3)_2SO$): δ 10.39 (s, 1H), 8.92 (m, 2H), 8.57 (m, 1H), 8.05 (m, 2H), 7.87 (m, 1H), 7.54-7.76 (m, 8H) (1:1 complex with pyridine). MS (ESI): 320.05 [M−1]; calcd for $[C_{14}H_{11}NO_6S-1]$ 320.03.

PA08

$^1$H-NMR (300 MHz, $CD_3OD$): δ 8.06 (d, J=7.2 Hz, 1H), 7.78 (m, 4H), 7.56-7.70 (m, 3H). MS (ESI): 321.95 [M+H+]; calcd for $[C_{14}H_{12}NO_6P+H+]$ 322.05.

PM02

$^1$H-NMR (300 MHz, $(CD_3)_2SO$): δ 13.03 (brs, 1H), 10.37 (s, 1H), 7.87 (d, J=6.9 Hz, 1H), 7.55-7.71 (m, 5H), 7.40 (t, J=8.1 Hz, 2H) 7.29 (t, J=7.8 Hz, 2H), 6.91-7.02 (m, 3H), 5.05 (s, 2H). MS (ESI): 370.30 [M+Na+]; calcd for $[C_{21}H_{17}NO_4+Na+]$ 370.11.

PM05

$^1$H-NMR (300 MHz, $(CD_3)_2SO$): δ 13.08 (brs, 1H), 10.52 (s, 1H), 8.66 (m, 1H), 8.10 (d, J=8.7 Hz, 2H), 7.83-7.97 (m, 5H), 7.59-7.72 (m, 3H), 7.32 (m, 1H). MS (ESI): 318.85 [M+H+]; calcd for $[C_{19}H_{14}N_2O_3+H+]$ 319.11.

PM10

$^1$H-NMR (300 MHz, $(CD_3)_2SO$): δ 12.50 (brs, 1H), 7.63-7.76 (m, 4H), 7.47 (m, 2H), 7.21 (d, J=8.4 Hz, 2H), 6.40 (t, J=6.0 Hz, 1H), 5.52 (s, 2H), 4.15 (d, J=5.7 Hz, 2H). MS (ESI): 314.00 [M+H+]; calcd for $[C_{16}H_{15}N_3O_4+H+]$ 314.11.

PM11

$^1$H-NMR (300 MHz, $(CD_3)_2SO$): δ 13.00 (brs, 1H), 10.31 (s, 1H), 7.89 (d, J=6.9 Hz, 1H), 7.54-7.70 (m, 6H), 7.22 (d, J=8.4 Hz, 2H), 4.16 (d, J=5.7 Hz, 2H), 3.57 (s, 3H). MS (ESI): 329.00 [M+H+]; calcd for $[C_{17}H_{16}N_2O_5+H+]$ 329.11.

PM18

$^1$H-NMR (300 MHz, $(CD_3)_2SO$): δ 12.73 (brs, 1H), 11.37 (brs, 1H), 7.97 (m, 2H), 7.38-7.87 (m, 6H), 7.05 (m, 2H). MS (ESI): 307.95 [M+H+]; calcd for $[C_{17}H_{13}N_3O_3+H+]$ 308.10.

R01

$^1$H-NMR (300 MHz, $(CD_3)_2SO$): δ 8.36 (m, 1H), 7.93 (d, J=6.0 Hz, 1H), 7.78 (m, 1H), 7.65 (d, J=5.7 Hz, 1H), 7.48 (m, 2H), 7.33 (t, J=6.0 Hz, 1H). MS (ESI): 264.00 [M+H+]; calcd for $[C_{15}H_9N_3O_2+H+]$ 264.08.

R06-1

$^1$H-NMR (300 MHz, $(CD_3)_2SO$): δ 8.64 (m, 1H), 8.14 (d, J=8.4 Hz, 1H), 7.75-7.88 (m, 2H), 7.34-7.51 (m, 3H). MS (ESI): 280.90 [M+H+]; calcd for $[C_{15}H_8N_2O_2S+H+]$ 281.04.

R07

$^1$H-NMR (300 MHz, $(CD_3)_2SO+D_2O$): δ 7.79-7.89 (m, 5H), 7.33 (m, 2H), 7.00 (m, 1H). MS (ESI): 300.95 [M−1]; calcd for $[C_{14}H_{10}N_2O_4S-1]$ 301.04.

R10

$^1$H-NMR (300 MHz, $(CD_3)_2SO$): δ 11.50 (brs, 1H), 7.87-7.99 (m, 4H), 7.64 (m, 1H), 7.36 (m, 3H), 7.16 (m, 2H). MS (ESI): 281.90 [M+H+]; calcd for $[C_{15}H_{11}N_3O_3+H+]$ 282.09.

Example 2. High Throughput Screen for Inducers of Chondrogenesis

This example describes the assay used to identify compounds that induce chondrogenesis. The assay system targeted the resident mesenchymal stem cells (MSCs) in cartilage and identified mediators that stimulated the natural repair potential and enhance integrated cartilage regeneration. This unbiased cell-based screening approach with chemical or genomic libraries has proven a powerful approach for identifying molecules that control stem cell self-renewal and fate.

The primary screening assay was based upon the development of chondrogenic nodules. Chondrocytes can grow in monolayer in vitro, but to more closely mimic their native environment in the joint, the cells are routinely cultured in non-adherent conditions such as in pellet cultures or alginate bead suspensions.

During the design of a high throughput screen of hMSCs in 384 well plates we discovered that cells, even when plated under monolayer conditions initially, if exposed to the proper stimulation and environment, develop a nodule containing the characteristics of chondrocytes grown in pellet cultures. In direct comparison with the pellet cultures of MSCs or chondrocytes, all populations of the chondrogenic nodules had high levels of cartilage specific matrix production (both proteoglycans and type II collagen expression) suggesting that chondrogenic differentiation has occurred. To initially image nodules, the wells were fixed and stained with 1 μg/ml Rhodamine B (FIG. 1) where the nodules were easily detected by eye and images captured by light microscopy. In the actual screen of a library of 22,000 structurally diverse heterocycles, $10^4$ primary hMSCs were plated in 384 well plates in serum free DMEM. The cells were treated with 5 μM of each compound and incubated for 4 days. During this period the chondrogenic nodule formed in wells that were considered a positive hit. To facilitate high throughput imaged-based detection, the chondrogenic nodules were stained with Nile red which binds non-specifically to collagens. The Nile Red stained nodules were quantified on an Acumen eX3 (high content imaging device) by excitation with a 488 laser for rapid detection of the nodules. PRO1 was thus identified as having $EC_{50}$=100 nM (see Table 1).

Figure 2A:
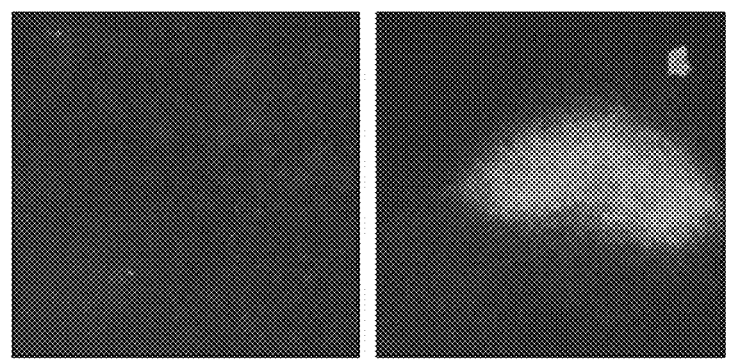
FIG. 2A shows chondrocyte differentiation as indicated by immunocytochemical staining of type II collagen in a PRO1-treated hMSC culture.

Following the initial screen, the hits were subsequently characterized in multiple secondary assays. No toxicity was found after treatment with 100 μM PRO1 in hMSCs, synovial fibroblasts, chondrocytes or HEK 293 cells (data not shown). Furthermore, a small proliferative advantage was demonstrated in human chondrocytes (<1.5 fold), but was not significant when re-evaluated in cartilage organ cultures (data not shown). The specificity of chondrocyte differentiation was confirmed by immunocytochemical staining for type II collagen (FIG. 2A), Sox9 and aggrecan in cultures of hMSCs after 18 days. In addition mRNA from pellet cultures after 7 and 21 days demonstrated expression of lubricin, aggrecan and type II collagen, but not osteocalcin or type X collagen. Similar data was generated using a mouse mesenchymal cell line, ATCD5, suggesting that PRO1 has mouse and human cross-reactivity. These data prompted an initial structure-activity relationship (SAR) be completed on the core scaffold of PRO1.

Figure 2B:
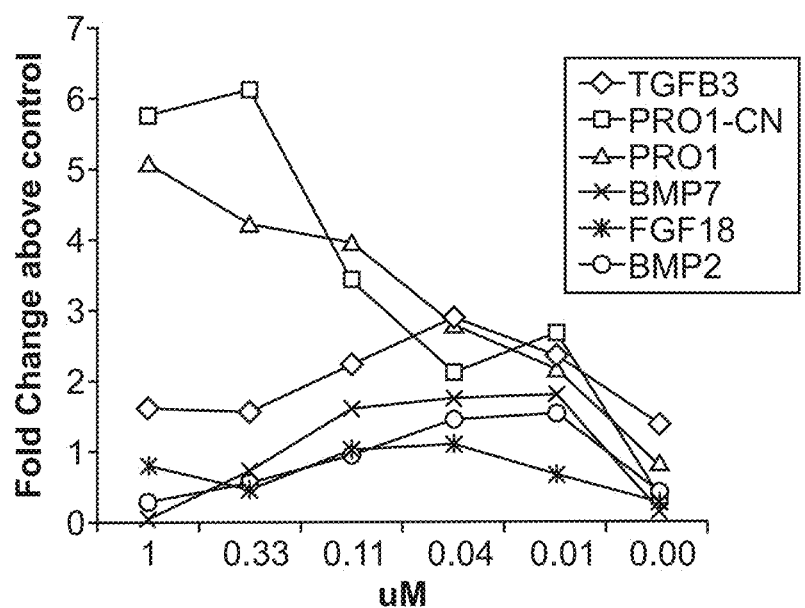
FIG. 2B shows the chondrogenic differentiation of hMSCs, as assessed by quantitation of type II collagen expression, in cell cultures treated with PRO1 (AKT), PRO1-CN (AKT-CN), and known inducers of chondrogenic differentiation.

The chondrogenic differentiation event was initiated quickly even though a fully differentiated chondrocyte phenotype cannot be assessed prior to 14 days in culture. In an 18 day assay, compound treatment was only required for the first 48 hrs and followed by removal and replacement of the media (in the absence of stimuli, FIG. 2B). The promotion of chondrogenic differentiation was not altered or enhanced upon longer treatment with the stimuli (data not shown). In addition, treatment of hMSCs with PRO1 or an analogue, PRO1-CN (Table 1), was more potent and efficient than treatment with known inducers of chondrogenic differentiation (TGFβ3, BMP7 or BMP2). The chondrocyte proliferative biologic in Phase II clinical trials, FGF18, did not effectively induce hMSC differentiation (FIG. 2B).

Figure 2C:
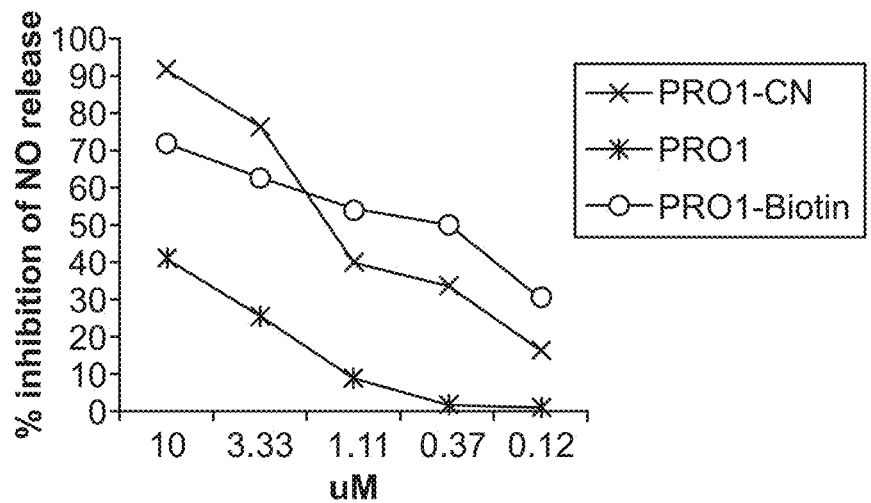
FIG. 2C shows the inhibition of cytokine-induced nitric oxide release in primary bovine chondrocyte cultures after treatment with PRO1 (AKT) and related analogues.
Figure 2D:
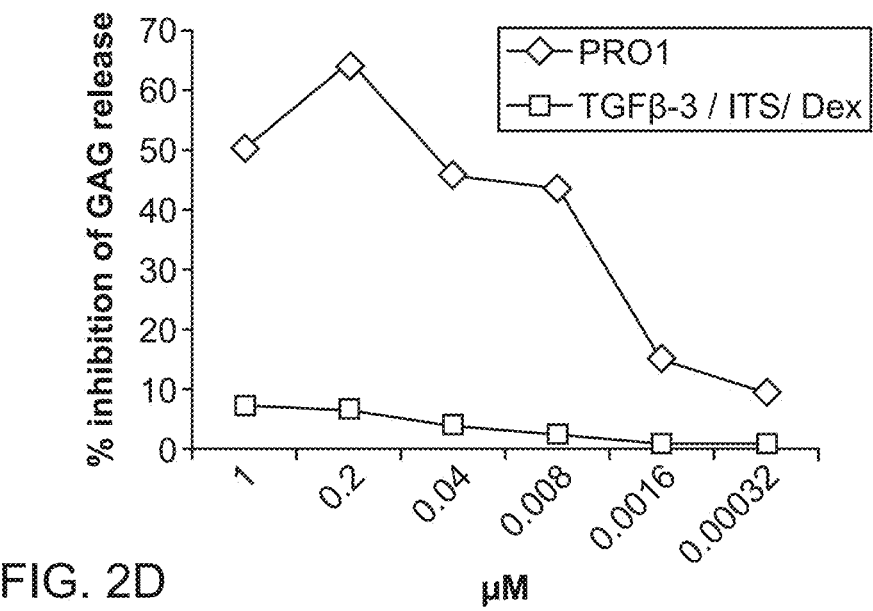
FIG. 2D shows the inhibition of cytokine-induced glycosaminoglycan (GAG) release in cartilage explants treated with PRO1 (AKT) ex vivo.
Figure 2E:
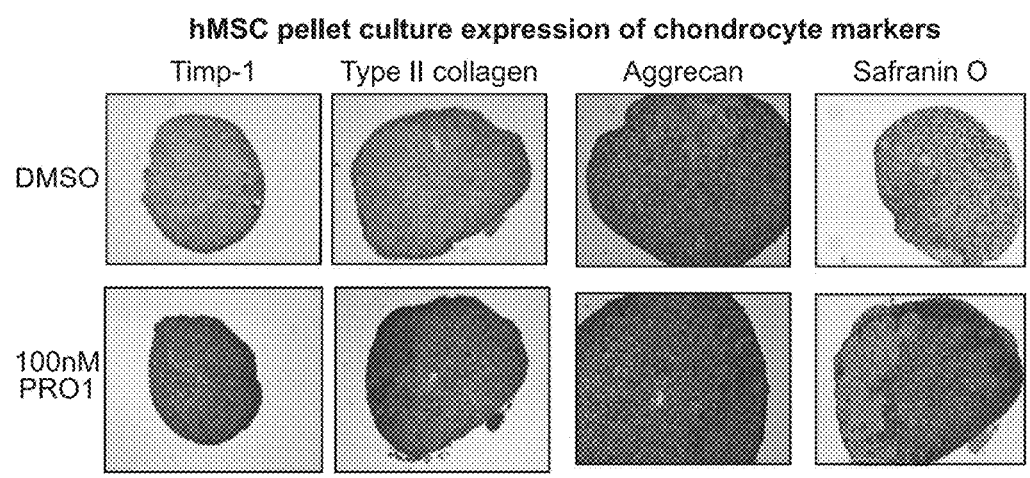
FIG. 2E shows the PRO1-induced promotion of type II collagen and aggrecan expression in a three-dimensional culture environment, as assessed by immunohistochemical staining of treated pellet cultures.

In the screen, hMSCs were used as a surrogate to future targeting of the resident MSCs with the cartilage joint. It was in that setting upon which we identified PRO1. In a joint injury, the primary cell type a therapeutic would have contact with is the chondrocyte. Although cartilage or chondrocyte-targeted screening has not lead to the development of a successful drug modifying osteoarthritis drug (DMOAD) to date, it is believed that a stem cell-based therapeutic would protect and even repair the existing chondrocytes. Therefore, protection of the articular chondrocytes and cartilage from a mature bovine knee was assessed. PRO1 and its analogues were incubated with primary bovine chondrocytes or cartilage explants cultures grown in the presence of TNFα and oncostatin M to mimic the cytokine-induced damage that can occur during OA. In the presence of the cytokine cocktail, in vitro cultured primary chondrocytes released 4-5 fold more nitric oxide (NO) than the untreated chondrocytes (50 µM vs 10 µM) as measured by the Greiss reaction. In cells treated with the cytokine cocktail and PRO1, the small molecule could effectively block the release of NO by up to 70% FIG. 2C). Similarly, in ex vivo treated cartilage explants, cytokine-induced release of glycosaminoglycans (GAG) was reduced by up to 60% by PRO1 (FIG. 2D). Finally, hMSC were grown in pellet culture for 21 days. Upon immunohistochemical staining of the pellets, it was demonstrated that PRO1 could increase type II collagen and aggrecan expression in a three dimensional culture environment (FIG. 2E).

TABLE 1

Table of compounds synthesized and selected by SAR

| PRODUCT | STRUCTURE | CHONDROGENIC µM $EC_{50}$/ NO INHIBTION µM $IC_{50}$ | COLLAGEN TYPE II µM $EC_{50}$ |
|---|---|---|---|
| AKT, AKT093, PRO1 | 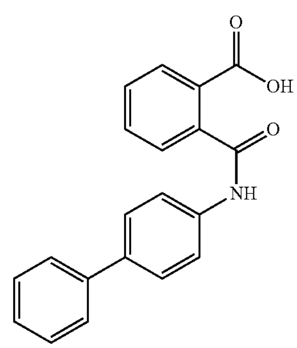 [SMILES: O=C(O)c1ccccc1C(=O)Nc1ccc(-c2ccccc2)cc1] | 0.225/0.45 | 0.08 |
| AKT-CN, LK3, LK81, PRO1-CN | 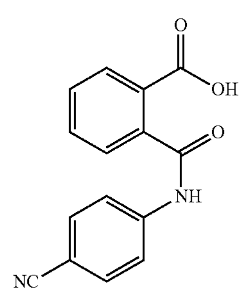 [SMILES: N#Cc1ccc(NC(=O)c2ccccc2C(=O)O)cc1] | 0.137/0.03 | 0.108 |

TABLE 1-continued

Table of compounds synthesized and selected by SAR

| PRODUCT | STRUCTURE | CHONDROGENIC µM EC$_{50}$/ NO INHIBTION µM IC$_{50}$ | COLLAGEN TYPE II µM EC$_{50}$ |
|---|---|---|---|
| AKT-Me L3 | 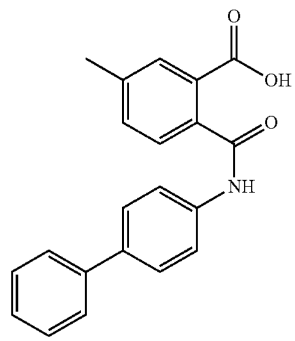 [SMILES: Cc1ccc(C(=O)Nc2ccc(-c3ccccc3)cc2)c(C(=O)O)c1] | >10/>10 | >10 |
| AKT-biotine LK14 | PRO-1-Linker-biotin | 0.04/0.001 | >10 |
| AKT-NHEt LK19b | 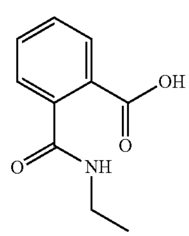 | 2.01\>10 | >10 |
| LK6 | 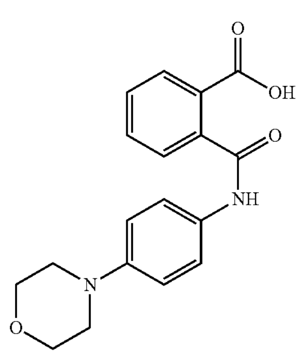 [SMILES: O=C(O)c1ccccc1C(=O)Nc1ccc(N2CCOCC2)cc1] | 9.1/>10 | >10 |

TABLE 1-continued

Table of compounds synthesized and selected by SAR

| PRODUCT | STRUCTURE | CHONDROGENIC µM EC$_{50}$/ NO INHIBTION µM IC$_{50}$ | COLLAGEN TYPE II µM EC$_{50}$ |
|---|---|---|---|
| LK20b | 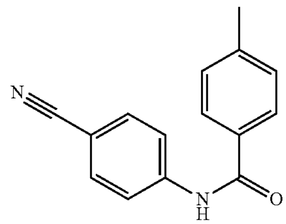 [SMILES: Cc1ccc(C(=O)Nc2ccc(C#N)cc2)cc1] | 0.014>10 | >10 |
| Resynthesized LK8 | HRMS (ESI): 320.0425 [M + H+]; calcd for [C$_{14}$H$_{12}$N$_2$O$_5$S + H+] 320.0427. | 9.1/>10 | >10 |
| SMA-1* LK17b | 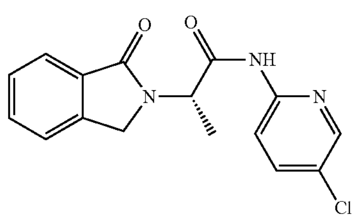 [SMILES: C[C@@H](C(=O)Nc1ccc(Cl)cn1)N1Cc2ccccc2C1=O] | >10/0.04 | 0.37 |
| L11c | 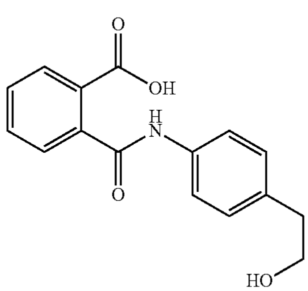 [SMILES: O=C(O)c1ccccc1C(=O)Nc1ccc(CCO)cc1] | 0.125/>10 | >10 |
| Resynthesized L2 | 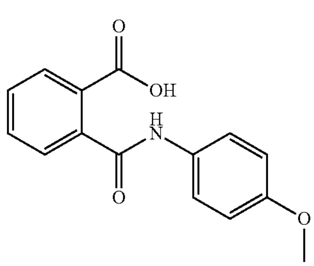 [SMILES: COc1ccc(NC(=O)c2ccccc2C(=O)O)cc1] | >10/ND | >10 |

TABLE 1-continued

Table of compounds synthesized and selected by SAR

| PRODUCT | STRUCTURE | CHONDROGENIC µM EC$_{50}$/ NO INHIBTION µM IC$_{50}$ | COLLAGEN TYPE II µM EC$_{50}$ |
|---|---|---|---|
| Resynthesized L11a | *structure: 2-carboxy-N-(4-iodophenyl)benzamide* | >10/>10 | >10 |
| L9 | *structure: 2-carboxy-N-(quinolin-7-yl)benzamide* | >10/>10 | >10 |
| L5 | *structure: 2-carboxy-N-(5-methylpyridin-3-yl)benzamide*<br><br>HRMS (ESI): 256.0852 [M + H+]; calcd for [C$_{14}$H$_{12}$N$_2$O$_3$ + H+] 256.0848. | 0.6/2.4 | >10 |
| LK18b | *structure: sodium 2-(([1,1'-biphenyl]-4-ylcarbamoyl)benzoate*<br><br>HRMS (ESI): 339.0866 [M + H+]; calcd for [C$_{20}$H$_{14}$N$_2$NaO$_3$ + H+] 339.0871. | 0.0015/2.7 | 0.05 |

TABLE 1-continued

Table of compounds synthesized and selected by SAR

| PRODUCT | STRUCTURE | CHONDROGENIC µM EC$_{50}$/ NO INHIBTION µM IC$_{50}$ | COLLAGEN TYPE II µM EC$_{50}$ |
|---|---|---|---|
| LK22b | [structure of 5-hydroxy-2-(biphenyl-4-ylcarbamoyl)benzoic acid] | 0.0046/>10 | >10 |
| LK4 | [bis-amide sulfone structure]<br><br>HRMS (ESI): 697.1634 [M + H+]; calcd for [C$_{40}$H$_{28}$N$_2$O$_8$S + H+] 697.1645. | 3.8/>10 | 33.34 |
| LK63 | [structure with chloro and carboxylic acid substituents]<br><br>HRMS (ESI): 320.0332 [M + H+]; calcd for [C$_{15}$H$_{10}$ClNO$_5$ + H+] 320.0326 | 0.126/.0298 | ND |

TABLE 1-continued

Table of compounds synthesized and selected by SAR

| PRODUCT | STRUCTURE | CHONDROGENIC µM EC$_{50}$/ NO INHIBTION µM IC$_{50}$ | COLLAGEN TYPE II µM EC$_{50}$ |
|---|---|---|---|
| LK60 | 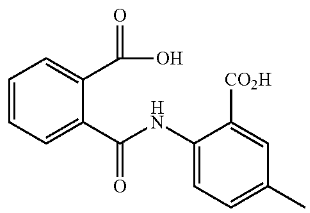 [SMILES: Cc1ccc(NC(=O)c2ccccc2C(=O)O)c(C(=O)O)c1] | 0.014/1.245 | ND |
| LK35 | HRMS (ESI): 361.0452 [M + H+]; calcd for [C$_{17}$H$_{10}$F$_2$N$_2$O$_3$S + H+] 361.0458. | >10/0.03 | >10 |
| LK62 | 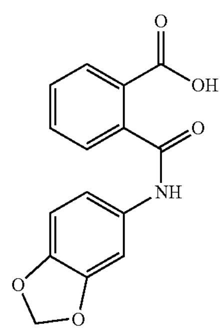 [SMILES: O=C(O)c1ccccc1C(=O)Nc1ccc2c(c1)OCO2] | 3.36/0.145 | ND |
| Resynthesized LK57 | 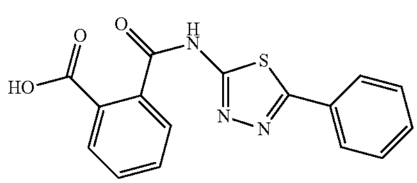 [SMILES: O=C(O)c1ccccc1C(=O)Nc1nnc(-c2ccccc2)s1] | >10/ND | ND |
| LK61 | HRMS (ESI): 324.0741 [M + H+]; calcd for [C$_{17}$H$_{10}$N$_2$O$_3$S + H+] 324.0746. | 0.052/1.69 | ND |

TABLE 1-continued

Table of compounds synthesized and selected by SAR

| PRODUCT | STRUCTURE | CHONDROGENIC µM EC$_{50}$/ NO INHIBTION µM IC$_{50}$ | COLLAGEN TYPE II µM EC$_{50}$ |
|---|---|---|---|
| Resynthesized LK49 | 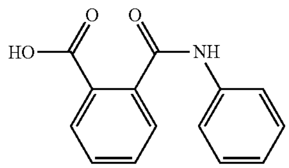 [SMILES: O=C(O)c1ccccc1C(=O)Nc1ccccc1] | 5/>10 | ND |
| | | >10/2.5 | ND |
| LK53 | 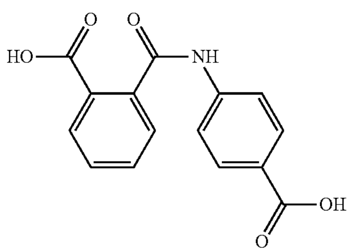 [SMILES: O=C(O)c1ccc(NC(=O)c2ccccc2C(=O)O)cc1] | 0.005/0.146 | ND |
| | | >10/0.624 | ND |
| | | ND/>10 | ND |
| | | ND/2.7 | ND |

TABLE 1-continued

Table of compounds synthesized and selected by SAR

| PRODUCT | STRUCTURE | CHONDROGENIC µM EC$_{50}$/ NO INHIBTION µM IC$_{50}$ | COLLAGEN TYPE II µM EC$_{50}$ |
|---|---|---|---|
| | [structure: 2-carboxy-4,5-dichloro-N-(4-benzylphenyl)benzamide] | ND/>10 | ND |
| | [structure: 2-carboxy-N-(4-vinyloxyphenyl)benzamide] | ND/>10 | ND |
| | [structure: prop-2-ynyl 2-((4-bromophenyl)carbamoyl)benzoate] | ND/>10 | ND |
| | [structure: methyl 2-(phenylcarbamoyl)benzoate]<br>HRMS (ESI): 255.0895 [M + H+]; calcd for [C$_{15}$H$_{13}$NO$_3$ + H+] 255.0895. | ND/>10 | ND |
| | [structure: 4-nitrobenzyl 2-(phenylcarbamoyl)benzoate] | ND/>10 | ND |

TABLE 1-continued

Table of compounds synthesized and selected by SAR

| PRODUCT | STRUCTURE | CHONDROGENIC µM $EC_{50}$/ NO INHIBTION µM $IC_{50}$ | COLLAGEN TYPE II µM $EC_{50}$ |
|---|---|---|---|
| | *[structure: 2-(allyloxycarbonyl)-N-(4-iodophenyl)benzamide]* | ND/>10 | ND |
| | *[structure: 2-((4-(3-methylmorpholine-4-carbonyl)phenyl)carbamoyl)benzoic acid]* | ND/2.64 | ND |
| | *[structure: 2-((4-(isobutenylsulfonyl)phenyl)carbamoyl)benzoic acid]* | ND/0.925 | ND |
| | *[structure: 2-((4-(pentyloxy)phenyl)carbamoyl)benzoic acid]* | ND/>10 | ND |

TABLE 1-continued

Table of compounds synthesized and selected by SAR

| PRODUCT | STRUCTURE | CHONDROGENIC µM EC$_{50}$/ NO INHIBITION µM IC$_{50}$ | COLLAGEN TYPE II µM EC$_{50}$ |
|---|---|---|---|
| | | ND/>10 | ND |
| | | ND/0.925 | ND |
| | | ND/>10 | ND |
| | | ND/>10 | ND |
| | | ND/>10 | ND |

TABLE 1-continued
Table of compounds synthesized and selected by SAR
| PRODUCT | STRUCTURE | CHONDROGENIC µM EC$_{50}$/ NO INHIBTION µM IC$_{50}$ | COLLAGEN TYPE II µM EC$_{50}$ |
|---|---|---|---|
|  | 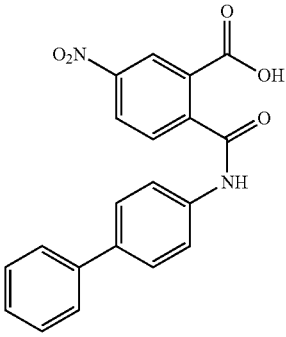 [SMILES: O=C(O)c1cc([N+](=O)[O-])ccc1C(=O)Nc1ccc(-c2ccccc2)cc1] | ND/>10 | ND |
|  | 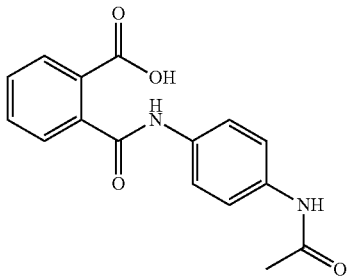 [SMILES: CC(=O)Nc1ccc(NC(=O)c2ccccc2C(=O)O)cc1] | ND/>10 | ND |
| AKT-CH2OH L1 | 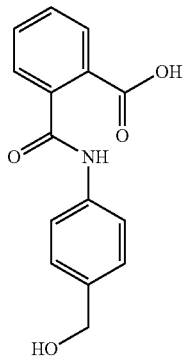 [SMILES: O=C(O)c1ccccc1C(=O)Nc1ccc(CO)cc1] | 0.04/0.27 | 8.46 |
| AKT-NHMe LK23 | 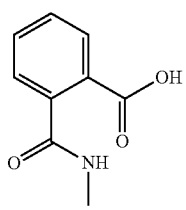 | 2.7/0.0046 | 0.24 |

TABLE 1-continued
Table of compounds synthesized and selected by SAR
| PRODUCT | STRUCTURE | CHONDROGENIC μM EC$_{50}$/ NO INHIBITION μM IC$_{50}$ | COLLAGEN TYPE II μM EC$_{50}$ |
|---|---|---|---|
| AKT-F LK5 | 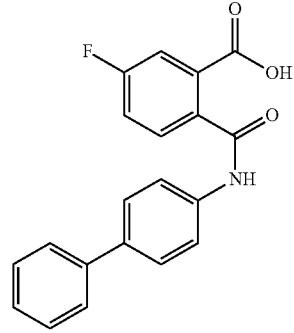 | >10/>10 | >10 |
| AKT-azide LK80 LK80b | 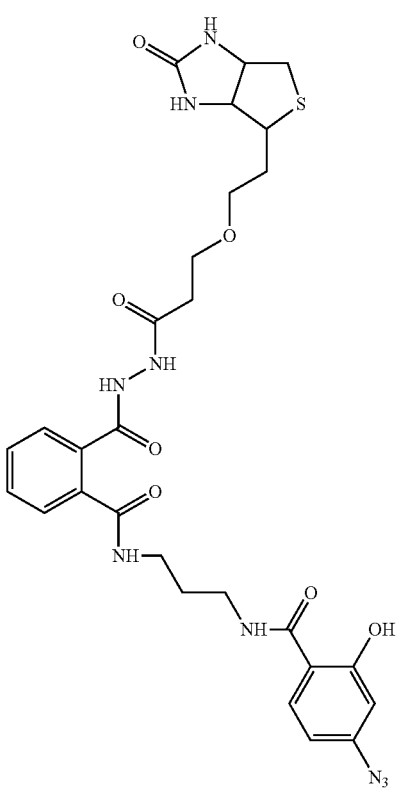 [SMILES: [N-]=[N+]=Nc1ccc(C(=O)NCCCNC(=O)c2ccccc2C(=O)NNC(=O)CCOCCC2SCC3NC(=O)NC32)c(O)c1] | ND/0.12 | 0.654 |

TABLE 1-continued
Table of compounds synthesized and selected by SAR
| PRODUCT | STRUCTURE | CHONDROGENIC µM EC$_{50}$/ NO INHIBTION µM IC$_{50}$ | COLLAGEN TYPE II µM EC$_{50}$ |
|---|---|---|---|
| AKT-iPr LK14b | 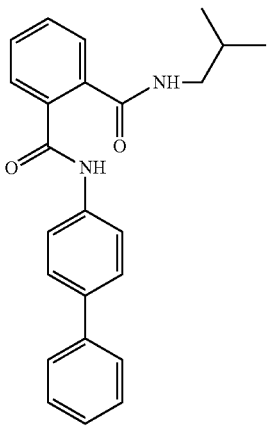 [SMILES: CC(C)CNC(=O)c1ccccc1C(=O)Nc1ccc(-c2ccccc2)cc1] | 0.0015/>10 | 6.978 |
| Resynthesized LK7 | 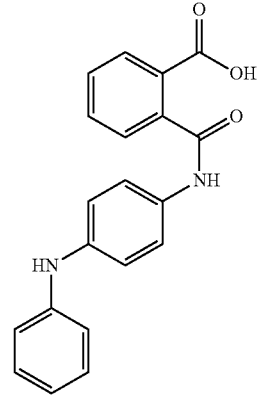 [SMILES: O=C(O)c1ccccc1C(=O)Nc1ccc(Nc2ccccc2)cc1] | >10/>10 | >10 |
| LK15 | 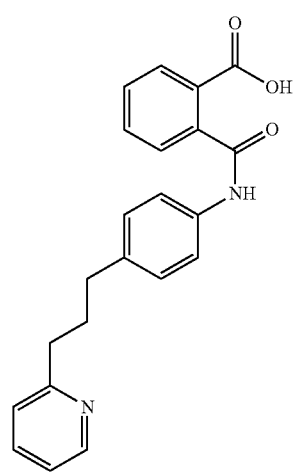 [SMILES: O=C(O)c1ccccc1C(=O)Nc1ccc(CCCc2ccccn2)cc1] | 0.12/>10 | >10 |

TABLE 1-continued

Table of compounds synthesized and selected by SAR

| PRODUCT | STRUCTURE | CHONDROGENIC µM $EC_{50}$/ NO INHIBITION µM $IC_{50}$ | COLLAGEN TYPE II µM $EC_{50}$ |
|---|---|---|---|
| L12 | 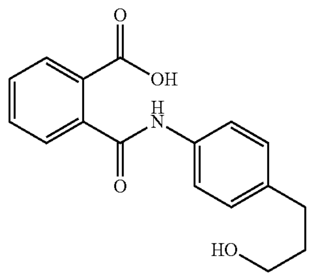 [SMILES: O=C(O)c1ccccc1C(=O)Nc1ccc(CCCO)cc1] | ND/ND | ND |
| L4 | 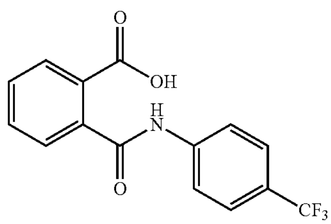 [SMILES: O=C(O)c1ccccc1C(=O)Nc1ccc(C(F)(F)F)cc1] | 9.5/22.1 | 11.1 |
| Resynthesized L7 | 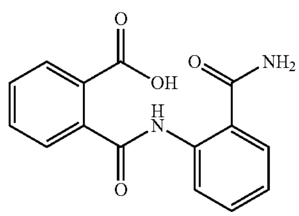 [SMILES: NC(=O)c1ccccc1NC(=O)c1ccccc1C(=O)O] | >10/>10 | >10 |
| L6 | 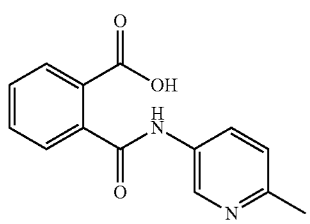 [SMILES: Cc1ccc(NC(=O)c2ccccc2C(=O)O)cn1] | >10/>10 | >10 |
| LK55b | 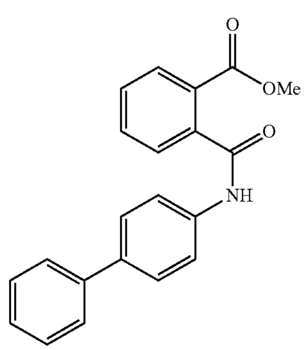 [SMILES: COC(=O)c1ccccc1C(=O)Nc1ccc(-c2ccccc2)cc1] | 0.124/.234 | ND |
| LK13b | 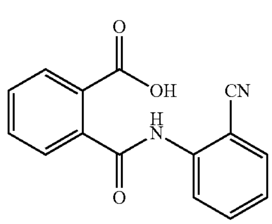 [SMILES: N#Cc1ccccc1NC(=O)c1ccccc1C(=O)O] | >10/ND | ND |

TABLE 1-continued
Table of compounds synthesized and selected by SAR
| PRODUCT | STRUCTURE | CHONDROGENIC µM EC$_{50}$/ NO INHIBTION µM IC$_{50}$ | COLLAGEN TYPE II µM EC$_{50}$ |
|---|---|---|---|
| | HRMS (ESI): 266.2519 [M + H+]; calcd for [C15H10N2O3 + H+] 266.2515. | | |
| L13 | 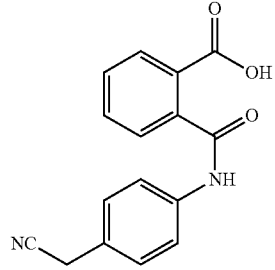 [SMILES: N#CCc1ccc(NC(=O)c2ccccc2C(=O)O)cc1] | >10/>10 | >10 |
| | HRMS (ESI): 280.0853 [M + H+]; calcd for [C16H12N2O3 + H+] 280.0848. | | |
| LK51 | 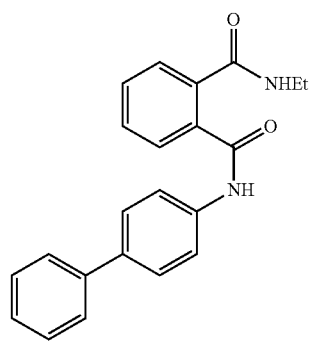 | ND/ND | ND |
| LK52 | 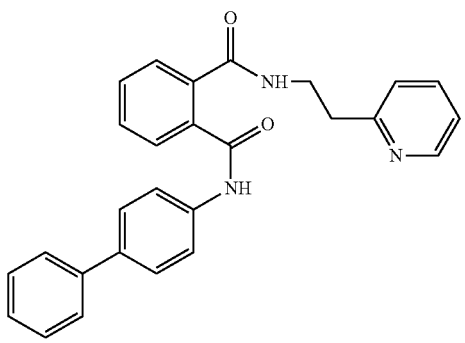 [SMILES: O=C(NCCc1ccccn1)c1ccccc1C(=O)Nc1ccc(-c2ccccc2)cc1] | ND/ND | ND |
| | HRMS (ESI): 421.1796 [M + H+]; calcd for [C27H23N3O2 + H+] 421.1790. | | |

TABLE 1-continued

Table of compounds synthesized and selected by SAR

| PRODUCT | STRUCTURE | CHONDROGENIC µM $EC_{50}$/ NO INHIBTION µM $IC_{50}$ | COLLAGEN TYPE II µM $EC_{50}$ |
|---|---|---|---|
| LK55 | [structure: 2-({[4-(aminomethyl)phenyl]carbamoyl})benzoic acid] | 0.126/0.216 | ND |
| LK58 | [structure: N-benzoyl phthalamic acid derivative] HRMS (ESI): 269.0692 [M + H+]; calcd for [C15H11NO4 + H+] 269.0688. | ND/ND | ND |
|  | [structure: 2-({[4-(3-hydroxypropyl)phenyl]carbamoyl})benzoic acid] |  |  |
| Resynthesized LK64 | [structure: 2-({[(4-carboxyphenyl)methyl]carbamoyl})benzoic acid] | 0.398/0.981 | ND |
| LK59 | [structure: 2-{[(5-nitropyridin-2-yl)carbamoyl]}benzoic acid] HRMS (ESI): 287.2277 [M + H+]; calcd for [C13H9NO5 + H+] 287.2277. | 0.371/0.491 | ND |

TABLE 1-continued

Table of compounds synthesized and selected by SAR

| PRODUCT | STRUCTURE | CHONDROGENIC µM EC$_{50}$/ NO INHIBTION µM IC$_{50}$ | COLLAGEN TYPE II µM EC$_{50}$ |
|---|---|---|---|
| Resynthesized | 2-carboxy-N-(4-fluorophenyl)benzamide structure<br><br>HRMS (ESI): 259.0639 [M + H+]; calcd for [C14H10FNO3 + H+] 259.0645. | >10 uM/0.0125 | ND |
| | 2-carboxy-N-(4-(6-methylbenzo[d]thiazol-2-yl)phenyl)benzamide structure | ND/0.987 | ND |
| | 2-carboxy-N-(4-(2-phenylthiazol-4-yl)phenyl)benzamide structure | ND/>10 | ND |
| | N-(2,4-dicarboxyphenyl)-2-carboxybenzamide structure | ND/>10 | ND |

TABLE 1-continued

Table of compounds synthesized and selected by SAR

| PRODUCT | STRUCTURE | CHONDROGENIC µM EC$_{50}$/ NO INHIBTION µM IC$_{50}$ | COLLAGEN TYPE II µM EC$_{50}$ |
|---|---|---|---|
| | (4-bromophenyl carbamoyl benzene-1,3-dicarboxylic acid) | ND/>10 | ND |
| | (4-hydroxyphenyl carbamoyl benzene-1,3-dicarboxylic acid) | ND/>10 | ND |
| | 2-((4-(p-tolyloxy)phenyl)carbamoyl)benzoic acid | ND/>10 | ND |
| | 2-((4-(naphthalen-2-yloxy)phenyl)carbamoyl)benzoic acid | ND/>10 | ND |
| | 4,5-dichloro-2-((4-methoxyphenyl)carbamoyl)benzoic acid | ND/>10 | ND |

TABLE 1-continued
Table of compounds synthesized and selected by SAR
| PRODUCT | STRUCTURE | CHONDROGENIC µM EC$_{50}$/ NO INHIBTION µM IC$_{50}$ | COLLAGEN TYPE II µM EC$_{50}$ |
|---|---|---|---|
| | 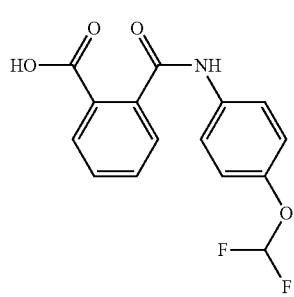 [SMILES: O=C(O)c1ccccc1C(=O)Nc1ccc(OC(F)F)cc1] | ND/>10 | ND |
| | 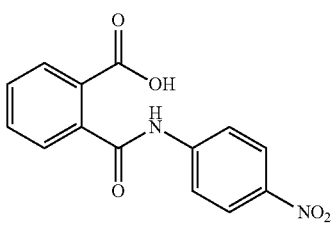 [SMILES: O=C(O)c1ccccc1C(=O)Nc1ccc([N+](=O)[O-])cc1] | ND/>10 | ND |
| | 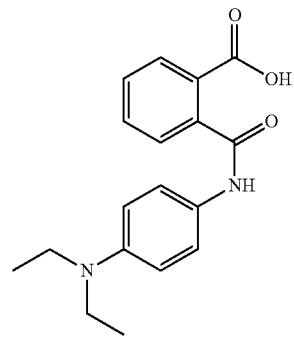 [SMILES: CCN(CC)c1ccc(NC(=O)c2ccccc2C(=O)O)cc1] | ND/2.98 | ND |
| | 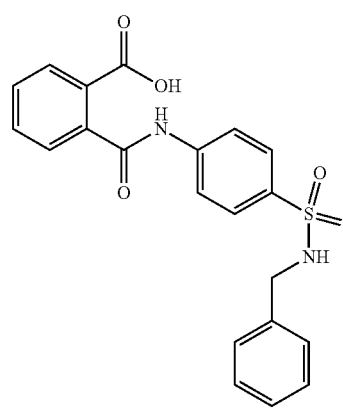 | ND/>10 | ND |

TABLE 1-continued

Table of compounds synthesized and selected by SAR

| PRODUCT | STRUCTURE | CHONDROGENIC µM $EC_{50}$/ NO INHIBTION µM $IC_{50}$ | COLLAGEN TYPE II µM $EC_{50}$ |
|---|---|---|---|
| | (structure) | ND/>10 | ND |
| | (structure) | ND/>10 | ND |
| | (structure) | ND/>10 | ND |
| | (structure) | ND/>10 | ND |
| | (structure) | ND/>10 | ND |

TABLE 1-continued

Table of compounds synthesized and selected by SAR

| PRODUCT | STRUCTURE | CHONDROGENIC µM $EC_{50}$/ NO INHIBTION µM $IC_{50}$ | COLLAGEN TYPE II µM $EC_{50}$ |
|---|---|---|---|
| | 4,5-dichloro-2-[(4-methoxyphenyl)carbamoyl]benzoic acid | ND/>10 | ND |
| | 3-hydroxy-2-[(4-ethoxyphenyl)carbamoyl]benzoic acid | ND/>10 | ND |
| | 4-[(4-iodophenyl)carbamoyl]benzene-1,3-dicarboxylic acid | ND/>10 | ND |
| | 2-[(4-acetylphenyl)carbamoyl]benzoic acid | ND/>10 | ND |

TABLE 2

Additional Compounds

| Compound | Structure | Activity[1] |
|---|---|---|
| A01 | 2-CN-C6H4-C(O)NH-C6H4-4-CN | ** |
| A02 | 2-NHMe-C6H4-C(O)NH-C6H4-4-CN | |
| A04 | 2-OH-C6H4-C(O)NH-C6H4-4-CN | |
| A05 | 2-OMe-C6H4-C(O)NH-C6H4-4-CN | |
| A06 | 2-(CO2H-CH2)-C6H4-C(O)NH-C6H4-4-CN | *** |
| A08 | 2-(HOCH2)-C6H4-C(O)NH-C6H4-4-CN | |
| A09 | 2-(MeC(O))-C6H4-C(O)NH-C6H4-4-CN | ** |
| A10 | 2-(AcNH)-C6H4-C(O)NH-C6H4-4-CN | |
| A11 | 2-(MeOC(O)NH)-C6H4-C(O)NH-C6H4-4-CN | ** |
| A12 | 2-(H2NC(O)NH)-C6H4-C(O)NH-C6H4-4-CN | ** |
| A13 | 2-(MeSO2NH)-C6H4-C(O)NH-C6H4-4-CN | ** |
| A14 | 2-(tetrazol-5-yl)-C6H4-C(O)NH-C6H4-4-CN | |

TABLE 2-continued

Additional Compounds

| Compound | Structure | Activity[1] |
|---|---|---|
| A17 | 3-(CO2H)-C6H4-C(=O)-NH-C6H4-4-CN | |
| A18 | 3-(HO2C-CH2)-C6H4-C(=O)-NH-C6H4-4-CN | |
| A22 | 2-(SO3H)-C6H4-C(=O)-NH-C6H4-4-CN | ** |
| A23 | 2-(SO2NH2)-C6H4-C(=O)-NH-C6H4-4-CN | ** |
| A24 | 2-(SO2NHMe)-C6H4-C(=O)-NH-C6H4-4-CN | ** |
| A25 | 2-(P(=O)(OH)2)-C6H4-C(=O)-NH-C6H4-4-CN | |
| B02 | 5-CN-2-(CO2H)-C6H3-C(=O)-NH-C6H4-4-CN | ** |
| B03 | 4-CN-2-(CO2H)-C6H3-C(=O)-NH-C6H4-4-CN | *** |
| B05 | 3-Cl-2-(CO2H)-C6H3-C(=O)-NH-C6H4-4-CN | |
| B06 | 4-Cl-2-(CO2H)-C6H3-C(=O)-NH-C6H4-4-CN | |
| B07 | 5-Cl-2-(CO2H)-C6H3-C(=O)-NH-C6H4-4-CN | |
| B08 | 6-Cl-2-(CO2H)-C6H3-C(=O)-NH-C6H4-4-CN | |
| B10 | 4-(CO2H)-2-(CO2H)-C6H3-C(=O)-NH-C6H4-4-CN | ** |

TABLE 2-continued

Additional Compounds

| Compound | Structure | Activity[1] |
|---|---|---|
| B11 | 4-cyanoanilide of 2,5-dicarboxybenzamide | |
| B12 | 4-cyanoanilide of 2,6-dicarboxybenzamide | ** |
| B13 | 4-cyanoanilide of 2-carboxy-3-methoxybenzamide | |
| B14 | 4-cyanoanilide of 2-carboxy-4-methoxybenzamide | |
| B15 | 4-cyanoanilide of 2-carboxy-5-methoxybenzamide | |
| B16 | 4-cyanoanilide of 2-carboxy-6-methoxybenzamide | |
| B17 | 4-cyanoanilide of 3-carboxypicolinamide | |
| B18 | 4-cyanoanilide of 4-carboxynicotinamide | |
| B19 | 4-cyanoanilide of 5-carboxyisonicotinamide | *** |
| B20 | 4-cyanoanilide of 2-carboxynicotinamide | ** |
| B21 | 4-cyanoanilide of 3-carboxypyrazine-2-carboxamide | |
| B27 | 4-cyanoanilide of benzo[d][1,3]dioxole-5,6-dicarboxamide | |
| B28 | 4-cyanoanilide of 1H-benzimidazole-5,6-dicarboxamide | |
| B29 | 4-cyanoanilide of cyclohex-1-ene-1,2-dicarboxamide | |
| B30 | 4-cyanoanilide of norbornene dicarboxamide | |

TABLE 2-continued

Additional Compounds

| Compound | Structure | Activity[1] |
|---|---|---|
| B31 | 4-cyanophenyl 8-carboxy-naphthalene-1-carboxamide | |
| B32 | 2'-(4-cyanophenylcarbamoyl)-biphenyl-2-carboxylic acid | ** |
| MS01 | 2-((2-carboxybenzyl)carbamoyl)benzoic acid | *** |
| MS02 | 2-((3-carboxybenzyl)carbamoyl)benzoic acid | ** |
| MS03 | 2-((4-carboxybenzyl)carbamoyl)benzoic acid | |
| MS04 | 2-((2-cyanobenzyl)carbamoyl)benzoic acid | ** |
| MS05 | 2-((3-cyanobenzyl)carbamoyl)benzoic acid | |
| MS06 | 2-((4-cyanobenzyl)carbamoyl)benzoic acid | ** |
| MS07 | 2-((4-methoxybenzyl)carbamoyl)benzoic acid | |
| MS08 | 2-((benzo[d][1,3]dioxol-5-ylmethyl)carbamoyl)benzoic acid | |
| MS09 | 2-(2-((4-cyanophenyl)amino)-2-oxoethyl)benzoic acid | |
| MS10 | 2-(2-((4-carboxyphenyl)amino)-2-oxoethyl)benzoic acid | |
| MS11 | 2-(((4-cyanobenzamido)methyl)benzoic acid | ** |
| MS13 | 2-(2-(4-cyanophenyl)acetamido)benzoic acid | |
| MS14 | 2-(2-(4-carboxyphenyl)acetamido)benzoic acid | ** |
| MS15 | 2-(3-(4-cyanophenyl)acryloyl)benzoic acid | *** |
| MS16 | 2-(3-(4-carboxyphenyl)acryloyl)benzoic acid | ** |

TABLE 2-continued
Additional Compounds
| Compound | Structure | Activity[1] |
|---|---|---|
| MS17-1 | 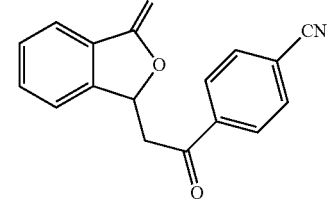 | *** |
| MS18-1 | | ** |
| MS19 | | |
| MS21 | | *** |
| MS26 | | ** |
| MS27 | | |
| MS28 | | ** |
| MS29 | 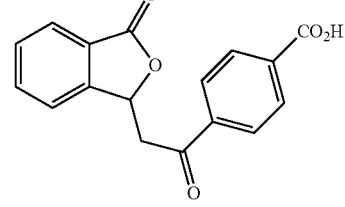 | *** |
| MS30 | 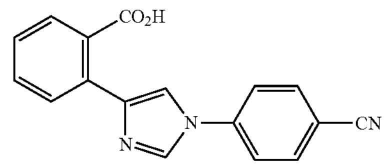 [SMILES: N#Cc1ccc(-n2cnc(-c3ccccc3C(=O)O)c2)cc1] | |
| MS31 | 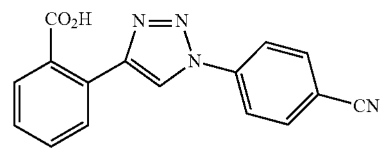 [SMILES: N#Cc1ccc(-n2cc(-c3ccccc3C(=O)O)nn2)cc1] | |
| MS32 | 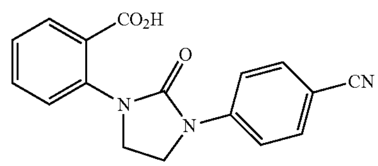 [SMILES: N#Cc1ccc(N2CCN(c3ccccc3C(=O)O)C2=O)cc1] | |
| MS35 | 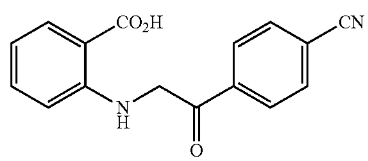 [SMILES: N#Cc1ccc(C(=O)CNc2ccccc2C(=O)O)cc1] | |
| MS36 | 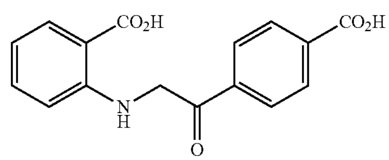 [SMILES: O=C(O)c1ccc(C(=O)CNc2ccccc2C(=O)O)cc1] | |
| MS38 | 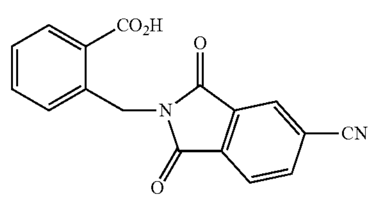 [SMILES: N#Cc1ccc2c(c1)C(=O)N(Cc1ccccc1C(=O)O)C2=O] | |
| MS39 | 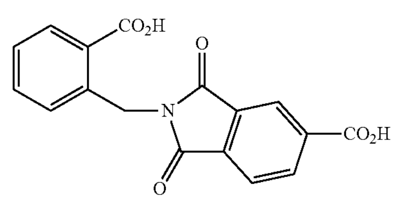 [SMILES: O=C(O)c1ccc2c(c1)C(=O)N(Cc1ccccc1C(=O)O)C2=O] | *** |
| N01 | 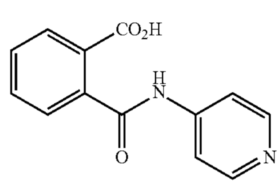 [SMILES: O=C(O)c1ccccc1C(=O)Nc1ccncc1] | *** |

TABLE 2-continued

Additional Compounds

| Compound | Structure | Activity[1] |
|---|---|---|
| N02 | 2-CO$_2$H-C$_6$H$_4$-C(O)NH-(quinolin-2-yl) | |
| N04 | 2-CO$_2$H-C$_6$H$_4$-C(O)NH-C$_6$H$_4$-2-OCF$_2$H | *** |
| N05 | 2-CO$_2$H-C$_6$H$_4$-C(O)NH-C$_6$H$_4$-3-OCF$_2$H | ** |
| N06 | 2-CO$_2$H-C$_6$H$_4$-C(O)NH-C$_6$H$_4$-4-OCF$_2$H | |
| N07 | 2-CO$_2$H-C$_6$H$_4$-C(O)NH-C$_6$H$_4$-2-COMe | |
| N08 | 2-CO$_2$H-C$_6$H$_4$-C(O)NH-C$_6$H$_4$-3-COMe | **** |
| N09 | 2-CO$_2$H-C$_6$H$_4$-C(O)NH-C$_6$H$_4$-4-COMe | ** |
| N10 | 2-CO$_2$H-C$_6$H$_4$-C(O)NH-C$_6$H$_4$-2-CONH$_2$ | ** |
| N11 | 2-CO$_2$H-C$_6$H$_4$-C(O)NH-C$_6$H$_4$-3-CONH$_2$ | ** |
| N12 | 2-CO$_2$H-C$_6$H$_4$-C(O)NH-C$_6$H$_4$-4-CONH$_2$ | |
| N13 | 2-CO$_2$H-C$_6$H$_4$-C(O)NH-C$_6$H$_4$-2-CO$_2$H | ** |
| N14 | 2-CO$_2$H-C$_6$H$_4$-C(O)NH-C$_6$H$_4$-3-CO$_2$H | ** |
| N15 | 2-CO$_2$H-C$_6$H$_4$-C(O)NH-C$_6$H$_4$-4-CO$_2$H | |
| N16 | 2-CO$_2$H-C$_6$H$_4$-C(O)NH-C$_6$H$_4$-2-SO$_2$NH$_2$ | |
| N17 | 2-CO$_2$H-C$_6$H$_4$-C(O)NH-C$_6$H$_4$-3-SO$_2$NH$_2$ | ** |
| N18 | 2-CO$_2$H-C$_6$H$_4$-C(O)NH-C$_6$H$_4$-4-SO$_2$NH$_2$ | |

TABLE 2-continued

Additional Compounds

| Compound | Structure | Activity[1] |
|---|---|---|
| N19 | 2-HO₂C-C₆H₄-C(O)NH-(3-CN-C₆H₄) | *** |
| N20 | 2-HO₂C-C₆H₄-C(O)NH-(2-CH₂OH-C₆H₄) | ** |
| N21 | 2-HO₂C-C₆H₄-C(O)NH-(3-CH₂OH-C₆H₄) | |
| N22 | 2-HO₂C-C₆H₄-C(O)NH-(4-CH₂OH-C₆H₄) | |
| N23 | 2-HO₂C-C₆H₄-C(O)NH-(2-CH₂NHMe-C₆H₄) | |
| N24 | 2-HO₂C-C₆H₄-C(O)NH-(3-CH₂NHMe-C₆H₄) | *** |
| N25 | 2-HO₂C-C₆H₄-C(O)NH-(4-CH₂NHMe-C₆H₄) | |
| N26 | 2-HO₂C-C₆H₄-C(O)NH-(4-CH₂CH₂OH-C₆H₄) | *** |
| N27 | 2-HO₂C-C₆H₄-C(O)NH-(3-morpholino-C₆H₄) | |
| N28 | 2-HO₂C-C₆H₄-C(O)NH-(4-morpholino-C₆H₄) | ** |
| N29 | 2-HO₂C-C₆H₄-C(O)NH-cyclopropyl | |
| N30 | 2-HO₂C-C₆H₄-C(O)NH-(4-CN-cyclohexyl) | ** |
| N31 | 2-HO₂C-C₆H₄-C(O)NH-(4-CO₂H-cyclohexyl) | ** |
| N32 | 2-HO₂C-C₆H₄-C(O)NH-CH₂-(4-CN-cyclohexyl) | |
| N33 | 2-HO₂C-C₆H₄-C(O)NH-CH₂-(4-CO₂H-cyclohexyl) | ** |
| N34 | 2-HO₂C-C₆H₄-C(O)NH-(1H-imidazol-2-yl) | ** |

TABLE 2-continued

Additional Compounds

| Compound | Structure | Activity[1] |
|---|---|---|
| N35 | 2-(oxazol-2-ylcarbamoyl)benzoic acid | ** |
| N36 | 2-(thiazol-2-ylcarbamoyl)benzoic acid | |
| N37 | 2-((5-phenyl-1H-imidazol-2-yl)carbamoyl)benzoic acid | |
| N38 | 2-((4-phenyloxazol-2-yl)carbamoyl)benzoic acid | ** |
| N39 | 2-((4-phenylthiazol-2-yl)carbamoyl)benzoic acid | ** |
| N42 | 2-(thiazol-5-ylcarbamoyl)benzoic acid | *** |
| N45 | 2-((2-phenylthiazol-5-yl)carbamoyl)benzoic acid | *** |
| N46 | 2-(pyridin-2-ylcarbamoyl)benzoic acid | |

TABLE 2-continued

Additional Compounds

| Compound | Structure | Activity[1] |
|---|---|---|
| N47 | 2-((5-cyanopyridin-2-yl)carbamoyl)benzoic acid | |
| N48 | 2-(pyridin-3-ylcarbamoyl)benzoic acid | |
| N49 | 2-((6-cyanopyridin-3-yl)carbamoyl)benzoic acid | |
| N50 | 2-(pyrimidin-2-ylcarbamoyl)benzoic acid | ** |
| N51 | 2-((5-cyanopyrimidin-2-yl)carbamoyl)benzoic acid | |
| N52 | 2-(pyrazin-2-ylcarbamoyl)benzoic acid | ** |
| N53 | 2-((5-phenylpyrimidin-2-yl)carbamoyl)benzoic acid | |
| PA02 | 2-((4-(hydroxycarbamoyl)phenyl)carbamoyl)benzoic acid | ** |

TABLE 2-continued

Additional Compounds

| Compound | Structure | Activity[1] |
|---|---|---|
| PA03 | 2-HO2C-C6H4-C(O)NH-C6H4-C(O)NHC(O)CH3 | |
| PA04 | 2-HO2C-C6H4-C(O)NH-C6H4-NHC(O)NH2 | |
| PA05 | 2-HO2C-C6H4-C(O)NH-C6H4-CH2CO2H | |
| PA06 | 2-HO2C-C6H4-C(O)NH-C6H4-tetrazole | *** |
| PA07 | 2-HO2C-C6H4-C(O)NH-C6H4-SO3H | *** |
| PA08 | 2-HO2C-C6H4-C(O)NH-C6H4-PO3H | ** |
| PM01 | 2-HO2C-C6H4-C(O)NH-C6H4-CH2OCH3 | |
| PM02 | 2-HO2C-C6H4-C(O)NH-C6H4-CH2OPh | ** |
| PM04 | 2-HO2C-C6H4-C(O)NH-C6H4-CH2-(pyrimidin-2-yl) | |
| PM05 | 2-HO2C-C6H4-C(O)NH-C6H4-(pyridin-2-yl) | ** |
| PM06 | 2-HO2C-C6H4-C(O)NH-C6H4-CH(OH)CH2OH | |
| PM08 | 2-HO2C-C6H4-C(O)NH-C6H4-CH2-morpholine | |
| PM09 | 2-HO2C-C6H4-C(O)NH-C6H4-CH2NHC(O)CH3 | |
| PM10 | 2-HO2C-C6H4-C(O)NH-C6H4-CH2NHC(O)NH2 | ** |
| PM11 | 2-HO2C-C6H4-C(O)NH-C6H4-CH2NHC(O)OMe | ** |

TABLE 2-continued

Additional Compounds

| Compound | Structure | Activity[1] |
|---|---|---|
| PM12 | 2-carboxy-N-[4-(guanidino)phenyl]benzamide·HCl | |
| PM15 | 2-carboxy-N-[4-(imidazol-1-ylmethyl)phenyl]benzamide | |
| PM16 | 2-carboxy-N-(2-oxo-2,3-dihydro-1H-benzimidazol-5-yl)benzamide | |
| PM17 | 2-carboxy-N-[4-(oxazol-2-yl)phenyl]benzamide | |
| PM18 | 2-carboxy-N-[4-(1H-imidazol-2-yl)phenyl]benzamide | ** |
| PM19 | 2-carboxy-N-[4-(thiazol-2-yl)phenyl]benzamide | |
| R01 | 2-(4-cyano-1H-benzimidazol-2-yl)benzoic acid | ** |
| R02 | 2-(5-cyano-1H-benzimidazol-2-yl)benzoic acid | |
| R04 | 2-(5-cyanobenzoxazol-2-yl)benzoic acid | |
| R04-1 | 2-(6-cyanobenzoxazol-2-yl)benzoic acid | |
| R06-1 | 2-(6-cyanobenzothiazol-2-yl)benzoic acid | ** |
| R07 | 2-[(4-cyanophenylsulfonyl)amino]benzoic acid | ** |
| R08 | 2-[N-(4-cyanophenyl)sulfamoyl]benzoic acid | |
| R09 | 2-(4-cyanobenzamido)benzoic acid | |

TABLE 2-continued

Additional Compounds

| Compound | Structure | Activity[1] |
|---|---|---|
| R10 | 2-(3-(4-cyanophenyl)ureido)benzoic acid | ** |
| R11 | 2-((4-cyanobenzyl)amino)benzoic acid | |
| R14 | 2-(4-(carboxy)benzamido)benzoic acid | |

[1] **, chondrogenic nodules formed in at least 25% but less than 50% of cells.
***, chondrogenic nodules formed in at least 50% but less than 75% of cells.
****, chondrogenic nodules formed in at least 75% of cells.

Example 3. Rapid Phenotypic Cartilage Nodule Formation by hMSC Cultures after Incubation with 100 nM PRO1

Primary hMSCs grown in a 96 well Greiner plates (50,000/well) were incubated for 4 days in the presence of the 5 uM of each DMSO or 100 nM of PRO1. On day 4, the cells were fixed with 4% formalin for 10 minutes, washed and stained with 1 µg/ml of Rhodamine B for 2 hours at room temperature. The wells were imaged to display the formation of a cartilage nodule and phenotypic change associated with stimulation of MSCs by PRO1.

Example 4. Confirmation of Cartilage-Specific Protein Expression and Chondro-Protective Properties of PRO1

Primary hMSCs were plated (10,000/well) in 384-well plates and cultured for 18 days. The cells were fixed with 4% formalin, permeabilized with triton (0.5%), digested with 0.5 mg/ml collagenase II to unwind the collagen fibrils, and then immunostained with an antibody recognizing type II collagen. DAPI (2 µg/ml) was added to visualize the nuclei. The chondrogenic nodules stained positive for type II collagen but lacked expression of type X collagen and osteocalcin, markers for chondrocyte hypertrophy and osteoblasts, respectively (not shown). 10,000 hMSCs (passages 3-5) were plated in Greiner 384-well low-bottom plates on day 1. The cells were allowed to adhere and stimulated for 48 hrs (days 2-3) with the indicated stimuli in MSC growth media (Millipore). The media was then removed and replaced with serum-free DMEM for an additional 16 days. This media was replenished on days 10 and 15 of the assay.

Primary bovine chondrocytes were isolated from the articular surfaces from mature knees. After one week of culture, 8,500 cells were trypsinized and plated in Greiner 384-well white clear-bottom plates in growth media. Following 24 hrs of culture, the media was removed and replaced with DMEM containing 20 ng/ml TNFα and 10 ng/ml oncostatin M. The cells were treated for 48 hours with and without the small molecules to assess the inhibition of the cytokine induced-NO release. 20 µl of the supernatant was mixed with 20 µl of the Greiss reagent and quantitated at 540 nm as described by the Promega kit instructions. Bovine cartilage explants (cut in circular explants in a 96 well plate) were cultured in the presence of 20 ng/ml TNFα and 10 ng/ml oncostatin M to induce GAG release for 72 hours (FIG. 2D). PRO1 was added at the indicated concentrations during the entire 72 hrs. Incubation with 1 µM TGFβ3 (or less) and multiple doses of 1×ITS/100 nM dexamethasone did not have the same degree of chondro-protective activities. Parafin sections were hydrated, incubated in low pH Antigen unmasking solution (Vector) at 90 C for 10 minutes, permeabilized with 0.1% collagenase II (only for the sections stained with type II collagen) for 10 minutes, blocked with CAS block for 10 minutes and then incubated with the primary antibody (type II collagen, aggrecan or Timp1) antibody (Abcam) overnight at 4 C. The antigens were visualized through standard ABC detection methods and developed with DAB. Representative of 3 sections stained/treatment group (independent experiments). See FIG. 2A-E.

Figure 3A:
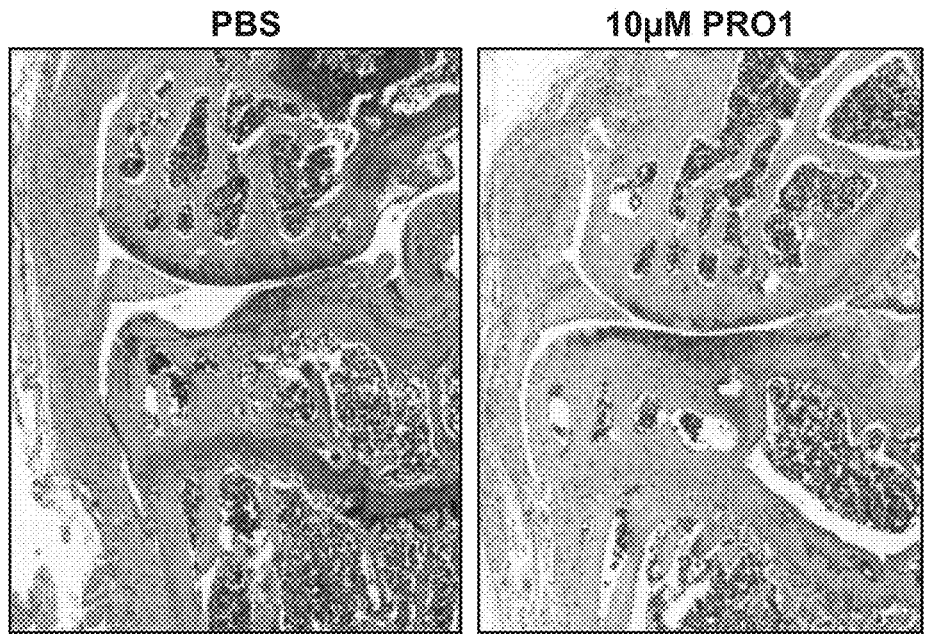
FIG. 3A shows the histological analysis of collagenase-induced joint damage in C57BL/10 mice with and without treatment via IA injection of PRO1 (AKT).
Figure 3B:
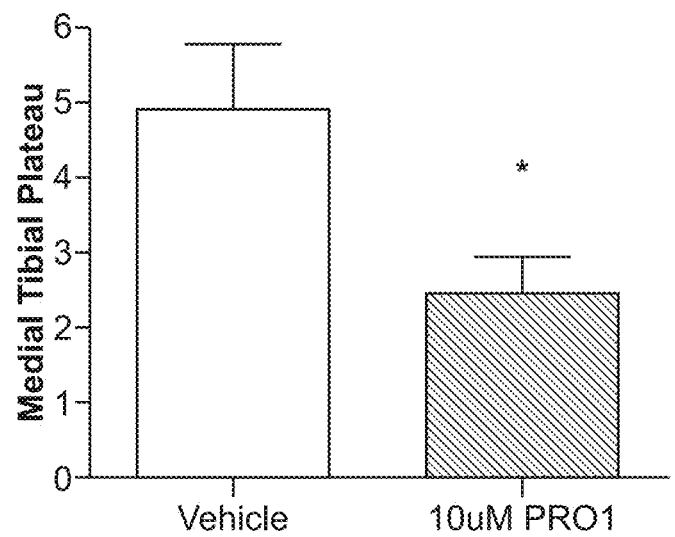
FIG. 3B shows the total medial tibial plateau joint score as determined by two blinded observers using the OARSI scoring system.
Figure 3C:
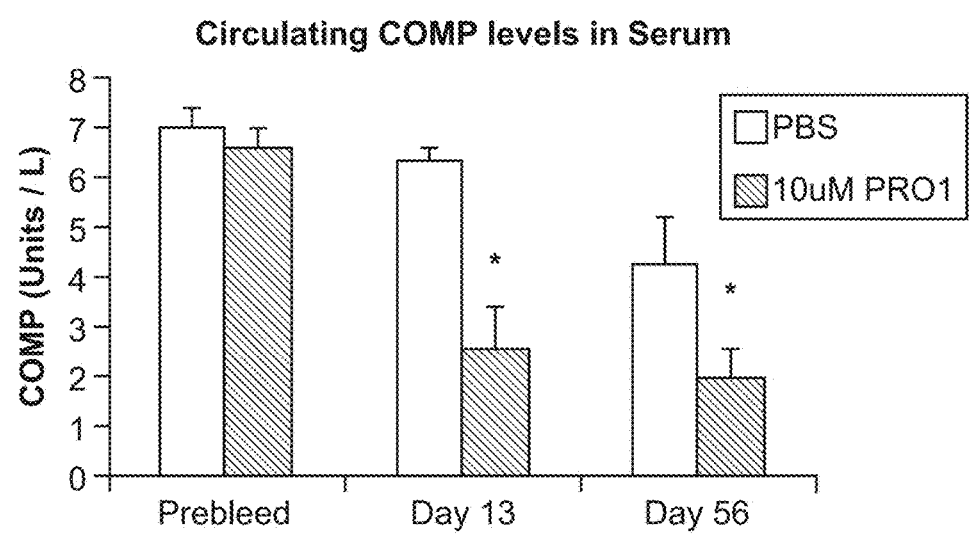
FIG. 3C shows the ELISA determination of circulating COMP in peripheral blood serum drawn from C57BL/10 mice during and after the course of treatment via IA injection of PRO1 (AKT).

Example 5. PRO1 Reduced Cartilage Damage and Circulating COMP Levels after Induction of Knee Joint Trauma by Collagenase VII IA injections of C57BL/10 mice with collagenase VII (12 U/knee) induced joint damage through digestion of the ligament of the knee. The mice were dosed intra-articularly on days 7 and 21 with 10 µM PRO1 or PBS. On day 56 the mice were euthanized for histopathological analyses. Parafin blocks were sectioned at 5 um and stained with Safranin O, and representative data was collected for the PBS- and PRO1-treated mice (FIG. 3A). The total medial tibial plateau joint score was determined by two blinded observers and averaged to represent the data shown here using the OARSI scoring system (FIG. 3B). Peripheral blood was collected from each mouse by retro-orbital bleeding on day 1, day 13 and day 56. The circulating COMP was determined by the Animal COMP ELISA kit according to the manufacturer's instructions (MDBioproducts, St Paul, Minn.). Pooled data, 10 mice/group (FIG. 3C).

Example 6. Surgical Induction of Cartilage Injury: Inhibition of CTX-II Peptide in Plasma and Protection of Cartilage Damage by PRO1

Figure 4A:
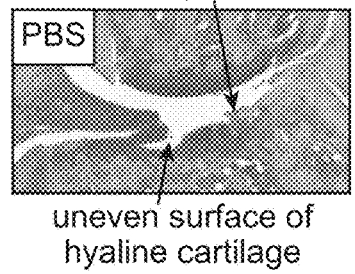
FIG. 4A shows the visualization of the medial tibial plateau from representative female 129SVE mice during treatment of surgically-induced cartilage injury via IA injection of PRO1 (AKT).
Figure 4A:
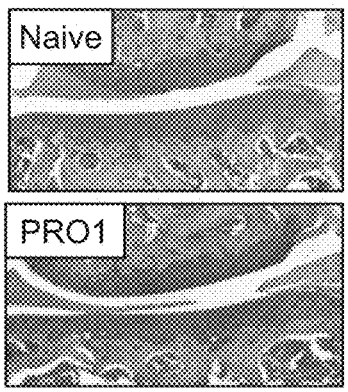
Figure 4B:
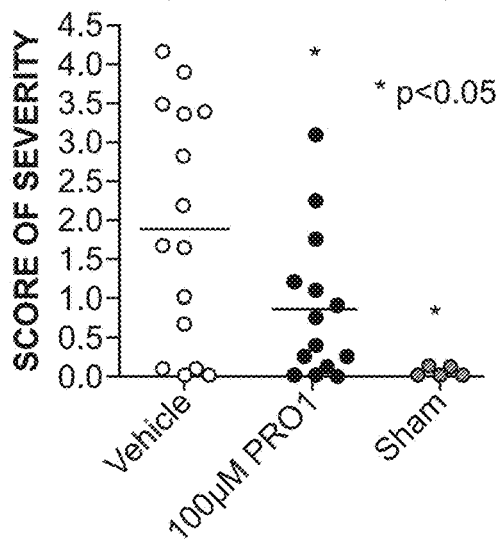
FIG. 4B shows the joint severity scores on day 28 after cartilage injury, as determined by histomorphometric analysis and grading by two blinded observers using a modified OARSI scoring system.
Figure 4C:
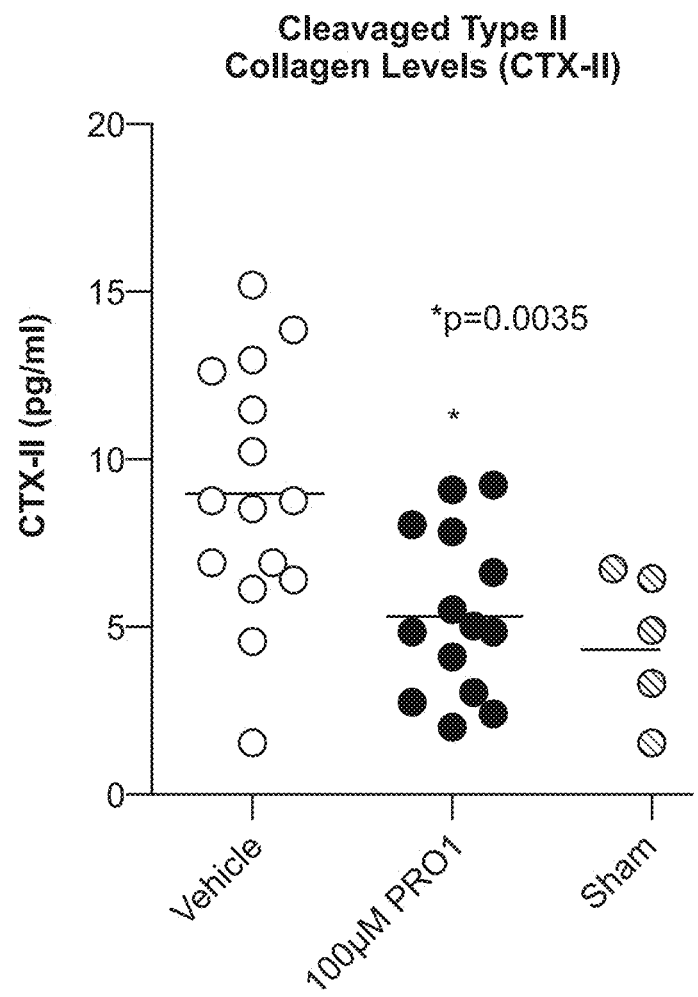
FIG. 4C shows the ELISA determination of cleaved type II collagen fragments (CTX-II) levels in peripheral blood serum collected 28 days after cartilage injury.

Surgical transection of the ACL, MCL, and MMTL was performed to induce cartilage injury in female 129SVE mice. Mice were dosed by IA injection on days 7, 14 and 21. The medial tibial plateaus from representative mice were assessed on day 28 (FIG. 4A). Histomorphometric analyses and grading by two blinded observers using a modified OARSI scoring system determined the joint severity scores of the lateral tibial plateau on day 28 after surgical induction (FIG. 4B). At 28 days, peripheral blood was collected by retro-orbital bleeding and the serum was used to determine the cleaved type II collagen fragments (CTX-II levels) by ELISA (Serum Pre-Clinical Cartilaps, Immunodiagnostic Systems, Fountain Hills, Ariz.). n=15/treatment group (FIG. 4C).

Example 7. Surgical Induction of OA: Alleviation of OA-Induced Pain

Figure 5A:
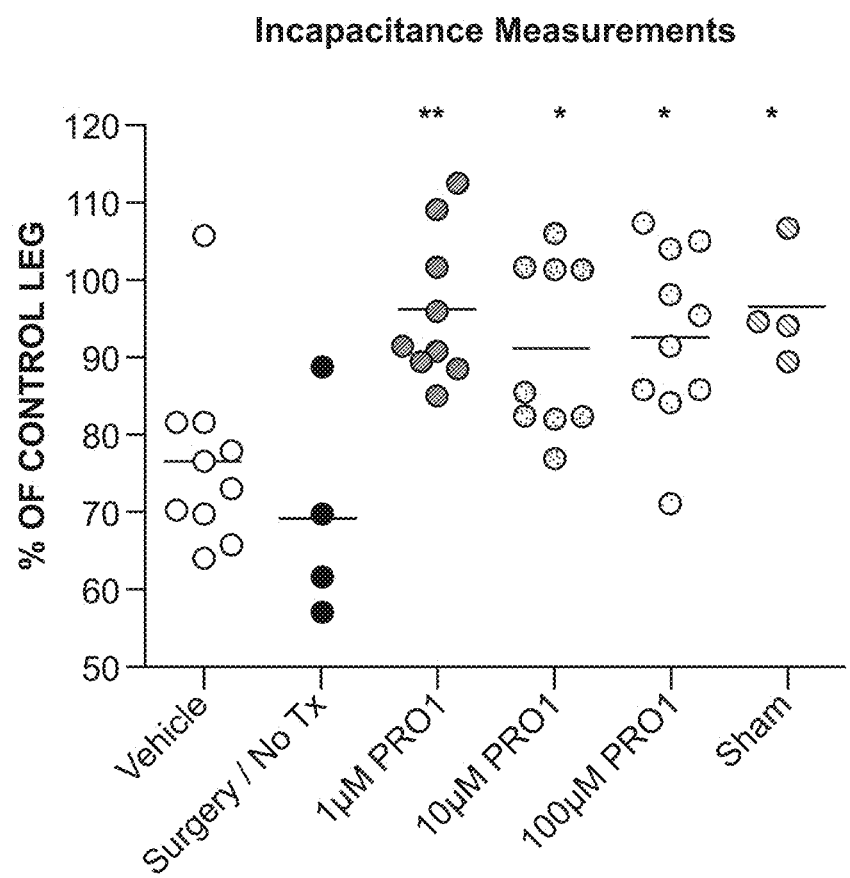
FIG. 5A shows the redistribution of weight to the hind legs by female 129SVE mice after IA injection of PRO1 (AKT) for treatment of surgically-induced cartilage injury.
Figure 5B:
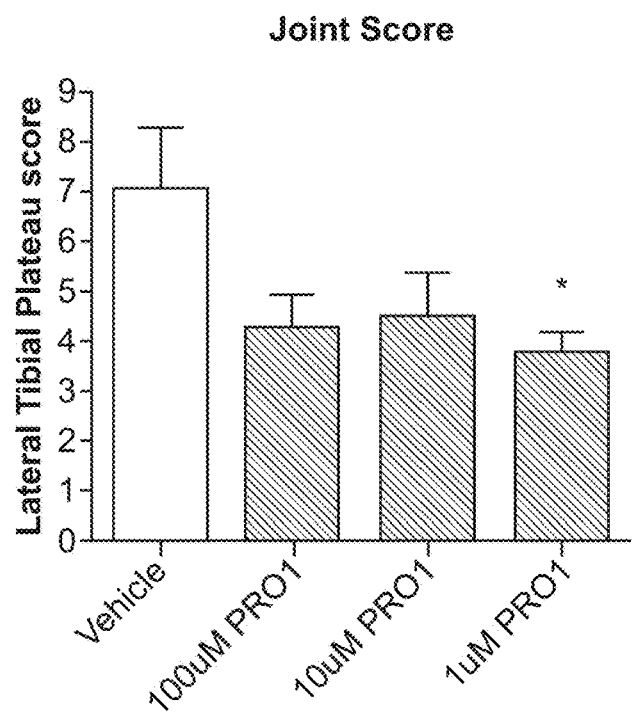
FIG. 5B shows the joint severity scores of the lateral tibial plateau on day 56 after cartilage injury, as determined by histomorphometric analysis and grading by two blinded observers using a modified OARSI scoring system.
Figure 5C:
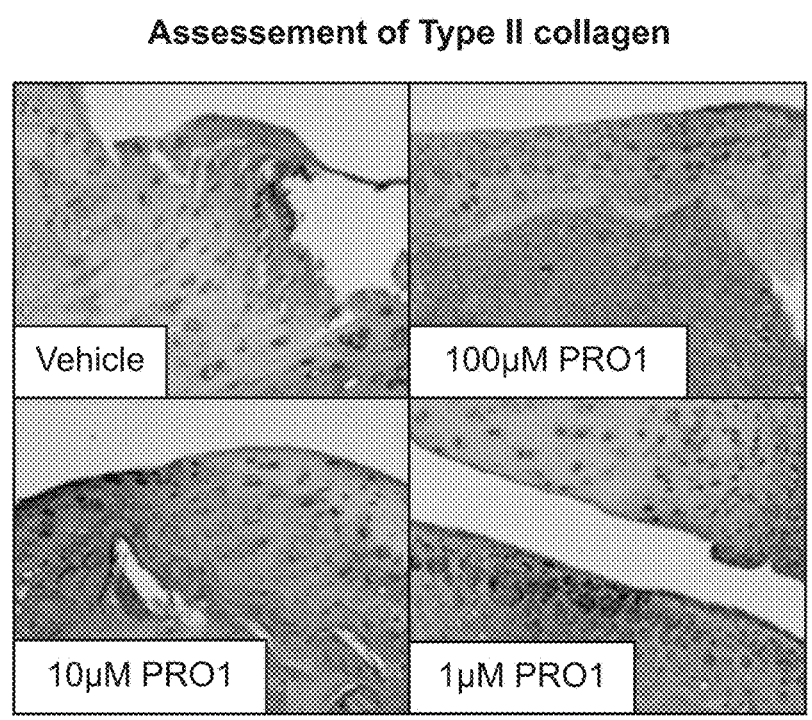
FIG. 5C shows the immunohistochemical analysis of type II collagen in representative mice following IA injection of PRO1 (AKT) for treatment of surgically-induced cartilage injury.

Surgical transection of the ACL, MCL, and MMTL was performed to induce cartilage injury in female 129SVE mice. Mice were dosed by IA injection on days 7, 14, 21 and 28 once/week. On day 42, incapacitance measurements were used to determine the percentage of weight the mouse distributed to each hind leg. 10 measurements were taken per mouse and averaged for each point in FIG. 5A. (n=10 mice/group except n=4 for sham and surgical groups). Histomorphometric analyses and grading by two blinded observers using a modified OARSI scoring system determined the joint severity scores of the lateral tibial plateau on day 56 after surgical induction (FIG. 5B). Parafin sections were hydrated, incubated in low-pH antigen unmasking solution (Vector) at 90° C. for 10 minutes, permeabilized with 0.1% collagenase II for 10 minutes, blocked with CAS block for 10 minutes, and then incubated with 1:200 dilution of type II collagen antibody (Abcam) overnight at 4° C. The antigen was visualized through standard ABC detection methods and developed with DAB (FIG. 5C).

Figure 6A:
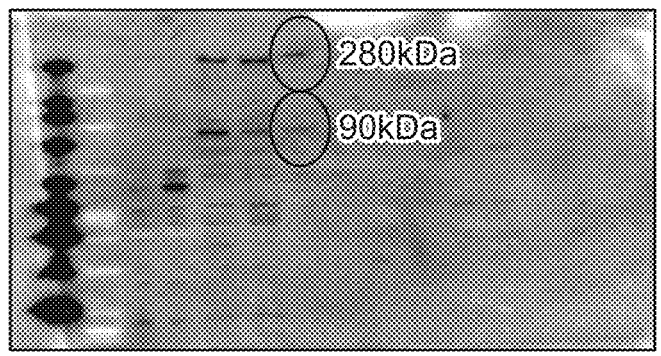
FIG. 6A shows the detection of biotinylated species resulting from reaction of a biotin-PRO1-azide (AKT-azide) analogue with closely associated proteins in cultured cells, as analyzed by Western blotting of fractionated hMSC lysates.
Figure 6B:
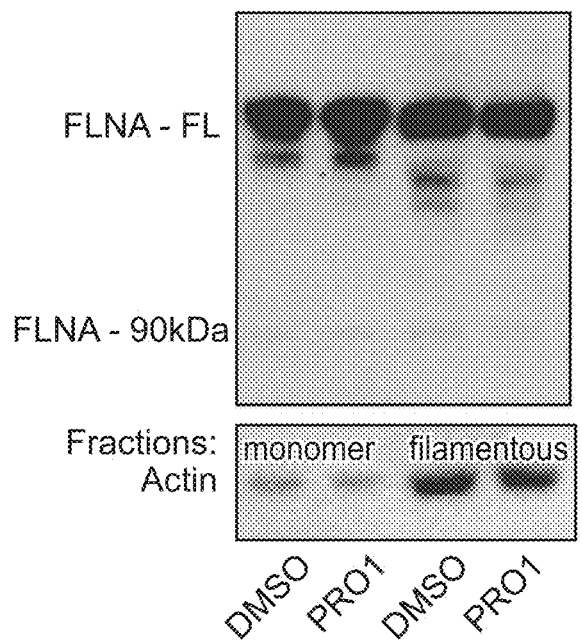
FIG. 6B shows expression levels of FLNA in hMSCs cultured in the presence of PRO1 (AKT), as assessed by Western blotting.
Figure 6C:
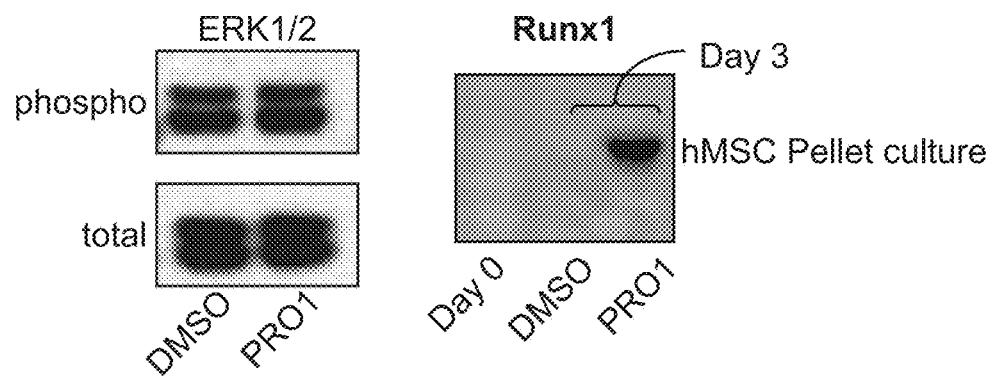
FIG. 6C shows the expression levels of PEBP2β/Runx1 pathway members in hMSCs treated with PRO1 (AKT) in monolayer or pellet cultures, as assessed by Western blotting.
Figure 6C:
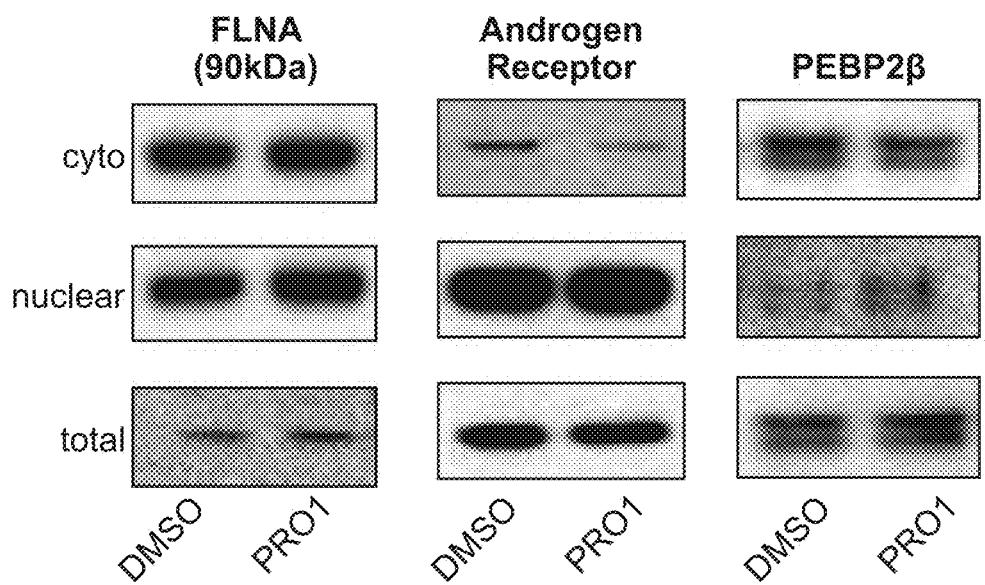

Example 8. PRO1 Interacts with FLNA and Regulates the PEBP2β/Runx1 Pathway to Induce Chondrogenesis To identify the interaction of PRO1 and FLNA, 5 μM biotin-PRO1-azide was added to hMSCs in the differentiation media in the absence or presence of a 50-fold molar excess of PRO1 and incubated for 30 min. 254-nm light was applied to the cells for another 30 min. Cells were lysed in lysis buffer (20 mM Tris-HCl, pH=7.4, 150 mM NaCl, 1 mM EDTA, 1 mM DTT, 0.5% v/v Triton X-100, protease inhibitor cocktail), passed through 26 1/2 gauge needles 20 times, and centrifuged at 12,000 rpm for 30 min. The supernatant was subjected to ammonium sulfate precipitation fractionation. Fractions were analyzed by Western blotting using an anti-biotin antibody (FIG. 6A). Fractions containing 20-40% ammonium sulfate were precipitated using trichloroacetic acid (TCA) and resuspended in isoelectric focusing sample buffer and subjected to 2D SDS-PAGE and Western blotting against biotin. Proteins specifically labeled by biotin-PRO1-azide were recognized, and the corresponding spots on a parallel gel visualized by silver staining were excised. These proteins were identified by mass spectrometry proteomics analysis. hMSCs were treated in monolayer or pellet culture (as indicated in FIG. 6B-6C) for 24-72 hrs. 15 μg of protein was separated by SDS-PAGE and hMSCs were fractionated (as indicated in FIG. 6B-6C) into cytosolic and nuclear fractions or monomeric and filamentous components as previously described.

Figure 7:
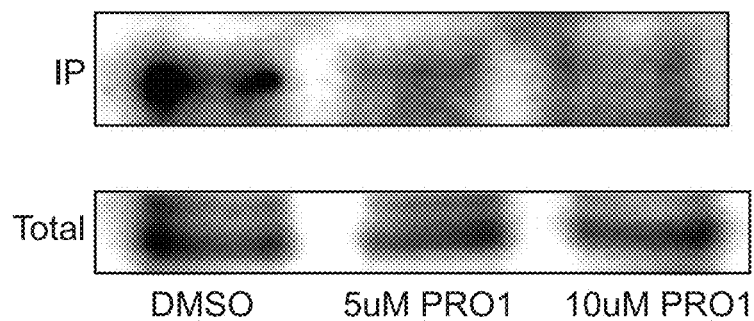
FIG. 7 shows the inhibition of FLNA/PEB2β interactions by PRO1 (AKT), as assessed by immunoprecipitation and Western blotting with the indicated antibodies.
Figure 8:
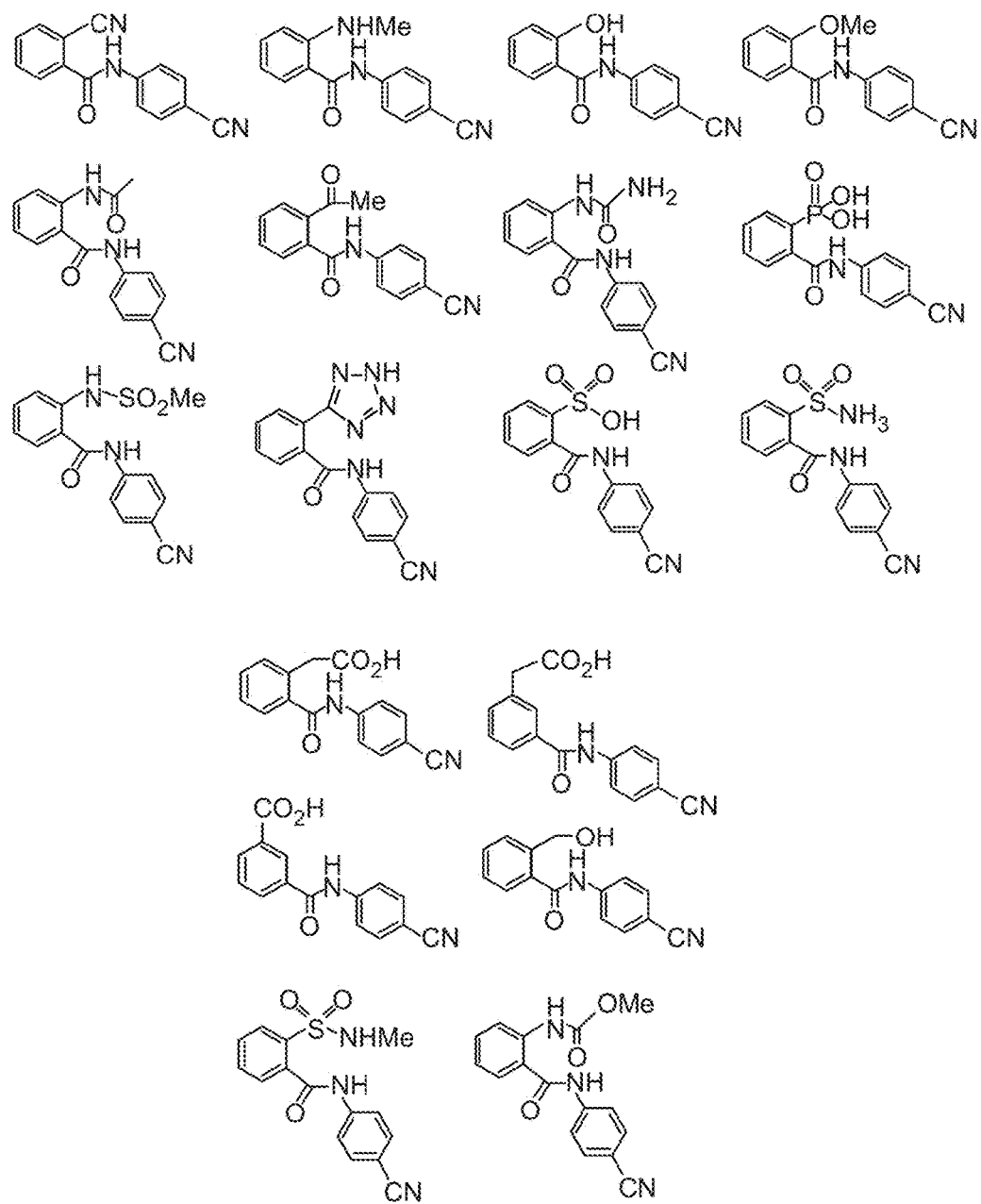
FIG. 8 shows compounds of the present invention.

Example 9. PRO1 Inhibits the Protein Interactions Between FLNA PEBP2β hMSCs were treated with PRO1 for 12 hr and lysed as above. 2 μg of anti-PEBP23 antibody was added to the cell lysate and incubated overnight at 4° C. prior to addition of agarose beads bearing immobilized protein A/G. After incubation of the lysate with the protein A/G beads for 1 hour, the beads were collected by centrifugation at 2,000 rpm and washed 3 times with lysis buffer. 30 μL of 2×SDS sample buffer was added to the beads and boiled for 5 min. Proteins were analyzed by Western blotting using antibodies as indicated in FIG. 7.

| Compound | Route | Dose mg/kg | Day | Animal ID | $T_{1/2}$ h | $T_{max}$ h | $C_{max}$ nM | $AUC_{0-inf}$ h * nM | Plasma Conc. (nM) 1.00 | 3.00 | 7.00 | 24.00 |
|---|---|---|---|---|---|---|---|---|---|---|---|---|
| AKT093 | intra-articular (into the joint) | $1.6 \times 10^{-4}$ mmol/kg (0.05 mg/kg) (QD) | 1 | 1 | 1.9 | 1.0 | 133.6 | 342.3 | 134 | 28 | 13 | BLQ |
|  |  |  |  | 2 | 1.6 | 1.0 | 77.8 | 213.4 | 78 | 24 | 6 | BLQ |
|  |  |  |  | 3 | 2.4 | 1.0 | 95.5 | 376.9 | 95 | 49 | 16 | BLQ |
| LOQ = 1 ng/mL (Accuracy: 99.4%) |  |  |  | Mean | 2.0 | 1.0 | 102.3 | 310.9 | 102.3 | 33.6 | 11.8 | BLQ |

Comments:
1) Compound was dosed at 0.05 mg/kg by intra-articular injection.
2) After IA dosing, the compound was rapidly absorbed and the Cmax was ~100 nM.
3) The bioavailability was ~22%
4) Short T1/2 (~2 h).

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:
1. A method for stimulating chondrocyte proliferation and cartilage production in cartilaginous tissues in a mammal, the method comprising administering to the mammal a composition comprising a therapeutically effective amount of a compound of formula I:

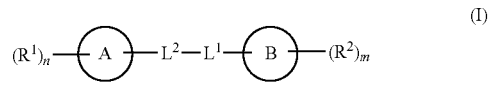

(I)

wherein
each of ring A and ring B are independently selected from the group consisting of cycloalkyl, aryl and heteroaryl;
each $R^1$ and $R^2$ is independently selected from the group consisting of H, $C_{1-6}$ alkyl, $C_{2-6}$ alkenyl, $C_{2-6}$ alkynyl, $C_{1-6}$ alkoxy, $C_{1-6}$ heteroalkyl, halogen, $C_{1-6}$ haloalkyl, C$_{1-6}$ haloalkoxy, C$_{1-6}$ alkyl-CN, C$_{1-6}$ alkylhydroxy, —OR$^{2a}$, —NR$^{2b}$R$^{2d}$, C$_{1-6}$ alkyl-NR$^{2b}$R$^{2d}$, —C(O)R$^{1a}$, —C(O)R$^{2d}$, —C(O)OR$^{2a}$, C$_{1-6}$ alkyl-C(O)OR$^{2b}$, —OC(O)R$^{2b}$, —OC(O)OR$^{2b}$, —C(O)NR$^{2a}$R$^{2b}$, —C(O)N(OH)R$^{2b}$, —NR$^{2b}$C(O)R$^{2c}$, C$_{1-6}$ alkyl-NR$^{2b}$C(O)R$^{2c}$, —NR$^{2b}$C(O)OR$^{2c}$, C$_{1-6}$ alkyl-NR$^{2b}$C(O)OR$^{2c}$, —OC(O)NR$^{2b}$R$^{2c}$, —NR$^{2b}$C(O)NR$^{2b}$R$^{2c}$, —NR$^{2b}$C(NR$^{2b}$)N R$^{2b}$R$^{2c}$, —C(O)NR$^{2b}$C(O)R$^{2b}$, C$_{1-6}$ alkyl-NR$^{2b}$C(O)NR$^{2b}$R$^{2c}$, —SR$^{2a}$, —SO$_2$R$^{2b}$, —SO$_2$OR$^{2b}$, —SO$_2$NR$^{2b}$R$^{2d}$, —NR$^{2b}$SO$_2$ R$^{2b}$, —P(O)(OR$^{2b}$)$_2$, —B(OR$^{2b}$), —CN, —NO$_2$, —N$_3$, heterocycloalkyl, aryl, heteroaryl, C$_{1-6}$ alkyl-heterocycloalkyl, C$_{1-6}$ alkyl-aryl, C$_{1-6}$ alkyl-O-aryl, C$_{1-6}$ alkyl-heteroaryl, and heteroaryl-aryl, and wherein the heterocycloalkyl, aryl and heteroaryl groups are optionally substituted with 1 to 2 R$^{2a}$ groups;

R$^{1a}$ is selected from the group consisting of —OR$^{1b}$ and —NR$^{1b}$R$^{1c}$;

R$^{1b}$ and R$^{1c}$ are each independently selected from the group consisting of H, C$_{1-6}$ alkyl, C$_{2-6}$ alkenyl, C$_{2-6}$ alkynyl, cycloalkyl, heterocycloalkyl, aryl, heteroaryl, C$_{1-6}$ alkyl-aryl, and C$_{1-6}$ alkyl-heteroaryl, wherein the cycloalkyl, heterocycloalkyl, aryl and heteroaryl groups are optionally substituted with from 1 to 4 Rid groups;

each R$^{1d}$ is independently selected from the group consisting of H, C$_{1-6}$ alkyl, C$_{1-6}$ alkoxy, and —NO$_2$;

each R$^{2a}$ is independently selected from the group consisting of H, C$_{2-6}$ alkenyl, C$_{2-6}$ alkynyl, cycloalkyl, heterocycloalkyl, aryl, heteroaryl, C$_{1-6}$ alkyl-cycloalkyl, C$_{1-6}$ alkyl-heterocycloalkyl, C$_{1-6}$ alkyl-aryl and C$_{1-6}$ alkyl-heteroaryl, optionally substituted with 1 to 2 R$^{2b}$ groups;

each R$^{2b}$ and R$^{2c}$ is independently selected from the group consisting of H, and C$_{1-6}$ alkyl;

each R$^{2d}$ is independently selected from the group consisting of H, C$_{1-6}$ alkyl, cycloalkyl, heterocycloalkyl, aryl, heteroaryl, C$_{1-6}$ alkyl-cycloalkyl, C$_{1-6}$ alkyl-heterocycloalkyl, C$_{1-6}$ alkyl-aryl and C$_{1-6}$ alkyl-heteroaryl, each optionally substituted with 1 to 2 R$^{2b}$ groups;

each of L$^1$ and L$^2$ are independently selected from the group consisting of a bond, C$_{1-6}$ alkylene, C$_{2-6}$ alkenylene, C$_{1-6}$ alkylene-O—, —O—C$_{1-6}$ alkylene, C$_{1-6}$ alkylene-NR$^{3a}$—, —NR$^{3a}$—C$_{1-6}$ alkylene, —C(O)—, C$_{1-6}$ alkylene-C(O)—, —C(O)—C$_{1-6}$ alkylene-NH—, —NH—C$_{1-6}$ alkylene-C(O)—, —C(O)N H—, —NHC(O)—, C$_{1-6}$ alkylene-NHC(O)—, —SO$_2$NH—, —NHSO$_2$—, —NHC(O)NH—, cycloalkylene, —N═N—, and —C(R$^{3a}$)═N (R$^{3c}$)—, wherein the alkylene group is optionally substituted with from 1-4 R$^{3b}$ groups; R$^{3a}$ is selected from the group consisting of H, and C$_{1-6}$ alkyl;

each R$^{3b}$ is independently selected from the group consisting of H, C$_{1-6}$ alkyl, halogen, —OR$^{3a}$ and —NR$^{3a}$R$^{3a}$;

R$^{3c}$ is absent or —OH;

alternatively, L$^2$ is combined with R$^1$, L$^1$ is combined with L$^2$, L$^1$ is combined with R$^2$, two R$^1$ groups on adjacent ring atoms, or two R$^2$ groups on adjacent ring atoms are combined to form a 5-6 membered heterocycloalkyl with from 1 to 3 heteroatoms selected from N, O and S, or a 5-6 membered heteroaryl with from 1 to 3 heteroatoms selected from N, O and S, and optionally substituted with from 1 to 3 groups selected from the group consisting of H, C$_{1-6}$ alkyl and oxo;

subscripts m and n are each an integer from 1 to 3;

wherein:

(a) L$^1$ is a bond, L$^2$ is —C(O)NH—, ring B is phenyl, and at least one R$^2$ is —CN or phenyl, or (b) at least one R$^1$ is —C(O)OH, ring A is phenyl, L$^2$ is —C(O)NH—, and L$^1$ is a bond or C$_{1-6}$ alkylene, or (c) each of ring A and ring B is phenyl, at least one R$^1$ is —C(O)OH or combined with L$^2$, and at least one R$^2$ is selected from the group consisting of H, —CN and —C(O)OH;

wherein when R$^1$ is —CO$_2$H, subscript n is 1, ring A is phenyl, L$^2$ is —C(O)NH—, L$^1$ is a bond, ring B is phenyl, subscript m is 1, and R$^2$ is phenyl, then the phenyl of R$^2$ is substituted with C$_{1-6}$ alkyl, or salts and isomers thereof, thereby stimulating chondrocyte proliferation and cartilage production in the cartilaginous tissues in the mammal.

2. The method of claim 1, wherein the compound has the structure:

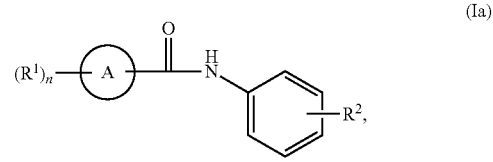

(Ia)

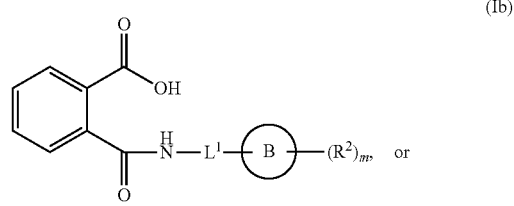

(Ib)

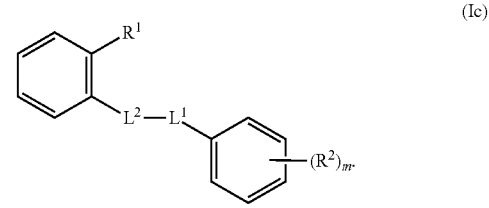

(Ic)

3. The method of claim 1, wherein the compound has the structure:

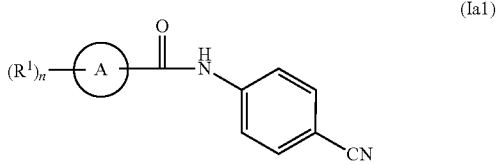

(Ia1)

wherein each R$^1$ is independently selected from the group consisting of C$_{2-6}$ alkenyl, C$_{2-6}$ alkynyl, C$_{1-6}$ alkoxy, C$_{1-6}$ heteroalkyl, halogen, C$_{1-6}$ haloalkyl, C$_{1-6}$ haloalkoxy, C$_{1-6}$ alkyl-CN, C$_{1-6}$ alkylhydroxy, —OR$^{2a}$, —NR$^{2b}$R$^{2d}$, C$_{1-6}$ alkyl-NR$^{2b}$R$^{2d}$, —C(O)R$^{1a}$, —C(O)R$^{2d}$, —C(O)OR$^{2a}$, C$_{1-6}$ alkyl-C(O)

$OR^{2b}$, $-OC(O)R^{2b}$, $-OC(O)OR^{2b}$, $-C(O)NR^{2a}R^{2b}$, $-C(O)N(OH)R^{2b}$, $-NR^{2b}C(O)R^{2c}$, $C_{1-6}$ alkyl-$NR^{2b}C(O)R^{2c}$, $-NR^{2b}C(O)OR^{2c}$, $C_{1-6}$ alkyl-$NR^{2b}C(O)OR^{2c}$, $-OC(O)NR^{2b}R^{2c}$, $-NR^{2b}C(O)OR^{2c}$, $-OC(O)NR^{2b}R^{2c}$, $-NR^{2b}C(NR^{2b})NR^{2b}R^{2c}$, $-C(O)NR^{2b}C(O)R^{2b}$, $C_{1-6}$ alkyl-$NR^{2b}C(O)NR^{2b}R^{2c}$, $-SR^{2a}$, $-SO_2R^{2b}$, $-SO_2OR^{2b}$, $-SO_2NR^{2b}R^{2d}$, $-NR^{2b}SO_2R^{2b}$, $-P(O)(OR^{2b})_2$, $-B(OR^{2b})$, $-CN$, $-NO_2$, $-N_3$, heterocycloalkyl, aryl, heteroaryl, $C_{1-6}$ alkyl-heterocycloalkyl, $C_{1-6}$ alkyl-aryl, $C_{1-6}$ alkyl-O-aryl, $C_{1-6}$ alkyl-heteroaryl, and heteroaryl-aryl, and wherein the heterocycloalkyl, aryl and heteroaryl groups are optionally substituted with 1 to 2 $R^{2a}$ groups;

each of $R^{2a}$, $R^{2b}$, $R^{2c}$ and $R^{2d}$ are independently selected from the group consisting of H and $C_{1-6}$ alkyl; and ring A is selected from the group consisting of phenyl, biphenyl and pyridyl, wherein when ring A is phenyl and at least one $R^1$ is $-C(O)OH$, then subscript n is 2 or 3.

4. The method of claim 1, wherein the compound has the structure:

(Ia2)

wherein
$R^1$ is selected from the group consisting of $C_{1-6}$ alkyl and $-C(O)OR^{2b}$; and
$R^2$ is selected from the group consisting of $-CN$ and Ph.

5. The method of claim 1, wherein the compound has the structure:

(Ib)

wherein
each $R^2$ is independently selected from the group consisting of H, $C_{1-6}$ haloalkoxy, $C_{1-6}$ alkyl-$NR^{2b}R^{2d}$, $-C(O)OR^{2b}$, $-C(O)N(OH)R^{2b}$, $C_{1-6}$ alkyl-$NR^{2b}C(O)OR^{2c}$, $C_{1-6}$ alkyl-$NR^{2b}C(O)NR^{2b}R^{2c}$, $-SO_2OR^{2b}$, $-PO_3H$, $-CN$, aryl, heteroaryl, and $C_{1-6}$ alkyl-O-aryl;
ring B is selected from the group consisting of cyclohexyl, phenyl, imidazole, oxazole, thiazole, pyrimidine, and pyrazine; and
$L^1$ is selected from the group consisting of a bond and $-CH_2-$;

wherein
when $R^2$ is $C_{1-6}$ alkyl-$NR^{2b}R^{2d}$, then one of $R^{2b}$ and $R^{2d}$ is $C_{1-6}$ alkyl,
when $R^2$ is $-C(O)OH$, then $L^1$ is $-CH_2-$ or ring B is cyclohexyl, or both,
when $R^2$ is $-CN$, then $L^1$ is $-CH_2-$ or ring B is cyclohexyl, or both, and
when ring B is 2-thiazole, $R^2$ is unsubstituted phenyl.

6. The method of claim 1, wherein the compound has the structure:

(Ib)

wherein
each $R^2$ is independently selected from the group consisting of $C_{1-6}$ alkyl, halogen, $C_{1-6}$ alkylhydroxy, $C_{1-6}$ alkyl-$NR^{2b}R^{2d}$, $-C(O)R^{2d}$, $-C(O)OR^{2b}$, $-C(O)NR^{2b}R^{2c}$, $-SO_2NR^{2b}R^{2d}$m $-CN$, -heterocycloalkyl, and aryl, wherein the aryl groups are optionally substituted with halogen;
alternatively, two $R^2$ groups on adjacent ring atoms can be combined to form a 5-membered heterocycloalkyl;
ring B is selected from the group consisting of phenyl, thiazole and pyridyl; and
$L^1$ is selected from the group consisting of a bond and $-CH_2-$;
wherein
when $R^2$ is $C_{1-6}$ alkyl-$NR^{2b}R^{2d}$, then both of $R^{2b}$ and $R^{2d}$ are H,
when $R^2$ is $-C(O)OH$, then $L^1$ is a bond and ring B is phenyl,
when $R^2$ is $-CN$, then $L^1$ is a bond and ring B is phenyl, and
when ring B is 2-thiazole, then $R^2$ is substituted phenyl.

7. The method of claim 1, wherein the compound has the structure:

(Ic)

wherein
$R^1$ is $-C(O)OH$;
each $R^2$ is independently selected from the group consisting of $-CN$ and $-C(O)OH$;
each of $L^1$ and $L^2$ are independently selected from the group consisting of a bond, $C_{1-6}$ alkylene, $C_{2-6}$ alkenylene, $-C(O)-$, $C_{1-6}$ alkylene-$C(O)-$, $-C(O)-C_{1-6}$ alkylene-NH-, $-NH-C_{1-6}$ alkylene-C(O)—, —NHC(O)—, —SO$_2$NH—, —NHSO$_2$—, and —NHC(O)NH—;

wherein at least one of L$^1$ and L$^2$ is selected from the group consisting of —C(O)—, C$_{1-6}$ alkylene-C(O)—, —C(O)—C$_{1-6}$ alkylene-NH—, —NH—C$_{1-6}$ alkylene-C(O)—, —NHC(O)—, —SO$_2$NH—, —NHSO$_2$—, and —NHC(O)NH—;

alternatively, L$^2$ is combined with R$^1$, or L$^1$ is combined with R$^2$, to form a 5-6 membered heterocycloalkyl with from 1 to 3 heteroatoms selected from N, O and S, or a 5-6 membered heteroaryl with from 1 to 3 heteroatoms selected from N, O and S.

8. The method of claim 1, wherein the compound has the structure:

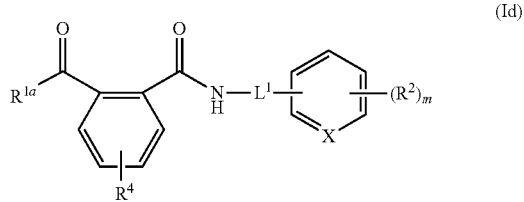

(Id)

R$^{1a}$ is selected from the group consisting of —OR$^b$ and —NR$^{1b}$R$^{1c}$;

R$^{1b}$ and R$^{1c}$ are each independently selected from the group consisting of H, C$_{1-6}$ alkyl, C$_{2-6}$ alkenyl, C$_{2-6}$ alkynyl, cycloalkyl, heterocycloalkyl, aryl, heteroaryl, C$_{1-6}$ alkyl-aryl, and C$_{1-6}$ alkyl-heteroaryl, wherein the cycloalkyl, heterocycloalkyl, aryl and heteroaryl groups are optionally substituted with from 1 to 4 Rid groups;

each R$^{1d}$ is independently selected from the group consisting of H, C$_{1-6}$ alkyl, C$_{1-6}$ alkoxy, and —NO$_2$;

each R$^2$ is independently selected from the group consisting of C$_{1-6}$ alkyl, C$_{1-6}$ alkoxy, halogen, C$_{1-6}$ haloalkyl, C$_{1-6}$ haloalkoxy, C$_{1-6}$ alkylamine, C$_{1-6}$ alkyl-CN, C$_{1-6}$ alkyl-OH, heterocycloalkyl, aryl, heteroaryl, C$_{1-6}$ alkyl-aryl, C$_{1-6}$ alkyl-heteroaryl, heteroaryl-aryl, —OR$^{2a}$, —NR$^{2b}$R$^{2d}$, —C(O)R$^{2d}$, —C(O)OR$^{2b}$, —OC(O)R$^{2b}$, —C(O)NR$^{2b}$R$^{2c}$, —NR$^{2b}$C(O)R$^{2c}$, —NR$^{2b}$C(O)OR$^{2c}$, —OC(O)NR$^{2b}$R$^{2c}$, —SO$_2$R$^{2a}$, —SO$_2$NR$^{2b}$R$^{2d}$, —CN, —NO$_2$, and —N$_3$, wherein the heterocycloalkyl, aryl and heteroaryl groups are optionally substituted with 1 to 2 R$^{2b}$ groups;

alternatively, two R$^2$ groups on adjacent ring atoms are combined to form a 5 to 6 membered heterocyclic ring having from 1 to 3 heteroatoms each independently selected from the group consisting of N, O and S, and optionally substituted with from 1 to 3 groups selected from the group consisting of H, C$_{1-6}$ alkyl and oxo;

each R$^{2a}$ is independently selected from the group consisting of H, C$_{2-6}$ alkenyl, C$_{2-6}$ alkynyl, cycloalkyl, heterocycloalkyl, aryl, heteroaryl, C$_{1-6}$ alkyl-cycloalkyl, C$_{1-6}$ alkyl-heterocycloalkyl, C$_{1-6}$ alkyl-aryl and C$_{1-6}$ alkyl-heteroaryl, optionally substituted with 1 to 2 R$^{2b}$ groups;

each R$^{2b}$ and R$^{2c}$ is independently selected from the group consisting of H, and C$_{1-6}$ alkyl;

each R$^{2d}$ is independently selected from the group consisting of H, C$_{1-6}$ alkyl, cycloalkyl, heterocycloalkyl, aryl, heteroaryl, C$_{1-6}$ alkyl-cycloalkyl, C$_{1-6}$ alkyl-heterocycloalkyl, C$_{1-6}$ alkyl-aryl and C$_{1-6}$ alkyl-heteroaryl, each optionally substituted with 1 to 2 R$^{2b}$ groups;

R$^4$ is independently selected from the group consisting of C$_{1-6}$ alkyl, halogen, C$_{1-6}$ haloalkyl, C$_{1-6}$ alkoxy, C$_{1-6}$ haloalkoxy, OH, —CO$_2$H, and —NO$_2$;

L$^1$ is selected from the group consisting of a bond, C$_{1-6}$ alkylene, —C(O)—, —C$_{1-6}$ alkylene-NH—, —C$_{1-6}$ alkylene-NHC(O)—, and heteroarylene; and X is selected from the group consisting of —CH— and —N—.

9. The method of claim 8, wherein the compound has the structure:

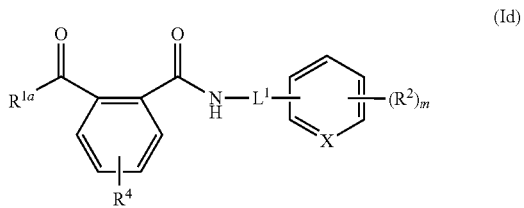

(Id)

wherein each R$^2$ is independently selected from the group consisting of C$_{1-6}$ alkyl, C$_{1-6}$ alkoxy, halogen, C$_{1-6}$ haloalkyl, C$_{1-6}$ alkyl-CN, C$_{1-6}$ alkyl-OH, heterocycloalkyl, aryl, heteroaryl, C$_{1-6}$ alkyl-aryl, C$_{1-6}$ alkyl-heteroaryl, heteroaryl-aryl, —OR$^{2a}$, —NR$^{2b}$R$^{2d}$, —C(O)R$^{2d}$, —OC(O)R$^{2b}$, —C(O)NR$^{2b}$R$^{2c}$, —NR$^{2b}$C(O)R$^{2c}$, —NR$^{2b}$C(O)OR$^{2c}$, —OC(O)NR$^{2b}$R$^{2c}$, —SO$_2$R$^{2a}$, —SO$_2$NR$^{2b}$R$^{2d}$, —CN, —NO$_2$, and —N$_3$, wherein the heterocycloalkyl, and aryl groups are optionally substituted with 1 to 2 R$^{2b}$ groups;

wherein when R$^2$ is —CN, then subscript m is 1, R$^{1a}$ is OH, R$^4$ is H, and L$^1$ is a bond.

10. The method of claim 8, wherein the compound has the structure:

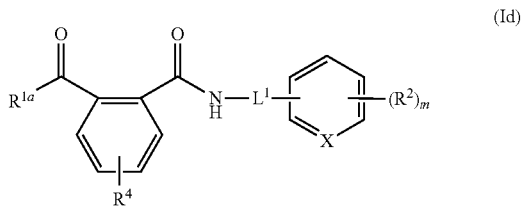

(Id)

wherein each R$^2$ is independently selected from the group consisting of C$_{1-6}$ alkyl, halogen, C$_{1-6}$ haloalkyl, C$_{1-6}$ alkyl-CN, C$_{1-6}$ alkyl-OH, heterocycloalkyl, aryl, heteroaryl, C$_{1-6}$ alkyl-aryl, C$_{1-6}$ alkyl-heteroaryl, heteroaryl-aryl, —OR$^{2a}$, —NR$^{2b}$R$^{2d}$, —C(O)R$^{2d}$, —OC(O)R$^{2b}$, —C(O)NR$^{2b}$R$^{2c}$, —NR$^{2b}$C(O)R$^{2c}$, —NR$^{2b}$C(O)OR$^{2c}$, —OC(O)NR$^{2b}$R$^{2c}$, —SO$_2$R$^{2a}$, —SO$_2$NR$^{2b}$R$^{2d}$, —CN, —NO$_2$, and —N$_3$, wherein the heterocycloalkyl, and aryl groups are optionally substituted with 1 to 2 R$^{2b}$ groups; and L$^1$ is a bond, wherein when R$^2$ is —CN, then subscript m is 1, R$^{1a}$ is OH, R$^4$ is H, and L$^1$ is a bond.

11. The method of claim 1, wherein the compound is selected from the group consisting of:

137
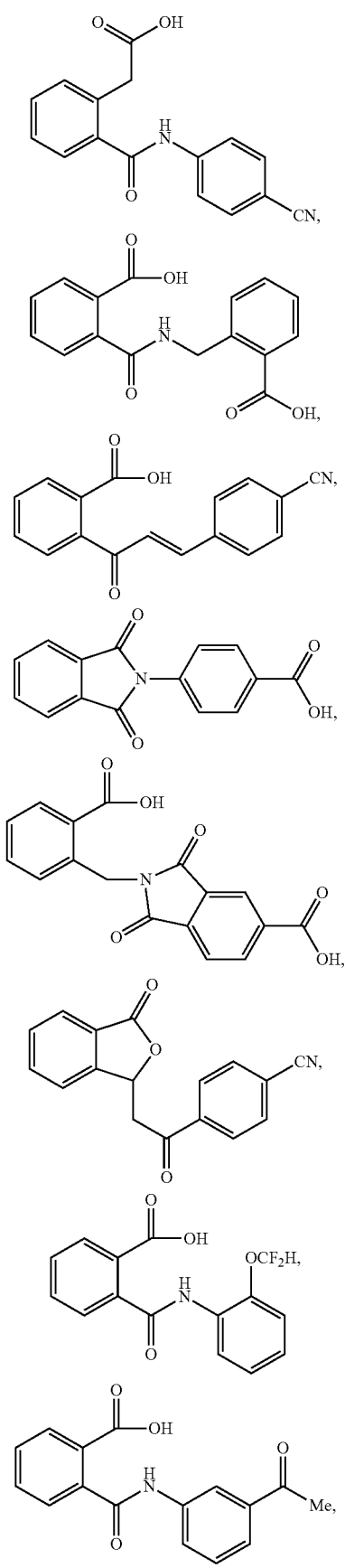
138
-continued
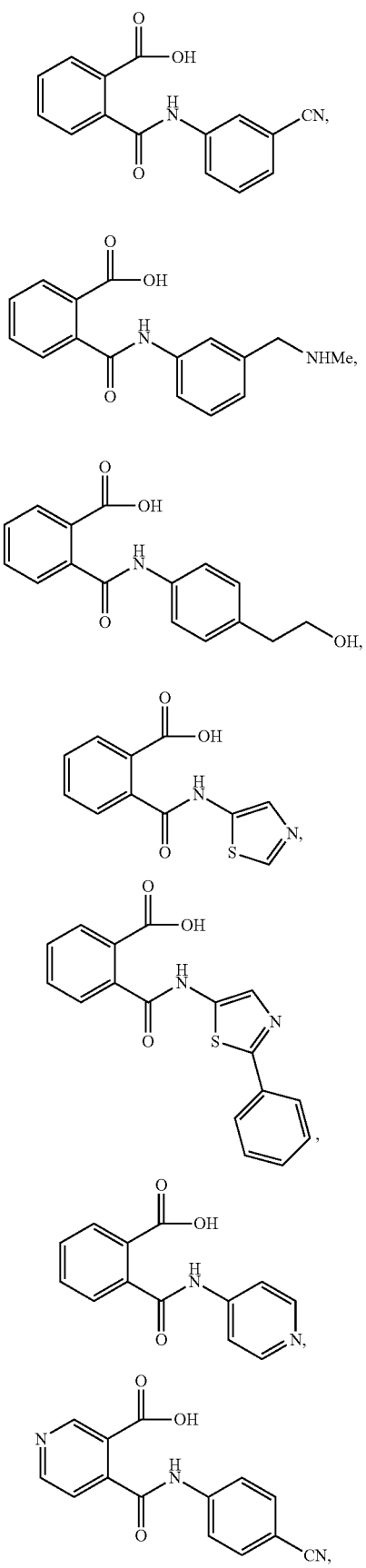

-continued

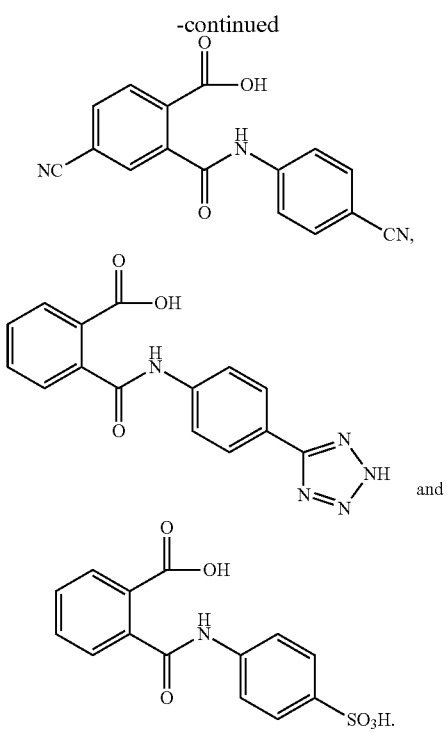

12. The method of claim 1, wherein the cartilaginous tissues have been damaged due to traumatic injury or chondropathy.

13. The method of claim 12, wherein the traumatic injury is selected from the group consisting of blunt trauma to the joint, and damage to ligaments.

14. The method of claim 13, wherein the damage to ligaments is selected from the group consisting of tearing of the anterior cruciate ligament, tearing of the medial collateral ligament, and a miniscal tear.

15. The method of claim 1, wherein the mammal is selected from the group consisting of a human, a dog, a horse and a cat.

16. A method of expanding chondrocyte populations in culture for autogenous or allogenic chondrocyte transplantation, the method comprising contacting chondrocyte populations in culture with a sufficient amount of a compound having the structure:

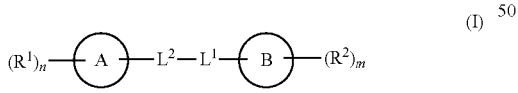

(I)

wherein
each of ring A and ring B are independently selected from the group consisting of cycloalkyl, aryl and heteroaryl;
each $R^1$ and $R^2$ is independently selected from the group consisting of H, $C_{1-6}$ alkyl, $C_{2-6}$ alkenyl, $C_{2-6}$ alkynyl, $C_{1-6}$ alkoxy, $C_{1-6}$ heteroalkyl, halogen, $C_{1-6}$ haloalkyl, $C_{1-6}$ haloalkoxy, $C_{1-6}$ alkyl-CN, $C_{1-6}$ alkylhydroxy, —$OR^{2a}$, —$NR^{2b}R^{2d}$ $C_{1-6}$ alkyl-$NR^{2b}R^{2d}$, —$C(O)R^{1a}$, —$C(O)R^{2d}$, —$C(O)OR^{2a}$, $C_{1-6}$ alkyl-C(O)$OR^{2b}$, —$OC(O)R^{2b}$, —$OC(O)OR^{2b}$, —$C(O)NR^{2a}R^{2b}$, —$C(O)N(OH)R^{2b}$, —$NR^{2b}C(O)R^{2c}$, $C_{1-6}$ alkyl-$NR^{2b}C(O)R^{2c}$, —$NR^{2b}C(O)OR^{2c}$, $C_{1-6}$ alkyl-$NR^{2b}C(O)OR^{2c}$, —$OC(O)NR^{2b}R^{2c}$, —$NR^{2b}C(O)NR^{2b}R^{2c}$, —$NR^{2b}C(NR^{2b})N R^{2b}R^{2c}$, —$C(O)NR^{2b}C(O)R^{2b}$, $C_{1-6}$ alkyl-$NR^{2b}C(O)NR^{2b}R^{2c}$, —$SR^{2a}$, —$SO_2R^{2b}$, —$SO_2OR^{2b}$, —$SO_2NR^{2b}R^{2d}$, —$NR^{2b}SO_2$ $R^{2b}$, —$P(O)(OR^{2b})_2$, —$B(OR^{2b})$, —CN, —$NO_2$, —$N_3$, heterocycloalkyl, aryl, heteroaryl, $C_{1-6}$ alkyl-heterocycloalkyl, $C_{1-6}$ alkyl-aryl, $C_{1-6}$ alkyl-O-aryl, $C_{1-6}$ alkyl-heteroaryl, and heteroaryl-aryl, and wherein the heterocycloalkyl, aryl and heteroaryl groups are optionally substituted with 1 to 2 $R^{2a}$ groups;

$R^{1a}$ is selected from the group consisting of —$OR^{1b}$ and —$NR^{1b}R^{1c}$;

$R^{1b}$ and $R^{1c}$ are each independently selected from the group consisting of H, $C_{1-6}$ alkyl, $C_{2-6}$ alkenyl, $C_{2-6}$ alkynyl, cycloalkyl, heterocycloalkyl, aryl, heteroaryl, $C_{1-6}$ alkyl-aryl, and $C_{1-6}$ alkyl-heteroaryl, wherein the cycloalkyl, heterocycloalkyl, aryl and heteroaryl groups are optionally substituted with from 1 to 4 Rid groups;

each $R^{1d}$ is independently selected from the group consisting of H, $C_{1-6}$ alkyl, $C_{1-6}$ alkoxy, and —$NO_2$;

each $R^{2a}$ is independently selected from the group consisting of H, $C_{2-6}$ alkenyl, $C_{2-6}$ alkynyl, cycloalkyl, heterocycloalkyl, aryl, heteroaryl, $C_{1-6}$ alkyl-cycloalkyl, $C_{1-6}$ alkyl-heterocycloalkyl, $C_{1-6}$ alkyl-aryl and $C_{1-6}$ alkyl-heteroaryl, optionally substituted with 1 to 2 $R^{2b}$ groups;

each $R^{2b}$ and $R^{2c}$ is independently selected from the group consisting of H, and $C_{1-6}$ alkyl;

each $R^{2d}$ is independently selected from the group consisting of H, $C_{1-6}$ alkyl, cycloalkyl, heterocycloalkyl, aryl, heteroaryl, $C_{1-6}$ alkyl-cycloalkyl, $C_{1-6}$ alkyl-heterocycloalkyl, $C_{1-6}$ alkyl-aryl and $C_{1-6}$ alkyl-heteroaryl, each optionally substituted with 1 to 2 $R^{2b}$ groups;

each of $L^1$ and $L^2$ are independently selected from the group consisting of a bond, $C_{1-6}$ alkylene, $C_{2-6}$ alkenylene, $C_{1-6}$ alkylene-O—, —O—$C_{1-6}$ alkylene, $C_{1-6}$ alkylene-$NR^{3a}$—, —$NR^{3a}$—$C_{1-6}$ alkylene, —C(O)—, $C_{1-6}$ alkylene-C(O)—, —C(O)—$C_{1-6}$ alkylene-NH—, —NH—$C_{1-6}$ alkylene-C(O)—, —C(O)N H—, —NHC(O)—, $C_{1-6}$ alkylene-NHC(O)—, —$SO_2NH$—, —$NHSO_2$—, —NHC(O)NH—, cycloalkylene, —N=N—, and —C($R^{3a}$)=N ($R^{3c}$)—, wherein the alkylene group is optionally substituted with from 1-4 $R^{3b}$ groups; $R^{3a}$ is selected from the group consisting of H, and $C_{1-6}$ alkyl;

each $R^{3b}$ is independently selected from the group consisting of H, $C_{1-6}$ alkyl, halogen, —$OR^3a$ and —$NR^{3a}R^{3a}$;

$R^{3c}$ is absent or —OH;

alternatively, $L^2$ is combined with $R^1$, $L^1$ is combined with $L^2$, $L^1$ is combined with $R^2$, two $R^1$ groups on adjacent ring atoms, or two $R^2$ groups on adjacent ring atoms are combined to form a 5-6 membered heterocycloalkyl with from 1 to 3 heteroatoms selected from N, O and S, or a 5-6 membered heteroaryl with from 1 to 3 heteroatoms selected from N, O and S, and optionally substituted with from 1 to 3 groups selected from the group consisting of H, $C_{1-6}$ alkyl and oxo;

subscripts m and n are each an integer from 1 to 3;

wherein:
(a) $L^1$ is a bond, $L^2$ is —C(O)NH—, ring B is phenyl, and at least one $R^2$ is —CN or phenyl, or (b) at least one $R^1$ is —C(O)OH, ring A is phenyl, $L^2$ is —C(O)NH—, and $L^1$ is a bond or $C_{1-6}$ alkylene, or
(c) each of ring A and ring B is phenyl, at least one $R^1$ is —C(O)OH or combined with $L^2$, and at least one $R^2$ is selected from the group consisting of H, —CN and —C(O)OH;

wherein when $R^1$ is —$CO_2H$, subscript n is 1, ring A is phenyl, $L^2$ is —C(O)NH—, $L^1$ is a bond, ring B is phenyl, subscript m is 1, and $R^2$ is phenyl, then the phenyl of $R^2$ is substituted with $C_{1-6}$ alkyl, or salts and isomers thereof, thereby expanding the chondrocyte populations in culture.

17. The method of claim 16, wherein the chondrocyte populations are harvested arthroscopically from an uninjured minor load-bearing area of a damaged joint.

18. The method of claim 16, further comprising transplanting the expanded chondrocyte populations to a mammal in need thereof.

19. The method of claim 18, further comprising administering to the mammal the compound of Formula I.

20. The method of claim 19, wherein the transplanting and administering are performed substantially concurrently.

21. The method of claim 18, wherein the mammal is a human, a dog, a horse or a cat.

\* \* \* \* \*